United States Patent
Wu-Wong

(10) Patent No.: US 9,566,303 B2
(45) Date of Patent: Feb. 14, 2017

(54) IRON-FIBER COMPOSITION, PREPARATION AND USES THEREOF

(71) Applicant: Vidasym, Inc., Libertyville, IL (US)

(72) Inventor: Jinshyun Ruth Wu-Wong, Libertyville, IL (US)

(73) Assignee: Vidasym, Inc., Libertyville, IL (US)

( * ) Notice: Subject to any disclaimer, the term of this patent is extended or adjusted under 35 U.S.C. 154(b) by 0 days.

(21) Appl. No.: 14/349,134

(22) PCT Filed: Oct. 12, 2012

(86) PCT No.: PCT/US2012/060011
§ 371 (c)(1),
(2) Date: Apr. 2, 2014

(87) PCT Pub. No.: WO2013/056085
PCT Pub. Date: Apr. 18, 2013

(65) Prior Publication Data
US 2014/0242187 A1    Aug. 28, 2014

Related U.S. Application Data

(60) Provisional application No. 61/546,657, filed on Oct. 13, 2011, provisional application No. 61/644,005, filed on May 8, 2012.

(51) Int. Cl.
*A61K 33/26* (2006.01)
*A61K 33/42* (2006.01)
*A61K 9/70* (2006.01)

(52) U.S. Cl.
CPC .............. *A61K 33/26* (2013.01); *A23L 33/165* (2016.08); *A23L 33/21* (2016.08); *A23L 33/29* (2016.08); *A61K 9/70* (2013.01); *A61K 33/42* (2013.01); *A23V 2002/00* (2013.01)

(58) Field of Classification Search
CPC .......... A61K 33/26; A61K 33/42; A61K 9/70; A23V 2002/00; A23L 33/165; A23L 33/21; A23L 33/29
See application file for complete search history.

(56) References Cited

U.S. PATENT DOCUMENTS

| | | | |
|---|---|---|---|
| 3,324,109 A | | 6/1967 | Eichel |
| 3,563,978 A | * | 2/1971 | Ochs ..................... C08B 37/125 424/485 |
| 3,591,616 A | | 7/1971 | Baldt |
| 4,225,592 A | | 9/1980 | Lakatos et al. |
| 5,624,668 A | | 4/1997 | Lawrence et al. |
| 5,662,922 A | | 9/1997 | Christensen |
| 6,022,619 A | | 2/2000 | Kuhn |
| 6,174,442 B1 | | 1/2001 | Geisser |
| 7,674,780 B2 | | 3/2010 | Newton et al. |
| 2003/0191090 A1 | | 10/2003 | Andreasen et al. |
| 2005/0084539 A1 | | 4/2005 | Handa et al. |
| 2005/0107253 A1 | | 5/2005 | Sano |
| 2005/0158431 A1 | | 7/2005 | Knoblock et al. |
| 2008/0145410 A1 | * | 6/2008 | Ambuhl ............. C01G 49/0018 424/439 |
| 2008/0234226 A1 | | 9/2008 | Erichsen et al. |
| 2010/0035830 A1 | | 2/2010 | Reim et al. |
| 2010/0305063 A1 | | 12/2010 | Reim et al. |
| 2011/0027418 A1 | * | 2/2011 | Horgan ................ B65D 81/268 426/61 |
| 2011/0086097 A1 | * | 4/2011 | Kaufmann ............. A61K 33/26 424/474 |
| 2012/0094355 A1 | | 4/2012 | Medhoff et al. |
| 2015/0368369 A1 | | 12/2015 | Wu-Wong |

FOREIGN PATENT DOCUMENTS

| | | | | |
|---|---|---|---|---|
| CN | | 1646549 A | 7/2005 | |
| CN | | 1798754 A | 7/2006 | |
| DE | 195 47 356 AI | | 6/1997 | |
| EP | | 1457256 | 9/2004 | |
| EP | | 1481982 A1 | 12/2004 | |
| EP | | 2204432 A1 | 7/2010 | |
| EP | | 2204432 A8 | 7/2010 | |
| JP | | H5-238940 A | 9/1993 | |
| NZ | | 560350 | 10/2010 | |
| NZ | | 574271 | 5/2011 | |
| WO | | WO02/46241 | * 6/2002 | ............. C08B 37/00 |
| WO | | WO 02/46241 | 6/2002 | |
| WO | WO 2005/000210 A2 | | 1/2005 | |
| WO | WO 2006/133334 | | 12/2006 | |
| WO | WO 2009/078037 | | 6/2009 | |
| WO | WO 2014/138016 | | 9/2014 | |

OTHER PUBLICATIONS

John G Reinhold, et al, Binding of Iron by Fiber of Wheat and Maize, 34 AM. J CLIN. NUTR. 1384, 1385 (1981).*
Behall et al. (May 1989) Diabetes Care 12(5):357-364, "Effect of Guar Gum on Mineral Balances in NIDDM Adults"
Bilba and Arsene (2008) Composites Part A 39: 1488, "Silane treatment of bagasse fiber for reinforcement of cementitious composites"
Cook et al. (Dec. 1983) Gastroenterology 85:1354-1358 "Effect of Fiber on Nonheme Iron Absorption" Retrieved from the internet Nov. 29, 2012. UEL<http://pdf.usaid.gov/pdf_docs/PNAAQ793.pdf>.
Coudray et al. (2003) J Nutr. 133:1-4, "Effects of Dietary Fibers on Magnesium Absorption in Animals and Humans"
Eberhardt et al. (2006) Bioresource Technology 97: 2371-2376, "Phosphate removal by refined aspen wood fiber treated with carboxymethyl cellulose and ferrous chloride"
Greger (1999) J Nutr. 129:1434S-1435S, "Nondigestible Carbohydrates and Mineral Bioavailability"
Gustafsson et al. (2003) Polymer 44:661-670, "The ultrastructure of spruce kraft pulps studied by atomic force microscopy (AFM) and X-ray photoelectron spectroscopy (XPS)"

(Continued)

*Primary Examiner* — Sean Basquill
(74) *Attorney, Agent, or Firm* — Swanson & Bratschun, L.L.C.

(57) ABSTRACT

Compositions comprising ferrous and/or ferric iron compounds and fiber in a complex, methods for preparing such compositions of matter, and the use thereof for treatment of adsorbing certain accessible targets in the gastrointestinal tract and in an extracorporeal system, are provided herein.

22 Claims, 34 Drawing Sheets

(56) References Cited

OTHER PUBLICATIONS

Han et al. (Sep. 2003) 6th Inter-Regional Conference on Environment-Water, "Land and Water Use Planning and Management," Albacete, Spain,, pp. 1-11, "Removal of Phosphorous Using Chemically Modified Lignocellulosic Materials"
International Preliminary Report on Patentability mailed Apr. 15, 2014 in PCT/US2012/060011.
International Search Report and Written Opinion mailed Dec. 24, 2012 in PCT/US2012/060011.
Raschka et al. (2005) Bone 37(5):728-735, "Mechanisms underlying the effects of inulin-type fructans on calcium absorption in the large intestine of rats"
Reinhold et al. (Jul. 1981) The American Journal of Clinical Nutrition 34:1384-1391, "Binding of iron by fiber of wheat and maize"
Scholz-Ahrens et al. (2007) J Nutr. 137 (11 Suppl): 2513S-2523S), "Inulin and Oligofructose and Mineral Metabolism: The Evidence from Animal Trials"
Shah et al. (2009) Diabetes Care, 32(6):990-995, "Effect of a High-Fiber Diet Compared With a Moderate-Fiber Diet on Calcium and Other Mineral Balances in Subjects With Type 2 Diabetes"
Spencer et al. (1991) J Nutr 121:1976-1983 , "Effect of Oat Bran Muffins on Calcium Absorption and Calcium, Phosphorus, Magnesium and Zinc Balance in Men"
Spengler et al. (1994) Eur. J. Clin. Chem. Clin. Biochem., 32:733, "Characterization and Extracorporeal Application of a New Phosphate-Binding Agent"
Unnithan et al. ( 2002) J. Appl. Polym. Sci. 84, 2541-2553, "Ability of Iron(III)-Loaded Carboxylated Polyacrylamide Grafted Sawdust to Remove Phosphate Ions from Aqueous Solution and Fertilizer Industry Wastewater: Adsorption Kinetics and Isotherm Studies"
Wang et al. (2010) BioResources 5(3): 1799-1810, "Study on Lignin Coverage of Masson Pine Fiber"
Fernandez et al. (Jan. 1982) The American Journal of Clinical Nutrition 35(1):100-106, "Components of fiber bind iron in vitro"
International Search Report and Written Opinion mailed Jun. 9, 2014 in PCT/US2014/20205.
Leigh (Aug. 1983) The American Journal of Clinical Nutrition 38(2):202-213, "Effects of pH and chelating agents on iron binding by dietary fiber: implications for iron availability"
EP Search Report issued on Jun. 2, 2015 in EP12840785.5.
EP Search Report issued on Jul. 1, 2015 in EP12840785.5.
International Preliminary Report on Patentability issued Sep. 8, 2015 in PCT/US2014/020205.
Report of the Dietary Fiber Definition Committee to the Board of Directors of the American Association of Cereal Chemists. Cereal Foods World. Mar. 2001;46(3):112-26.
Ciesielski et al. (2008) EJPAU 11(2), pp. 25 "Metal Complexes of Xanthan Gum"
Platt, et al. (1984) J. Food Sci., 49(2):531-535, "Binding of Iron by Cellulose, Lignin, Sodium Phytate and Beta-Glucan, Alone and in Combination, Under Simulated Gastrointestinal pH Conditions"

\* cited by examiner

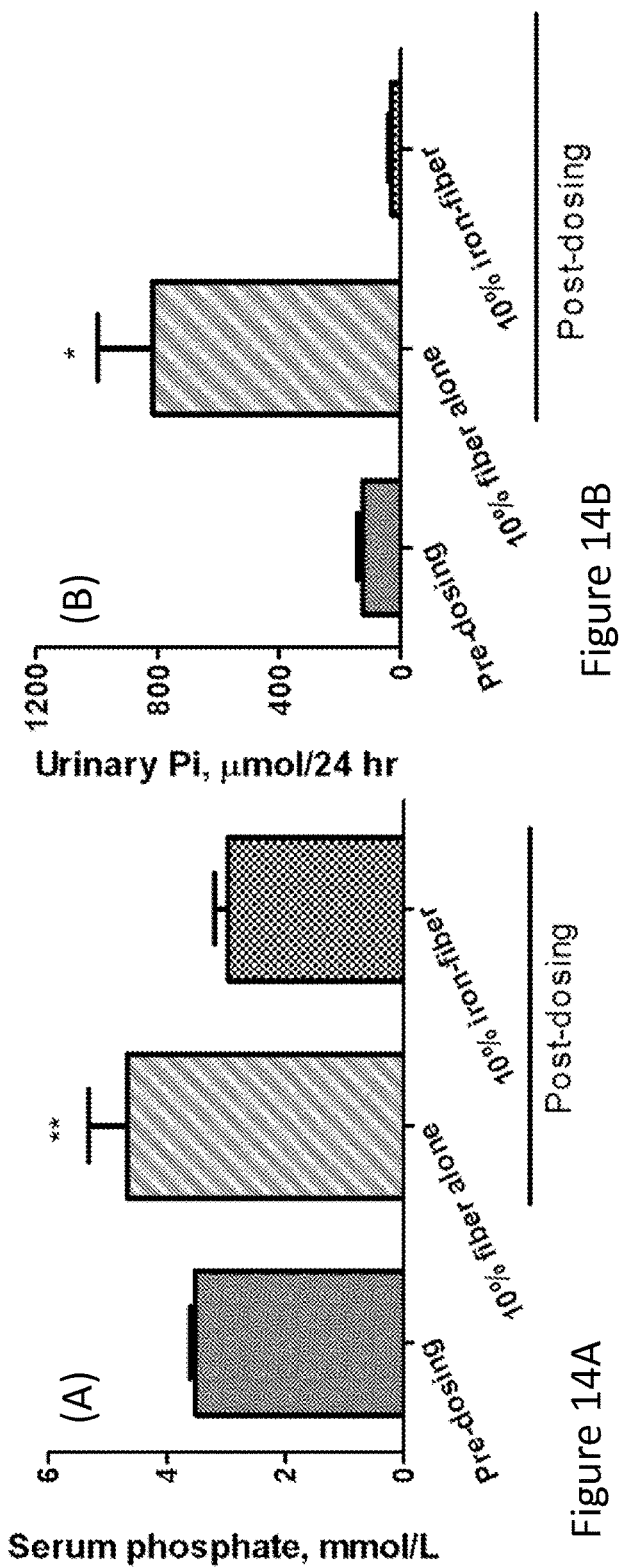
Figure 14A
Figure 14B
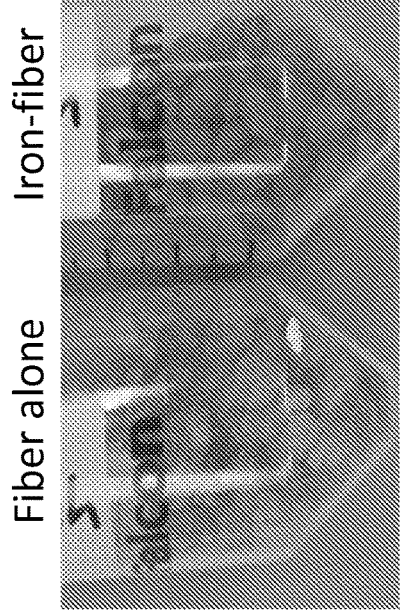
Figure 15

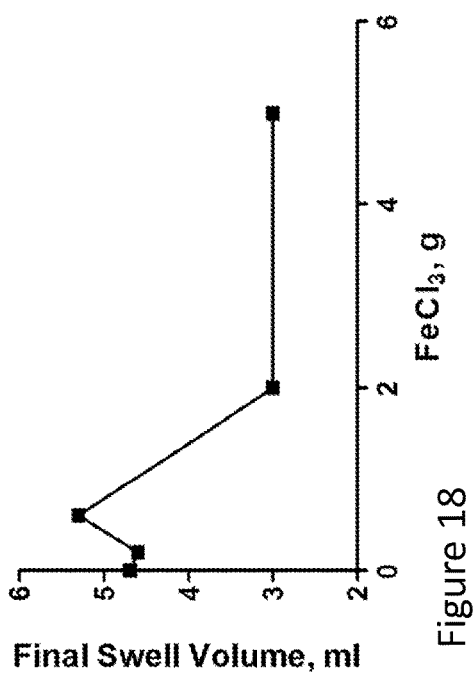
Figure 18
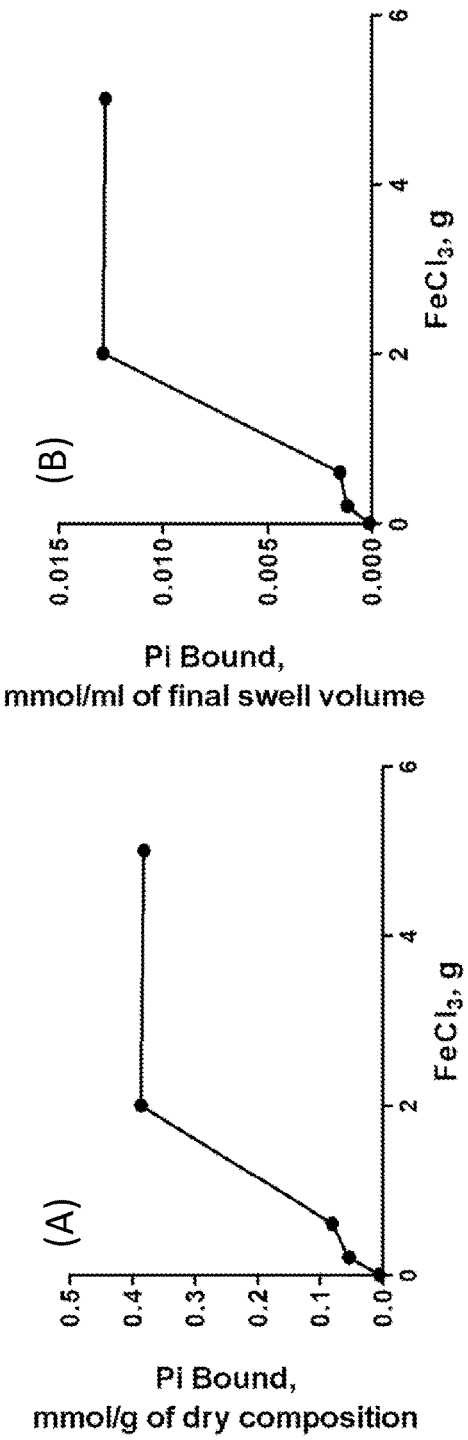
Figure 19B
Figure 19A

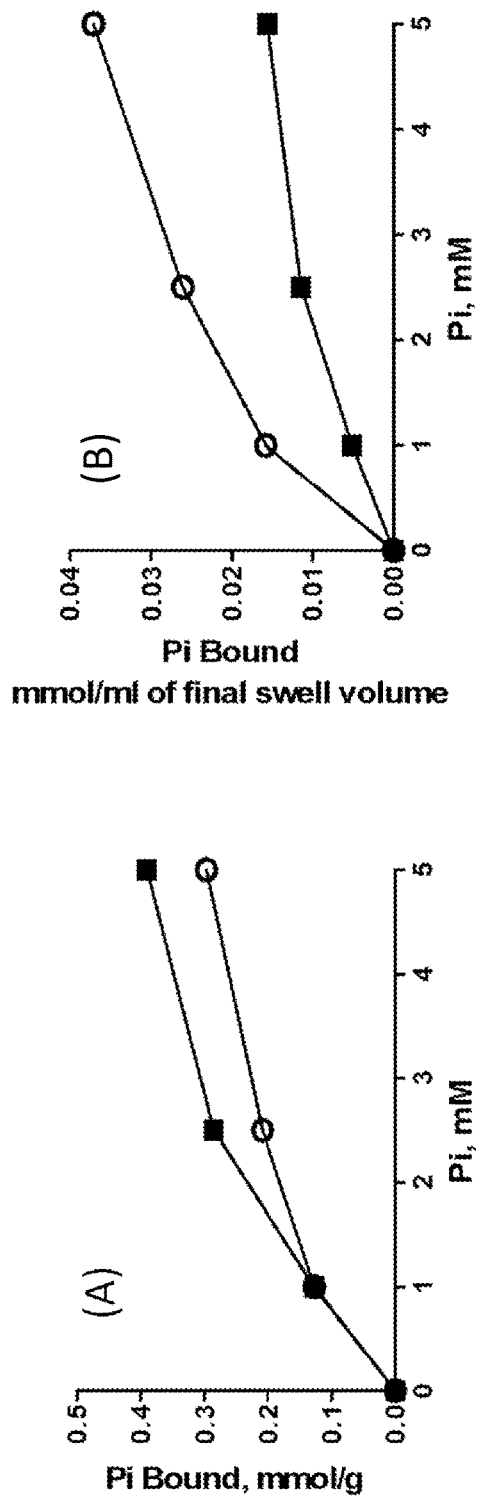
Figure 24A
Figure 24B
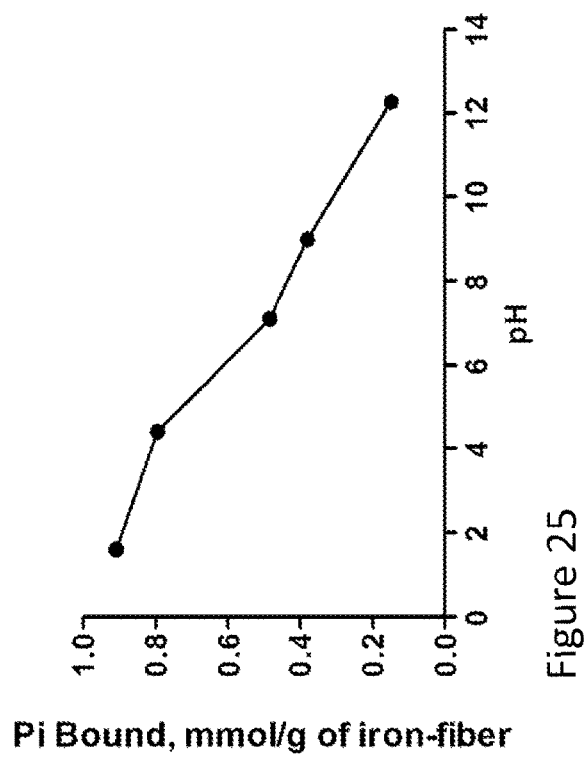
Figure 25

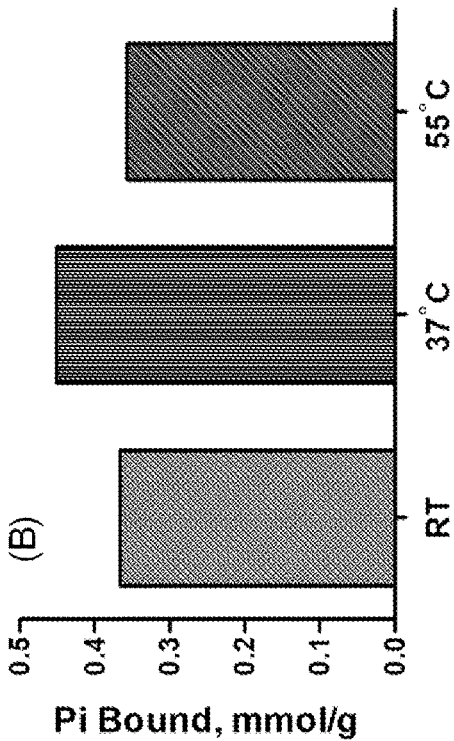
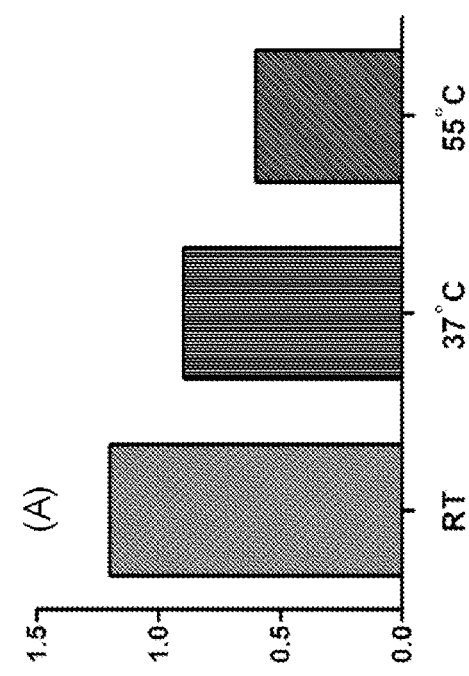
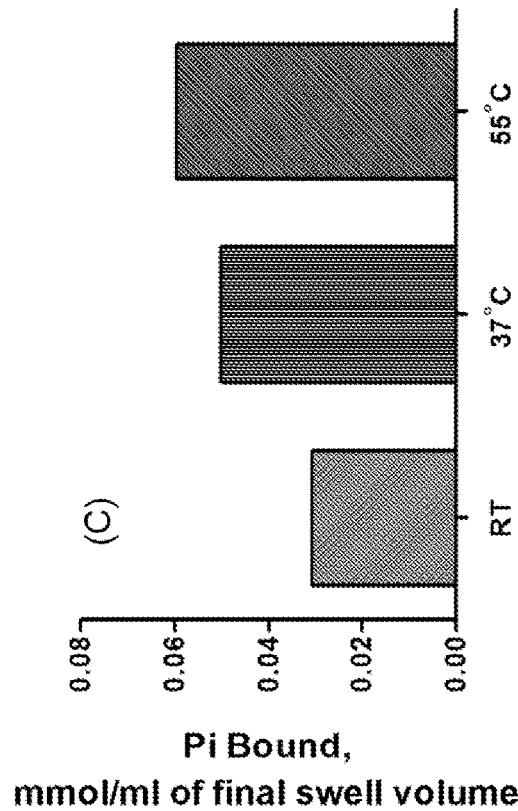
Figure 37B
Figure 37A
Figure 37C

IRON-FIBER COMPOSITION, PREPARATION AND USES THEREOF

RELATED APPLICATIONS

This application is a 35 U.S.C. §371 national phase application of PCT/US2012/060011, filed Oct. 12, 2012 (WO 2013/056085). PCT/US2012/060011 claims priority to U.S. Provisional Application Ser. No. 61/546,657, filed Oct. 13, 2011 and to U.S. Provisional Application Ser. No. 61/644,005, filed May 8, 2012. Each of these applications is incorporated by reference in its entirety.

FIELD OF THE INVENTION

The present application relates to medicinal compositions useful in adsorbing certain accessible targets in the gastrointestinal (GI) tract and in an extracorporeal system.

BACKGROUND

Iron polymer complexes that have favorable properties for therapeutic use are of great interest. Iron complexes with dextran, dextrose, maltose, sucrose, and fructose have been the focus of several patents and publications.

The textile industry uses particulates of iron oxides as pigments to dye fabrics. In addition, iron oxide is applied to textile fibers in an attempt to increase the conductivity of the synthetic fiber.

Biomass, either in its native state, or chemically modified, can be used to capture water pollutants and nutrients.

Studies have shown that iron adsorbed on synthetic filtration media or biomass can remove phosphates from water (Unnithan et al., J. Appl. Polym. Sci. 2002, 84, 2541-2553; Han et al., 6th Inter-Regional Conference on Environment-Water, "Land and Water Use Planning and Management," Albacete, Spain, 2003, pp. 1-11). Treating refined aspen wood fiber with iron-salt solutions demonstrated limited capacities to remove (ortho)phosphate from test solutions, but pre-treating fiber with carboxymethyl cellulose followed by ferrous chloride treatment improved the phosphate-binding capacity (Eberhardt et al. Bioresource Technology 2006, 97, 2371-2376).

Spengler et al. in 1994 (Eur. J. Clin. Chem. Clin. Biochem., 1994, 32:733) describes a method for preparing an insoluble iron(III) oxide hydroxide porous support by linking $FeCl_3.6H_2O$ to dextran using NaOH as the catalyst.

U.S. Pat. No. 5,624,668 describes ferric oxyhydroxide-dextran compositions for treating iron deficiency having ellipsoidal particles with a preferred molecular weight range of about 250,000 to 300,000 Daltons.

U.S. Pat. No. 6,022,619 describes a method of forming textile composites comprising coatings of iron oxides deposited on textile substrates, a method for the deposition of iron(III) oxides in status nascendi from an aqueous solution so as to form a coherent coating on a textile substrate.

U.S. Pat. No. 7,674,780 describes a process for preparing an iron-sucrose complex, substantially free of excipients, for providing an iron-sucrose complex co-precipitated with sucrose, and for providing iron-sucrose complexes in aqueous solution.

U.S. Publication 2008/0234226 mentions the use of iron (III) complex compounds with carbohydrates or derivatives thereof for the preparation of a medicament for oral treatment of iron deficiency states in patients with chronic inflammatory bowel disease, in particular Crohn's disease and colitis ulcerosa.

U.S. Publication 2010/0035830 describes iron-carbohydrate complex compounds which contain iron(II) in addition to iron(III), processes for their preparation, medicaments containing them, and the use thereof for treatment of iron deficiency anemia.

U.S. Publication 2011/0086097 describes a manufacture process for producing an iron-containing phosphate adsorbent based on starch and soluble carbohydrates, in particular, a process for manufacturing and isolating an iron(III)-based phosphate adsorbent which purportedly exhibits pharmacological properties.

WO 2009/078037 describes a process for manufacture of iron sucrose complex to treat anemia.

Preparation of complexes of carbohydrates with iron compounds have been disclosed in many patents and publications, and typically concern an absorbable composition in human gastrointestinal tract used to increase systemic iron delivery to treat iron deficiency anemia.

A diet high in fiber benefits health. Fiber adds bulk to the stool to alleviate constipation. It increases food volume without increasing caloric content. Fiber adsorbs water and forms a gel-like composition during digestion, slowing the emptying of the stomach and intestinal transit, shielding carbohydrates from enzymes, and delaying absorption of glucose by the gastrointestinal tract. Fiber consumption can lower total and LDL cholesterol.

The US Department of Agriculture lists functional fibers as isolated fiber sources that may be included in the diet (Dietary Reference Intakes for Energy, Carbohydrate, Fiber, Fat, Fatty Acids, Cholesterol, Protein, and Amino Acids (Macronutrients), 2005, Chapter 7: Dietary, Functional and Total fiber. U.S. Department of Agriculture, National Agricultural Library and National Academy of Sciences, Institute of Medicine, Food and Nutrition Board).

In general, fiber does not bind to minerals and vitamins and therefore does not restrict their absorption by the gastrointestinal tract. Rather, evidence exists that fiber sources improve absorption of minerals by the gastrointestinal tract although the subject is still under active research. Several reports indicate that fibers, especially the inulin-type, are promising substances that could help to improve the absorption of available minerals in human nutrition and by this contribute to bone health.

According to published papers (Behall et al. 1989, Diabetes Care 12: 357-364; Spencer et al. 1991, J Nutr 121: 1976-1983; Greger J L, J. Nutr. 1999, 129: 1434S-5S; Coudray et al. J. Nutr. 2003, 133:1-4; Raschka et al. Bone 2005, 37 (5): 728-35; Scholz-Ahrens et al. J. Nutr. 2007, 137 (11 Suppl): 2513S-2523S), nondigestible oligosaccharides have been shown to increase the absorption of several minerals (calcium, magnesium, in some cases phosphorus) and trace elements (mainly copper, iron, zinc). The stimulation of absorption was more pronounced when the demand for minerals was high. How fibers mediate this effect include different mechanisms such as acidification of the intestinal lumen by short-chain fatty acids increasing solubility of minerals in the gut, enlargement of the absorption surface, increased expression of calcium-binding proteins mainly in the large intestine, etc. Meanwhile the study by Shah et al. (2009, Diabetes Care, 32: 990-5) showed that fiber didn't significantly affect the intake of calcium and other minerals.

It would be of value to create novel compositions using fiber and iron that have favorable properties for therapeutic and nutritional use.

SUMMARY

Provided herein are novel compositions that retain the beneficial characteristics of fiber and at the same time change the nature of fiber to a composition of matter that adsorbs certain accessible targets in the gastrointestinal tract and in an extracorporeal system. In particular, iron compounds are attached to fiber to alter or add further benefit to the nature of fiber.

As such, provided herein are iron-fiber complex compositions having a high content of iron(II) and iron(III).

Exemplary fibers include natural fibers, man-made fibers, and combinations thereof. These fibers include multiple fiber types i.e., co-tri-polymers or random polymers containing various fiber compositions or they can be composed of blends and composites of fibers that optionally contain iron compounds.

Chemically, dietary fiber consists of non-starch polysaccharides such as arabinoxylans, cellulose, and many other plant components such as resistant dextrins, inulin, lignin, waxes, chitins, pectins, beta-glucans, and oligosaccharides.

Exemplary iron compounds useful herein include, but are not limited to iron(II) acetate, iron(II) citrate, iron(II) ascorbate, iron(II) oxalate, iron(II) oxide, iron(II) carbonate, iron(II) carbonate saccharate, iron(II) formate, iron(II) sulfate, iron(II) chloride, iron(III) chloride, iron(II) bromide, iron(II) iodide, iron(III) fluoride, iron(II) acetylacetonate, iron(III) phosphate, iron(III) pyrophosphate, and combinations thereof.

The iron-fiber compositions according to the application are oligo- or polynuclear iron compositions in which the iron atoms are bonded to one another via oxygen atoms and/or hydroxyl groups, and wherein the iron is bonded to the fiber in a complex and/or via carbon, oxygen, nitrogen, and/or hydrogen bridge bonds. The hydroxyl bridges also have a high binding affinity for Fe(II) and/or Fe(III). The iron-fiber compositions can also contain water bonded as a complex or via hydrogen bridge bonds.

The iron-fiber compositions according to the application are characterized by their content of iron(II) and iron(III). This means that some of the iron is present in the oxidation level of $2^+$ and some in the oxidation level of $3^+$. These are therefore so-called "mixed valence" compositions, in which the metal is present in several oxidation levels side by side.

In some embodiments, the content of iron(II) and iron(III) in the total iron content is at least 2 wt %. For example, the content of iron(II) and iron(III) in the total iron content can be 2 to 50 wt %, or 3 to 50 wt %, or 3 to 25 wt %, 10 to 50 wt %, or 10 to 40 wt %, or 15 to 30 w or 20 to 50 wt %, or about 10 wt %, or about 15 wt %, or about 20 wt %, or about 30 wt %, or about 40 wt %, or any other range or value within those ranges.

The content of fiber by weight of the compositions is 10 to 98 wt %, for example, about 10 to 80 wt. %, about 50 to 90 wt %, about 60 to 90 wt %, about 70 to 85 wt. %, about 35 to 65 wt %, about 40 to 60 wt. %, about 45 to 55 wt. %, or about 20 wt %, or about 30 wt %, or about 40 wt %, or about 50 wt % by weight, or any other range or value within those ranges.

The content of water in the iron-fiber compositions can be up to 10 wt. %, depending on the drying conditions. Illustratively, the water content is about 2 to 8 wt. %, about 3 to 7 wt. %, about 2 to 5 wt. %, or about 5 to 10 wt. %, or any other range within those ranges.

In some embodiments, the iron-fiber compositions comprise ferrous ($Fe^{2+}$) and/or ferric ($Fe^{3+}$) compounds and a dietary fiber in a complex or pharmaceutically acceptable salts thereof in a physiologically or pharmaceutically acceptable carrier. These compositions are useful for adsorbing undesirable agents including, but not limited to excess calcium, cholesterol, phosphate, potassium, sodium, as well as, toxins from infectious agents via in vivo, extracorporeal, ex vivo, or in vitro administration to a subject in need thereof.

Iron (II/III), which is present in the complex allows access to the analytes. In one embodiment, the iron-fiber complex compositions comprise 2 to 50 wt % of iron and 50 to 98 wt % of one or more fibers In one embodiment, the iron-fiber complex compositions comprise 10 to 50 wt % of iron and 50 to 90 wt % of one or more fibers.

In one embodiment, the iron-fiber complex compositions comprise 10 to 40 wt % of iron and 60 to 90 wt % of one or more fibers.

In one embodiment, the iron-fiber complex compositions comprise 15 to 30 wt % of iron and 70 to 85 wt % of one or more fibers.

In one embodiment, the iron-fiber complex composition is formulated as a medicament.

In another embodiment, the iron-fiber complex composition is suitable for oral administration.

In another embodiment, the effective amount for treating a subject is about 0.01 g/kg/day to about 20 g/kg/day.

In another embodiment, the iron-fiber complex is capable of binding to minerals, ions, toxins, metabolites at a wide pH range.

In another embodiment, the iron-fiber complex is stable at pH 1-12, and remains efficacious at a pH range between 1 to 12.

In another embodiment, the action of the iron-fiber composition is not affected by the iron based on its location in the iron-fiber complex.

In one embodiment, an elemental medical food suitable for mammals is provided comprising at least 400 mg of the iron-fiber composition described herein. The medical food can be in the form of a liquid solution; powder, bar, wafer, a suspension in an appropriate liquid or in a suitable emulsion, as detailed below. In some embodiments, the medical food may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents.

In another embodiment, a method for treating a patient suffering from abnormal mineral homeostasis with elevated calcium, phosphate, potassium, sodium in blood outside the normal range, comprising administering a therapeutically effective amount of the medical food is provided.

In yet another embodiment, method for treating a patient suffering from hyperlipidemia, comprising administering a therapeutically effective amount of the elemental medical food is provided.

In another embodiment, a method for treating a patient suffering from toxins from infectious agents in the gastrointestinal tract comprising administering to a patient in need thereof a therapeutically effective amount of the elemental medical food is provided.

In another embodiment, a method for treating a patient suffering from abnormal metabolic parameters selected from glucose, insulin, GLP-1, glucagon, glycerol, triglycerides, cholesterol, NEFA and leptin levels, comprising administering an effective amount of the elemental medical food is provided.

In some aspects, the elemental medical food is administered in an amount of a total serving of at least 0.01 g/kg/day and up to about 20 g/kg/day of the elemental medical food to the patient daily.

In one embodiment, the total amount of iron-fiber complex compositions given daily to a subject in need thereof in one dose or multiple doses.

In another aspect, a food supplement suitable for mammals comprising at least 400 mg of the iron-fiber composition is provided. The food supplement can be in the form of a liquid solution, powder, bar, wafer, a suspension in an appropriate liquid or in a suitable emulsion, as detailed below. In some embodiments, the food supplement may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents.

In another embodiment, a method for treating a patient suffering from abnormal mineral homeostasis with elevated calcium, phosphate, potassium, sodium in blood outside the normal range, and to maintain bone health comprising administering a therapeutically effective amount of the food supplement is provided.

In yet another embodiment, a method for maintaining bone health comprising administering to a subject an effective amount of the food supplement is provided.

In another embodiment, a method for maintaining a normal lipid profile and cardiovascular health comprising providing an effective amount of the food supplement to a subject is provided.

The disclosure provides a method for maintaining normal weight comprising providing an effective amount of the food supplement to a subject.

In a further embodiment, a method is provided for maintaining normal metabolic parameters such as glucose, insulin, GLP-1, glucagon, glycerol, triglycerides, cholesterol, NEFA and leptin levels, said method comprising providing an effective amount of the food supplement to a subject.

In certain aspects, the food supplement is administered in an amount of at least 0.75 g per day and up to 1500 g per day of the food supplement to the subject daily.

In another aspect, a method for preparing the disclosed compositions is provided. Generally, in one embodiment an iron salt, or a mixture of iron salts, is mixed together with a fiber carrier under acidic conditions at a pH in the range from about 1.0 to about 6.0 (for example, from about 1 to about 4, or from about 1 to about 3). To the mixture an alkali salt is optionally added. The resulting solution is purified of excess debris, salts, impurities, etc., by any suitable method to produce an iron-fiber complex with an elemental iron concentration between about 2% to about 50%.

In yet another aspect, the iron-fiber complex is prepared by a process comprising the steps of: (a) mixing one or more fibers and an iron compound, at a pH<3; (b) maintaining a temperature of reaction mixture of step (a) between ambient and 100° C.; (c) cooling the reaction mixture of step (b) to ambient temperature and washing until pH is neutral; and (d) isolating the iron-fiber complex compound formed, wherein the iron content is in an amount of from 2 to 50 wt %.

In yet another aspect, the selected weight ratio of fiber to iron compounds is from about 1:0.1 to about 1:100. For example, about 1:0.2, or about 1:1, or about 1:5, or about 1:10, or about 1:20, or about 1:50, or about 1:80, or about 1:100, or any other ratio or value within these ranges.

In yet another aspect, an optional acid is used to achieve a pH in a range of about 1 to about 3, wherein the acid is selected from the group of hydrogen halides and their aqueous solutions including, but not limited to: hydrochloric acid (HCl), hydrobromic acid (HBr), hydroiodic acid (HI), halogen oxoacids such as hypochlorous acid (HClO), chlorous acid ($HClO_2$), chloric acid ($HClO_3$), perchloric acid ($HClO_4$), and corresponding compounds for bromine and iodine, sulfuric acid ($H_2SO_4$), fluorosulfuric acid ($HSO_3F$), nitric acid ($HNO_3$), phosphoric acid ($H_3PO_4$), fluoroantimonic acid ($HSbF_6$), fluoroboric acid ($HBF_4$), hexafluorophosphoric acid ($HPF_6$), chromic acid ($H_2CrO_4$), boric acid ($H_3BO_3$). Other acids are contemplated herein and are easily identifiable by one of skill in the art.

In yet another aspect, an optional base or an alkali salt is added to the fiber/iron mixture, after being mixed under acidic conditions. In some aspects, the alkali salt is added to the fiber/iron mixture to achieve a pH of at least 3. In some aspects, the alkali salt is added to the fiber/iron mixture to achieve a pH of the solution in a range of greater than about 3 to no greater than about 12. Alkali carbonates and alkali metal hydroxides are illustrative alkali substances or bases useful herein, though others are contemplated. The base can be selected from the group including, but not limited to LiOH, KOH, NaOH, $NaHCO_3$, $Na_2CO_3$, $Ca(OH)_2$, $Mg(OH)_2$, $Li_2CO_3$, $K_2CO_3$, $CaCO_3$, $MgCO_3$, and $Na_2CO_3$. The base can comprise any wt. % of the total weight of the iron-fiber mixture, sufficient to alter the pH of the mixture to the desired range.

The temperature of the reaction mixture is in the range from about 20° C. to about 100° C., for example, about 30° C., about 40° C., about 50° C., about 60° C., about 70° C., about 80° C., about 90° C., or about 100° C. The time interval is in the range from about 60 minutes to about 48 hours, for example, about 2 hours, about 3 hours, about 4 hours, about 6 hours, about 8 hours, about 12 hours, about 18 hours, about 24 hours, about 30 hours, about 36 hours, about 42 hours, or about 48 hours.

BRIEF DESCRIPTION OF THE DRAWINGS

FIG. 14 is a graph illustrating (A) serum and (B) urinary (per 24-hr collecting period) phosphorus/phosphate (Pi) levels in rats fed a phosphate-enriched diet containing fiber alone or the iron-fiber composition. *$p<0.05$, **$p<0.01$ vs. pre-dosing.

FIG. 15 shows the physical appearance of feces samples collected from rats treated with fiber alone vs. iron-fiber.

FIG. 18 is a graph illustrating the final swell volume for the fiber-$FeCl_3$ preparation with 1 g fiber and 0, 0.2, 0.6, 2 and 5 g $FeCl_3$.

FIG. 19 is a graph illustrating the phosphate-binding property of the composition in FIG. 18 normalized by (A) per gram of dry composition, or (B) per ml of the final volume after the incubation with the phosphate buffer (final swell volume). Pi: phosphate.

FIG. 24 is a graph illustrating the phosphate-binding property of the iron-fiber composition (○) vs. sevelamer (■) normalized by (A) per gram of dry material or (B) per ml of the final swell volume at different concentrations of phosphate.

FIG. 25 is a graph illustrating the phosphate-binding property of the iron-fiber composition normalized by per gram of dry iron-fiber at different pH in the phosphate solution.

FIG. 37 illustrates the effect of incubation temperature during the iron-fiber preparation on (A) the final swell volume (after the incubation with the phosphate buffer), (B) phosphate-binding normalized by per gram of dry iron-fiber, and (C) phosphate-binding normalized by per ml of the final swell volume.

DETAILED DESCRIPTION

Figure 2:
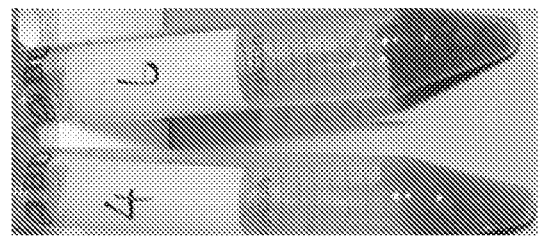
FIG. 2 shows the physical appearance of the fiber alone (without iron compounds) (Fiber: Tube 4) and the $FeCl_3$-Fiber-24 hr sample (Tube 6).

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims. Thus, there are a variety of suitable formulations of the compositions described herein. These formulations are exemplary and are in no way limiting. Furthermore, one skilled in the art will appreciate that routes of administering the compositions and/or salts thereof include, but are not limited to, oral or alimentary administration. Although more than one route can be used, a particular route can provide a more immediate and more effective response than another route in a given situation.

One skilled in the art will recognize many methods and materials similar or equivalent to those described herein, which could be used in and are within the scope of the practice of the present invention. The present invention is in no way limited to the methods and materials described.

Unless defined otherwise, technical and scientific terms used herein have the same meaning as commonly understood by one of ordinary skill in the art to which this invention belongs. Although any methods, devices and materials similar or equivalent to those described herein can be used in the practice or testing of the invention, the preferred methods, devices and materials are now described.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

As used in this application, including the appended claims, the singular forms "a," "an," and "the" include plural references, unless the content clearly dictates otherwise, and are used interchangeably with "at least one" and "one or more." Thus, reference to "a dietary fiber" includes mixtures of dietary fibers, reference to "an iron complex" includes mixtures of iron complexes, and the like.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

Disclosed herein are iron compounds complexed to fiber which alter or add further benefit to the nature of dietary fiber. As such, provided herein are iron-fiber compositions having a high content of iron(II) and/or iron (III). Exemplary fibers include natural fibers, man-made fibers, and combinations thereof. The polymer complex can be amorphous, crystalline and contain microdomains of both amorphous and crystalline regions ranging from 10% to 90% amorphous and 10% to 90% crystalline. The location of the iron(II) and iron(III) can be in either the amorphous or crystalline regions or both.

Dietary fiber refers to indigestible portion of plant foods. As used herein "dietary fiber" includes, but is not limited to non-starch polysaccharides such as arabinoxylans, cellulose, and many other plant components such as resistant dextrins, inulin, lignin, waxes, chitins, pectins, beta-glucans, and oligosaccharides. The dietary fiber may be naturally occurring, synthetic or a mixture thereof.

Exemplary iron compounds include, but are not limited to iron(II) acetate, iron(II) citrate, iron(II) ascorbate, iron(II) oxalate, iron(II) oxide, iron(II) carbonate, iron(II) carbonate saccharate, iron(II) formate, iron(II) sulfate, iron(II) chloride, iron(III) chloride, iron (II) bromide, iron (II) iodide, iron (III) fluoride, iron(II) acetylacetonate, iron (III) phosphate, iron (III) pyrophosphate, and combinations thereof.

The iron-fiber compositions or complexes according one embodiment are oligo- or polynuclear iron compositions in which the iron atoms are bonded to one another via oxygen atoms and/or hydroxyl groups, and wherein the iron is bonded to the fiber as a complex and/or via carbon, oxygen, nitrogen, and/or hydrogen bridge bonds. The hydroxyl bridges also have a high binding affinity for Fe(II) and/or Fe(III). The iron-fiber compositions can also contain water bonded as a complex or via hydrogen bridge bonds.

The iron-fiber compositions according to the invention are characterized by their content of iron(II) and iron(III). This means that some of the iron is present in the oxidation level of $2^+$ and some in the oxidation level of $3^+$. These are therefore so-called "mixed valence" compounds, in which the metal is present in several oxidation levels side by side.

In some embodiments, the content of iron(II) and iron(III) in the total iron content of the iron-fiber composition is at least 2 wt. %. For example, the content of iron(II) and iron(III) in the total iron content can be 2 to 50 wt %, or 3 to 50 wt. % or 3 to 25 wt. %, or 20 to 50 wt. %, or 10 to 50 wt %, or 10 to 40 wt. % or 15 to 30 wt %, or about 10 wt %, or about 15 wt %, or about 20 wt %, or about 30 wt %, or about 40 wt %, or any other range or value within those ranges. The content of fiber by weight of the composition is 10 to 98 wt. %, for example, about 10 to 80 wt. %, about 50 to 90 wt %, about 60 to 90 wt %, about 70 to 85 wt %, about 35 to 65 wt. %, about 40 to 60 wt. %, about 45 to 55 wt. %, or about 20%, or about 30%, or about 40%, or about 50% by weight, or any other range or value within those ranges. The iron(II) and iron(III) are on the surface of the fiber and in the bulk fiber; the selected weight ratio of surface vs. bulk iron content can be 10 to 90 wt % or 90 to 10 wt. % and in between. The action of the iron-fiber composition is not affected by the iron at one location compared to another. In some embodiments, the iron-fiber compositions comprise ferrous ($Fe^{2+}$) and/or ferric ($Fe^{3+}$) compounds and a dietary fiber in a complex or pharmaceutically acceptable salts thereof in a physiologically or pharmaceutically acceptable carrier. The compositions that make up a therapeutic formulation can be mixtures of non-iron containing fibers and iron(II) and iron(III)-containing fibers. As used herein, "iron" compound, salt, iron-fiber complex or composition thereof, the term "iron" includes both Iron (II) or Ferrous and Iron (III) or Ferric compounds or combinations thereof.

As used herein, the term "liquid" includes, but is not limited to water, bodily fluids, aqueous and organic solvents, aqueous and organic solutions.

In one embodiment, a medical food suitable for mammals is provided comprising at least 400 mg of the iron-fiber composition described herein. The medical food can be in the form of a liquid solution; powder, bar, wafer, a suspension in an appropriate liquid or in a suitable emulsion, as detailed below. In some embodiments, the medical food may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents.

As used herein the term "medical food," as defined in section 5(b) of the Orphan Drug Act (21 U.S.C. 360ee (b) (3)) is "a food which is formulated to be consumed or administered enterally under the supervision of a physician and which is intended for the specific dietary management of a disease or condition for which distinctive nutritional requirements, based on recognized scientific principles, are established by medical evaluation."

Formulations suitable for oral administration are described herein for purposes of illustration. Oral formulations can include of (a) liquid solutions, such as an effective amount of the composition thereof dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; (e) nano or micro particles; and (f) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The composition can be consumed at any time during the day, e.g. as a meal, before, during, or after a meal, etc.

The compositions of the invention described herein can be administered to an extracorporeal system to adsorb certain accessible targets in the extracorporeal system in vitro. Furthermore, the compositions of the invention can be administered to a subject in vivo or ex vivo.

The compositions of the invention can be administered to a cell, for example, to a cell of a subject. Subjects include, for example, bacteria, yeast, fungi, plants, and mammals. In some embodiments, the subject is a mammal Mammals include, but are not limited to, the order Rodentia, such as mice, and the order Logomorpha, such as rabbits, the order Carnivora, including Felines (cats) and Canines (dogs), the order Artiodactyla, including Bovines (cows) and Swines (pigs), the order Perssodactyla, including Equines (horses), the order Primates, Ceboids, or Simioids (monkeys), the order Anthropoids (humans and apes). Illustratively the mammal is the human. Furthermore, the subject can be the unborn offspring of any of the forgoing subjects, including mammals (e.g., humans), in which case any screening of the subject or cells of the subject, or administration of compositions to the subject or cells of the subject, can be performed in utero.

The amount or dose of a composition should be sufficient to affect a therapeutic or prophylactic response in the subject over a reasonable time frame. The appropriate dose will depend upon the nature and severity of the disease or affliction to be treated or prevented, as well as by other factors. For instance, the dose also will be determined by the existence, nature and extent of any adverse side effects that might accompany the administration of the particular composition. Ultimately, the attending physician will decide the dosage of the composition of the present invention with which to treat each individual patient, taking into consideration a variety of factors, such as age, body weight, general health, diet, sex, composition to be administered, route of administration, and the severity of the condition being treated. An exemplary dose of a composition is the maximum that a patient can tolerate without incurring serious side effects. Typical doses might be, for example, about 0.01 g/kg/day to about 20 g/kg/day.

The compositions can be used for any purpose including, without limitation, the treatment, prevention, or diagnosis of a disease or condition, the screening of compounds that can be used to treat, prevent, or diagnose a disease or condition, or the research of the underlying mechanisms or causes of a disease or condition, which research can be used, for example, in the development of methods to treat, prevent, or diagnose the disease or condition. Without wishing to be bound by any particular theory, it is believed that the compositions of the invention are particularly useful with respect to diseases and conditions involving the adsorption of certain accessible targets in gastrointestinal tract or in the extracorporeal system.

Diagnose", "diagnosing", "diagnosis", and variations thereof refer to the detection, determination, or recognition of a health status or condition of an individual based on one or more signs, symptoms, data, or other information pertaining to that individual. The health status of an individual can be diagnosed as healthy/normal (i.e., a diagnosis of the absence of a disease or condition) or diagnosed as ill/ abnormal (i.e., a diagnosis of the presence, or an assessment of the characteristics, of a disease or condition). The terms "diagnose", "diagnosing", "diagnosis", etc., encompass, with respect to a particular disease or condition, the initial detection of the disease; the characterization or classification of the disease; the detection of the progression, remission, or recurrence or reactivation of the disease; and the detection of disease response after the administration of a treatment or therapy to the individual. The diagnosis of a disease or condition includes distinguishing individuals who have said disease or condition from individuals who do not.

"Prognose", "prognosing", "prognosis", and variations thereof refer to the prediction of a future course of a disease or condition in an individual who has the disease or condition (e.g., predicting patient survival), and such terms encompass the evaluation of disease response to the administration of a treatment or therapy to the individual. "Prognosing" and variants thereof can also mean predicting evidence of disease (EVD) or no evidence of disease (NED) in the individual at a future preselected time point. The date of prognosing can be referred to as time point 1 (TP1), and the preselected future time point may be referred to as time point 2 (TP2) and can include a specific future date or range of dates, for example post-treatment follow-up.

"Evaluate", "evaluating", "evaluation", and variations thereof encompass "diagnosing," "treating," "prognosing" and monitoring of recurrence in a treated individual. "Evaluating" can include any of the following: 1) diagnosing, i.e., initially detecting the presence or absence of a disease or condition; 2) prognosing at time point 1 (TP1), the future outcome of treatment at time point 2 (TP2), i.e., where TP2 may follow therapy; 3) detecting or monitoring disease progression or recurrence after apparent cure of said disease or condition i.e., wherein "monitoring after apparent cure" means testing an individual a time point after he or she has received successful treatment, and/or 4) detecting progression from latent infection to active disease.

"Treatment," as used herein refers to an intervention performed with the intention of preventing the development or altering the pathology of a disorder. Accordingly, "treatment" refers to both therapeutic and prophylactic or preventative measures. Those in need of treatment include those already with the disorder as well as those in which the disorder is to be prevented.

"Therapy" as used herein refers to an intervention performed with the intention of preventing the development or altering the pathology of a disorder. "Therapy" refers to various methods that target particular diseases with particular disease fighting agents. For example, a targeted therapy might involve providing to a subject in need thereof the iron-fiber composition in a physiologically acceptable carrier for adsorbing undesirable agents including, but not limited to excessive amounts of calcium, cholesterol, phosphate, potassium, sodium, as well as, toxins from infectious agents via in vivo, extracorporeal, ex vivo, or in vitro administration As used utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

As used herein, the term "physiologically acceptable carrier" refers to any carrier or excipient commonly used with pharmaceuticals. Such carriers or excipients include, but are not limited to, oils, starch, sucrose and lactose.

A "pharmaceutically acceptable salt" or "salt" of an iron-fiber composition is a product of the disclosed composition that contains an ionic bond, and is typically produced by reacting the disclosed compositions with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising the disclosed compositions in a form suitable for administration to a subject. A pharmaceutical composition of the invention is preferably formulated to be compatible with its intended route of administration.

As used herein the term "therapeutically effective amount" generally means the amount necessary to ameliorate at least one symptom of a disorder to be prevented, reduced, or treated as described herein. The phrase "therapeutically effective amount" as it relates to the compositions described herein shall mean the dosage that provides the specific pharmacological response for which the composition is administered in a significant number of subjects in need of such treatment. It is emphasized that a therapeutically effective amount that is administered to a particular subject in a particular instance will not always be effective in treating the conditions/diseases described herein, even though such dosage is deemed to be a therapeutically effective amount by those of skill in the art.

Thus, in one aspect a method of treating a disease which benefits from adsorption of certain accessible targets in gastrointestinal tract or in an extracorporeal system is provided. The method comprises administering to a patient in need thereof a therapeutically effective amount of the composition of the instant disclosure. The foregoing method is suitable for use in a subject or patient that is afflicted with a disease or at risk for developing a disease, such as a disease that benefits from adsorption of certain accessible targets in gastrointestinal tract or in an extracorporeal system. Such diseases include, for example, a bone disorder, cardiovascular disease, a cardiovascular complication associated with renal disease, endothelial dysfunction, hyperparathyroidism, hypercalcemia, hyperphosphatemia, an immune disorder, left ventricular hypertrophy, a proliferative disease, proteinuria, renal disease, viral infection, bacterial infection, musculoskeletal disorders, high blood pressure, hypertriglyceridemia, lipid disorders, hyperlipoproteinemia, hyperlipidemia, dyslipidemia, diabetes, hypercholesterolemia, multiple sclerosis, myelodysplastic syndrome, proximal myopathy, premature aging, metabolic syndrome, insulin resistance, obesity. One or more symptoms of the disease is prevented, reduced, or eliminated subsequent to administration of the composition, thereby effectively treating or preventing the disease to at least some degree.

The patient or subject can be any animal, domestic, livestock or wild, including, but not limited to cats, dogs, horses, pigs and cattle, and preferably human patients. As used herein, the terms patient and subject may be used interchangeably.

In another aspect a method for preparing the disclosed compositions is provided. Generally, in one embodiment an iron salt, or a mixture of iron salts, is mixed together with a fiber carrier under acidic conditions at a pH in the range from about 1.0 to about 6.0 (e.g. from about 1 to about 4, or from about 1 to about 3). To the mixture an alkali salt is added. The resulting solution is purified of excess debris, salts, impurities, etc., by any suitable method to produce an iron-fiber complex with an elemental iron concentration between about 2% to about 50%.

In yet another aspect, the iron-fiber complex is prepared by a process comprising the steps of: (a) mixing one or more fibers and an iron compound, at a pH<3; (b) maintaining a temperature of reaction mixture of step (a) between ambient and 100° C.; (c) cooling the reaction mixture of step (b) to ambient temperature and washing until pH is neutral; and (d) isolating the iron-fiber complex compound formed, wherein the iron content is in an amount of from 2 to 50 wt %.

An acid is used optionally to achieve a pH in a range of about 1 to about 3, said acid is selected from the group of hydrogen halides and their solutions including, but not limited to: hydrochloric acid (HCl), hydrobromic acid (HBr), hydroiodic acid (HI), halogen oxoacids such as hypochlorous acid (HClO), chlorous acid (HClO$_2$), chloric acid (HClO$_3$), perchloric acid (HClO$_4$), and corresponding compounds for bromine and iodine, sulfuric acid (H$_2$SO$_4$), fluorosulfuric acid (HSO$_3$F), nitric acid (HNO$_3$), phosphoric acid (H$_3$PO$_4$), fluoroantimonic acid (HSbF$_6$), fluoroboric acid (HBF$_4$), hexafluorophosphoric acid (HPF$_6$), chromic acid (H$_2$CrO$_4$), boric acid (H$_3$BO$_3$). Other acids are contemplated herein and are easily identifiable by one skilled in the art.

After fiber and iron compounds are mixed under acidic conditions, a base or an alkali salt can be optionally added to the fiber/iron mixture to alter the pH to be at least 3. In various embodiments, the pH is adjusted to be in the range of greater than about 3 and less than about 12. Alkali carbonates and alkali metal hydroxides are illustrative bases or alkali substances useful herein, though others are contemplated. The base can be selected from the group including, but not limited to LiOH, KOH, NaOH, NaHCO$_3$, Na$_2$CO$_3$, Ca(OH)$_2$, Mg(OH)$_2$, Li$_2$CO$_3$, K$_2$CO$_3$, CaCO$_3$, MgCO$_3$, and Na$_2$CO$_3$. The base can comprise any wt. % of the total weight of the iron-fiber mixture, sufficient to alter the pH of the mixture.

The temperature of the reaction mixture is in the range from about 20° C. to about 100° C., for example, about 30° C., about 40° C., about 50° C., about 60° C., about 70° C., about 80° C., about 90° C., or about 100° C. The time interval is in the range from about 60 minutes to about 48 hours, for example, about 2 hours, about 3 hours, about 4 hours, about 6 hours, about 8 hours, about 12 hours, about 18 hours, about 24 hours, about 30 hours, about 36 hours, about 42 hours, or about 48 hours.

The following examples are provided for illustrative purposes only and are not intended to limit the scope of the application as defined by the appended claims. All examples described herein were carried out using standard techniques, which are well known and routine to those of skill in the art.

EXAMPLES

Example 1

Prepared an aqueous solution of FeCl$_3$ (FeCl$_3$.6H$_2$O, Sigma F2877) in water at 0.5 g/ml, at a pH in the range of 1-3.

Mixed 0.5 g dietary fiber (for example, Ultimate Fiber or equivalent) with 12.5 ml of the FeCl$_3$ solution (pH<3) and allowed the mixture to shake in a shaker for 1 hour (hr) or 24 hrs at room temperature with shaking. Washed with water until the supernatant was clear.

As a control, mixed 0.5 g fiber with 10 ml water. Gently shook the mixture for 24 hrs at room temperature.

Dried the materials using a food dehydrator for 24 hours.

With 0.08 gram of the dried composition, added 1 ml of D-PBS (Invitrogen) containing 10 mM phosphate to each sample and incubated at room temperature for at least 1 hr. Centrifuged and collected the supernatant.

Added 0.5 ml of D-PBS to the precipitate, mixed well, centrifuged and collected the supernatant. Repeated the above process for 5 times.

Determined the phosphate level in the supernatants using the phosphate colorimetric assay (Catalog #K410-500 from Biovision).

Figure 1:
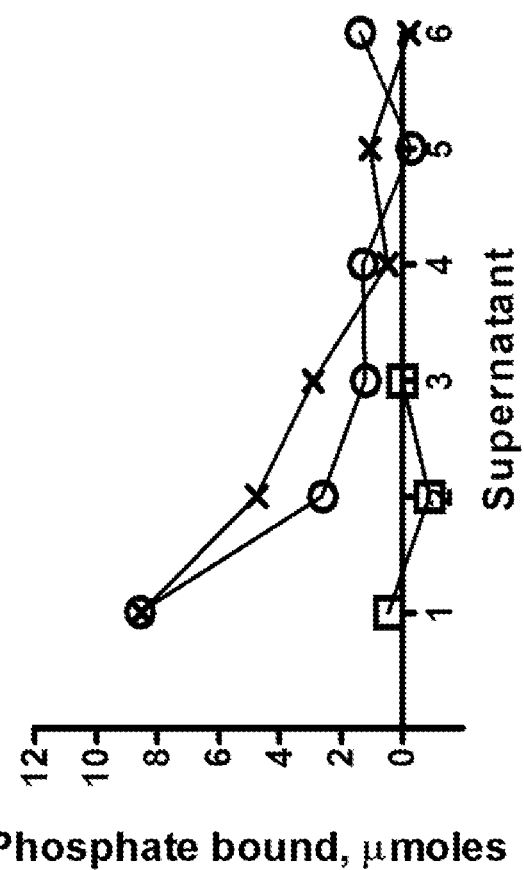
FIG. 1 is a graph illustrating the composition: fiber without iron compounds (Fiber, □), $FeCl_3$-fiber preparation after 1 hour (Fe-Fiber-1 hr, ○) and 24 hrs (Fe-Fiber-24 hr, x) of mixing during preparation, and their phosphate-binding capacity.

FIG. 1 shows the comparison between fiber without iron compounds and the iron-fiber preparation after 1 hr or 24 hrs of incubation on their effects in adsorbing phosphate. In the FeCl$_3$-fiber-1 hr composition, phosphate adsorbed in the 6 supernatants was 184 µmol/g of dry material. In the FeCl$_3$-fiber-24 hr composition, phosphate adsorbed in the 6 supernatants was 218 µmol/g of dry material. The fiber without FeCl$_3$ composition adsorbed 0 µmol of phosphate. FIG. 2 shows a picture of the fiber without iron compounds (Tube 4) and FeCl$_3$-fiber-24 hr (Tube 6).

Example 2

Prepared an aqueous solution of FeCl$_3$ in water at 0.5 g/ml, preferably at pH in the range of 1-3.

Mixed 0.5 g fiber with 5 g FeCl$_3$ in 10 ml water. Shook the mixture gently for 24 hrs or 48 hrs at room temperature. Added 0.1 g KOH. Mixed and incubated at room temperature for at least 1 hr with shaking. Washed with water until the supernatant was clear (using centrifugation or by filtering through a filter paper).

As a control, mixed 0.5 g fiber with 10 ml water. Incubated the mixture for 48 hrs at room temperature with shaking. Added 0.1 g KOH. Washed with water until the supernatant was at pH=7.

Dried the materials using a food dehydrator for 24 hours.

With 0.08 gram of the dried composition, added 1 ml of D-PBS (Invitrogen) containing 10 mM phosphate to each sample and incubate at room temperature for at least 1 hr. Centrifuged and collected the supernatant.

Added 0.5 ml of D-PBS to the precipitate, mixed well, centrifuged and collected the supernatant. Repeated the above process for 5 times.

Determined the phosphate level in the supernatants using the phosphate colorimetric assay (Catalog #K410-500 from Biovision).

Figure 4:
FIG. 4 shows the physical appearance of fiber alone treated with KOH (Tube 1), $FeCl_3$-fiber preparation after 24 hours (Tube 2) and 48 hr (Tube 5) of mixing before addition of KOH.
Figure 3:
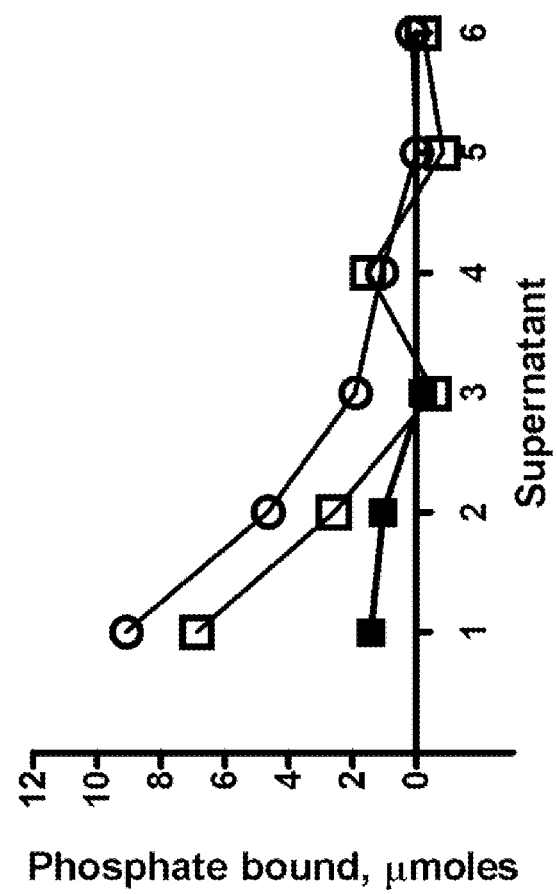
FIG. 3 is a graph illustrating the composition: fiber alone treated with KOH (Fiber-KOH, ■), $FeCl_3$-fiber preparation after 24 hours (Fe-Fiber-24 hr, ○) and 48 hr (Fe-Fiber-48 hr, □) of mixing before addition of KOH, and their phosphate-binding capacity.

FIG. 3 shows the comparison between fiber without iron compounds and the iron-fiber preparation after 24 hrs or 48 hrs of incubation on their effects in adsorbing phosphate. In the FeCl$_3$-fiber-48 hr composition, phosphate adsorbed in the 6 supernatants was 118 µmol/g dry composition phosphate. In the FeCl$_3$-fiber-48 hr composition, phosphate adsorbed in the 6 supernatants was 118 µmol/g of dry material. In the FeCl$_3$-fiber-24 hr composition, phosphate adsorbed in the 6 supernatants was 212 µmol/g of dry material. The fiber alone treated with KOH adsorbed phosphate at 28 µmol/g of dry material in the 6 supernatants. FIG. 4 shows the physical appearance of the fiber alone (Tube 1) vs. the FeCl$_3$-fiber-48 hr sample (Tube 2) and the FeCl$_3$-fiber-24 hr sample (Tube 6).

Example 3

Mixed 0.5 g or 1 g fiber with 5 g FeCl$_3$ in 10 ml water. Incubated the mixture for 24 hrs at room temperature with shaking. Added 0.67 g NaOH in 1 ml of water. Mixed and incubated at room temperature for at least 1 hr with shaking. Washed with water until the supernatant was clear.

Adjusted the pH with more NaOH until pH=7. Then washed with water for two more times (by centrifugation).

Took ~1 g of the wet material. Added 0.5 ml of D-PBS and incubated for 30 mM, mixed well, centrifuged and collected the supernatant.

Added 0.5 ml of D-PBS to the precipitate, mixed well, centrifuged and collected the supernatant. Repeated the above process 3 times.

Added 0.5 ml of D-PBS to the precipitate, incubated for 10 min, centrifuged and collected the supernatant.

Added 0.5 ml of D-PBS to the precipitate, incubated for 30 min, centrifuged and collected the supernatant.

Determined the phosphate level in the supernatants using the phosphate colorimetric assay (Catalog #K410-500 from Biovision).

Figure 6:
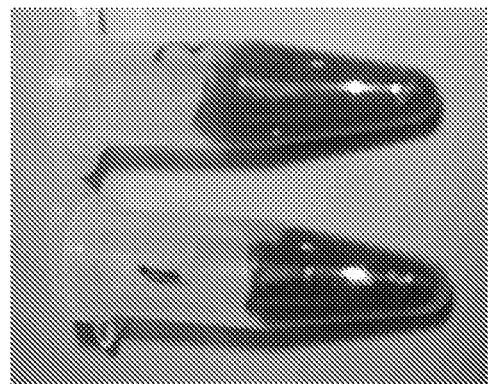
FIG. 6 shows the physical appearance of the two preparations. Tube 1, the fiber:$FeCl_3$ at a ratio of 1:10 composition. Tube 2: the fiber:$FeCl_3$ at a ratio of 1:5 composition.
Figure 5:
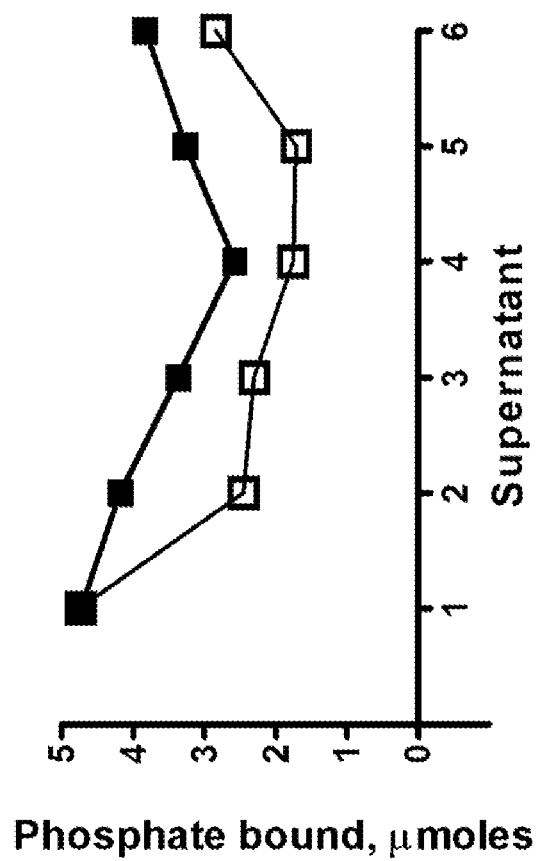
FIG. 5 is a graph illustrating the properties of fiber:$FeCl_3$ at the ratio of 1:10 (■) vs. fiber:$FeCl_3$ at the ratio of 1:5 (□) on adsorbing phosphate.

FIG. 5 shows the comparison between the fiber:$FeCl_3$ at 1:10 vs. the fiber:$FeCl_3$ at 1:5 on their effects in adsorbing phosphate. The fiber:$FeCl_3$=1:10 composition adsorbed 27 μmol of phosphate per gram of the wet composition. The fiber:$FeCl_3$=1:5 composition adsorbed 14 μmol of phosphate. FIG. 6 shows the physical appearance of the two preparations (Tube 1: The fiber:$FeCl_3$ at 1:10 composition. Tube 2: The fiber:$FeCl_3$ at 1:5 composition).

Example 4

Mixed 2 g or 3 g fiber with 5 g $FeCl_3$ in 30 ml water. Incubated the mixture for 2 hrs at room temperature with shaking. Added 0.3 g KOH (pH ~4.5). Mixed and incubated at room temperature for at least 1 hr with shaking. Washed with water until the supernatant was clear.

Adjusted the pH with NaOH until pH=7. Then washed with water for two more times (by centrifugation).

Took ~1 g of the wet material. Added 0.5 ml of D-PBS and incubated for 30 min, mixed well, centrifuged and collected the supernatant.

Added 0.5 ml of D-PBS to the precipitate, mixed well, centrifuged and collected the supernatant. Repeated the above process for 3 times.

Added 0.5 ml of D-PBS to the precipitate, incubated for 10 min, centrifuged and collected the supernatant.

Added 0.5 ml of D-PBS to the precipitate, incubated for 30 min, centrifuged and collected the supernatant.

Determined the phosphate level in the supernatants using the phosphate colorimetric assay (Catalog #K410-500 from Biovision).

Figure 8:
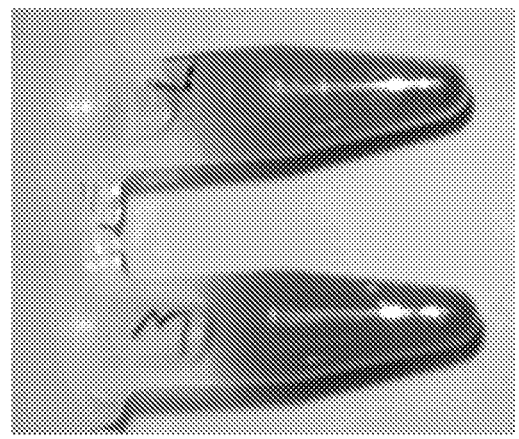
FIG. 8 shows the physical appearance of the two preparations. Tube 3: The fiber:$FeCl_3$=2:5 composition. Tube 4: The fiber:$FeCl_3$=3:5 composition.
Figure 7:
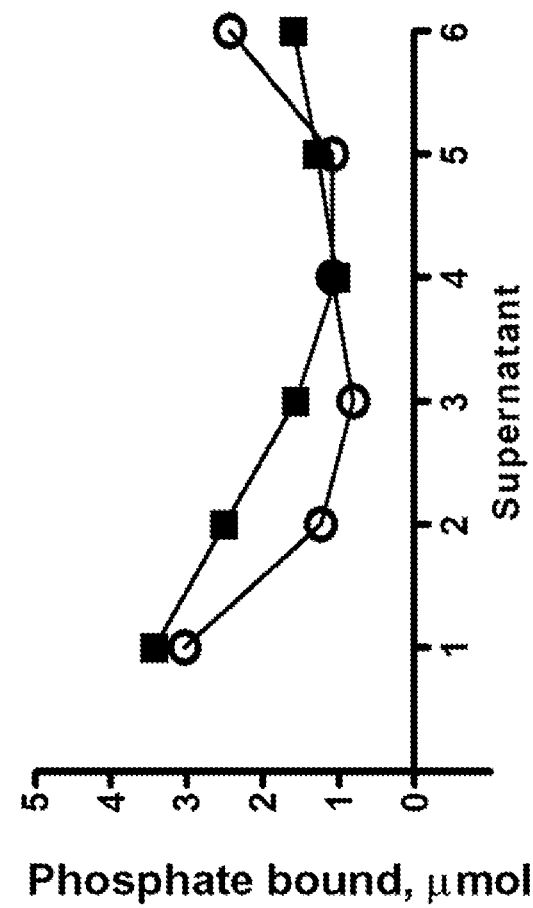
FIG. 7 is a graph illustrating the properties of the fiber:$FeCl_3$ at the ratio of 2:5 (○) composition vs. the fiber:$FeCl_3$=3:5 (■) composition on adsorbing phosphate.

FIG. 7 shows the comparison between the fiber:$FeCl_3$=2:5 composition vs. the fiber:$FeCl_3$=3:5 composition on their effects in adsorbing phosphate. The fiber:$FeCl_3$=2:5 composition adsorbed 9 μmol of phosphate per gram of the wet material. The fiber:$FeCl_3$=3:5 composition adsorbed 10 μmol of phosphate. FIG. 8 shows the physical appearance of the two preparations (Tube 3: The fiber:$FeCl_3$=2:5 composition. Tube 4: The fiber:$FeCl_3$=3:5 composition).

Example 5

Mixed 4 g or 5 g fiber with 5 g $FeCl_3$ in 110 ml water. Incubated the mixture for 2 hrs at room temperature with shaking. Added NaOH to pH=9. Mixed and incubated at room temperature for at least 1 hr with shaking. Washed with water until the supernatant was clear (pH=7.0).

Took ~1 g of the wet material. Added 0.5 ml of D-PBS and incubated for 30 min, mixed well, centrifuged and collected the supernatant.

Added 0.5 ml of D-PBS to the precipitate, mixed well, centrifuged and collected the supernatant. Repeated the above process for 4 times.

Added 0.5 ml of D-PBS to the precipitate, incubated for 30 min, centrifuged and collected the supernatant.

Determined the phosphate level in the supernatants using the phosphate colorimetric assay (Catalog #K410-500 from Biovision).

Figure 9:
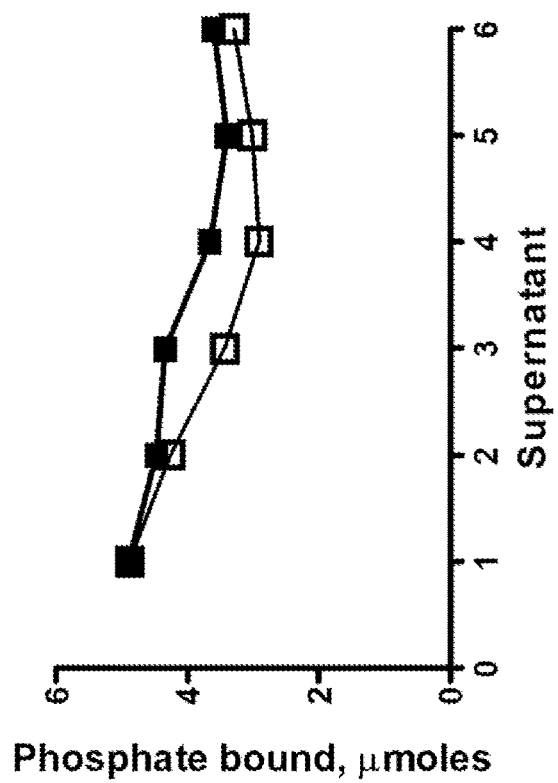
FIG. 9 is a graph illustrating the properties of the fiber:$FeCl_3$=4:5 (■) composition vs. the fiber:$FeCl_3$=1:1 (□) composition on adsorbing phosphate.

FIG. 9 shows the comparison between the fiber:$FeCl_3$=4:5 composition vs. the fiber:$FeCl_3$=1:1 composition on their effects in adsorbing phosphate. The fiber:$FeCl_3$=4:5 composition adsorbed 25 μmol of phosphate per gram of the wet material. The fiber:$FeCl_3$=1:1 composition adsorbed 25 μmol of phosphate.

Example 6

Took ~1 g of the fiber:$FeCl_3$=1:1 composition from Example 5. Added 0.5 ml of D-PBS. In one tube, added 2 μl of NaOH at 12.5 N. In another tube, added 2 μl of concentrated HCl. In another tube, added 2 μl of concentrated acetic acid. Incubated for 30 min at room temperature, mixed well, measured pH, centrifuged and collected the supernatant.

Added 0.5 ml of D-PBS to the precipitate. Adjusted the pH by adding NaOH (12.5 N) or concentrated HCl or concentrated acetic acid as described above to the corresponding tubes. Mixed well, determined pH, centrifuged and collected the supernatant.

Added 0.5 ml of D-PBS to the precipitate, mixed well, centrifuged and collected the supernatant immediately. Repeated 3 times.

Added 0.5 ml of D-PBS to the precipitate, incubated for 30 min, centrifuged and collected the supernatant.

Figure 10:
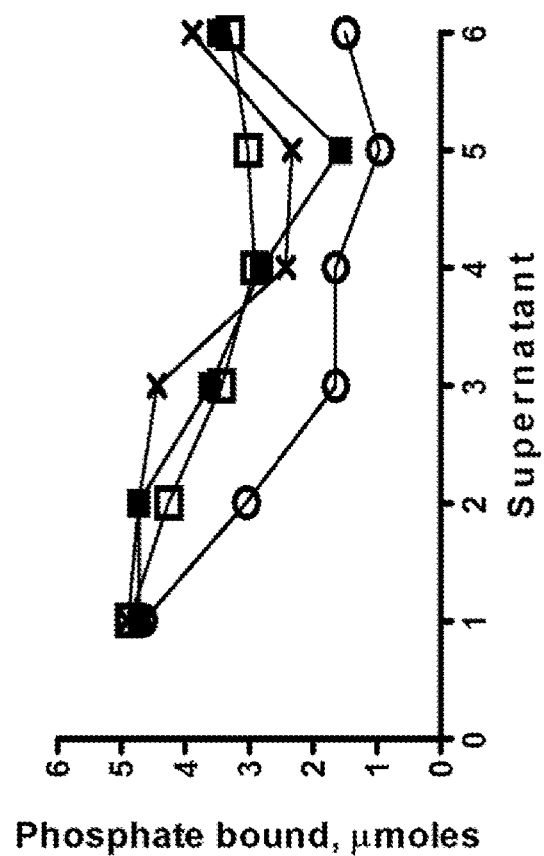
FIG. 10 is a graph illustrating the phosphate-binding properties of the fiber:$FeCl_3$=1:1 composition at different pH. □: no pH adjustment (pH=7 at each supernatant). ○: adding NaOH. X: adding acetic acid. ■: adding HCl.

Determined the phosphate level in the supernatants using the phosphate colorimetric assay (Catalog #K410-500 from Biovision). FIG. 10 shows the phosphate-binding properties of the fiber:$FeCl_3$=1:1 composition at different pH. Table 1 summarizes the data.

| Supernatant | Iron:fiber at 1:1 0.88 g Phosphate Bound, μmoles | pH | Iron:fiber at 1:1 + NaOH 0.89 g Phosphate Bound, μmoles | pH | Iron:fiber at 1:1 + HCl 0.93 g Phosphate Bound, μmoles | pH | Iron:fiber at 1:1 + acetic acid 1.02 g Phosphate Bound, μmoles | pH |
|---|---|---|---|---|---|---|---|---|
| | Weight of wet composition used in assay | | | | | | | |
| 1 | 4.89 | 7 | 4.66 | 8 | 4.71 | 5 | 4.90 | 6 |
| 2 | 4.27 | 7 | 3.05 | 10 | 4.73 | 3 | 4.74 | 4 |
| 3 | 3.44 | 7 | 1.65 | 10 | 3.61 | 6 | 4.45 | 7 |
| 4 | 2.92 | 7 | 1.65 | 10 | 2.80 | 6.5 | 2.42 | 7 |

-continued

| Supernatant | Iron:fiber at 1:1 | pH | Iron:fiber at 1:1 + NaOH | pH | Iron:fiber at 1:1 + HCl | pH | Iron:fiber at 1:1 + acetic acid | pH |
|---|---|---|---|---|---|---|---|---|
| | Weight of wet composition used in assay | | | | | | | |
| | 0.88 g Phosphate Bound, μmoles | | 0.89 g Phosphate Bound, μmoles | | 0.93 g Phosphate Bound, μmoles | | 1.02 g Phosphate Bound, μmoles | |
| 5 | 3.02 | 7 | 0.96 | 9 | 1.57 | 7 | 2.32 | 7 |
| 6 | 3.30 | 7 | 1.49 | 9 | 3.47 | 7 | 3.89 | 7 |
| Sum of phosphate bound, μmoles | 21.84 | | 13.45 | | 20.90 | | 22.72 | |
| μmoles phosphate bound/g of wet material | 24.8 | | 15.1 | | 22.5 | | 22.3 | |

Example 7

Mixed 0.5 g fiber with 5 g $FeCl_3$ in 10 ml water. Incubated the mixture overnight at room temperature. Added 0.1 g KOH. Mixed and incubated at room temperature for at least 1 hr. Washed with water until the supernatant was clear.

As a control, mixed 0.5 g fiber with 10 ml water. Incubated the mixture overnight at room temperature. Added 0.1 g KOH. Mixed and incubated at room temperature for at least 1 hr. Washed with water until the supernatant was clear.

Removed 1 g of the wet fiber mixture from each sample to a column; added D-PBS (Invitrogen) containing 10 mM phosphate. Incubated for at least 1 hr at room temperature. Collect fractions at 1 ml/fraction.

Determined the phosphate level in the fractions using the phosphate colorimetric assay (Catalog #K410-500 from Biovision).

Figure 11:
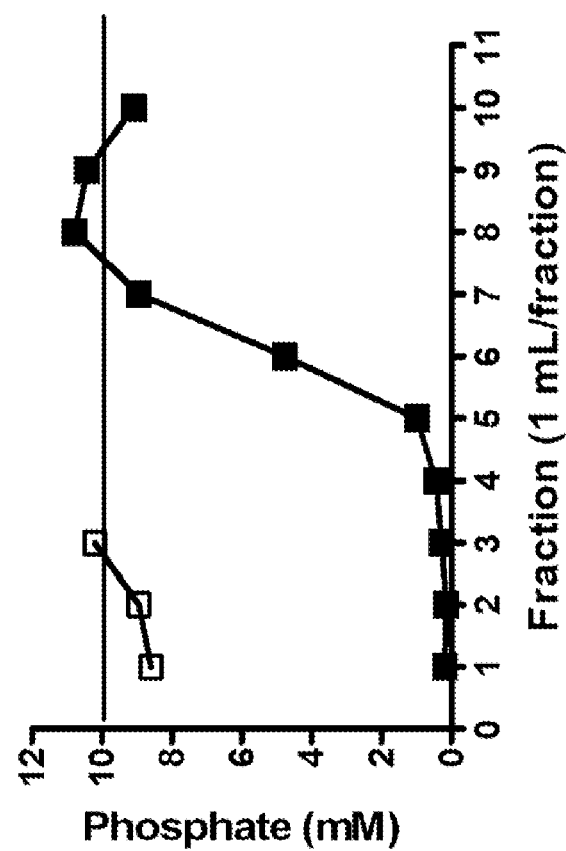
FIG. 11 is a graph illustrating the fiber alone (without iron compounds, □) vs. fiber:$FeCl_3$ at 1:10 (■) preparation on phosphate-binding using a column and fraction collection.

FIG. 11 shows the comparison between fiber without iron compounds and the iron-fiber preparation on their effects in adsorbing phosphate. The graph shows the unbound (rather than bound) phosphate. Phosphate adsorbed in the fractions was 49 μmol/g of wet material. The fiber alone composition didn't adsorb phosphate.

Example 8

Mixed 100 g dietary fiber (e.g. Organic Triple Fiber or equivalent) with 500 g of $FeCl_3$ in 1.5 liter of water. Incubated the mixture overnight at room temperature. Added 10 g KOH. Mixed and incubated at room temperature for at least 1 hr. Washed with water until the supernatant was clear.

As a control, mixed 100 g fiber with 1.5 liter water. Incubated the mixture overnight at room temperature. Added 0.1 g KOH. Mixed and incubated at room temperature for at least 1 hr. Washed with water until the supernatant was clear.

Removed 1 g of the wet material (1 g wet fiber=0.12 g dry fiber) from each sample to a column, added D-PBS (Invitrogen) containing 10 mM phosphate. Incubated for at least 1 hr at room temperature. Collected fractions at 1 ml/fraction.

Determined the phosphate level in the fractions using the phosphate colorimetric assay (Catalog #K410-500 from Biovision).

Figure 12:
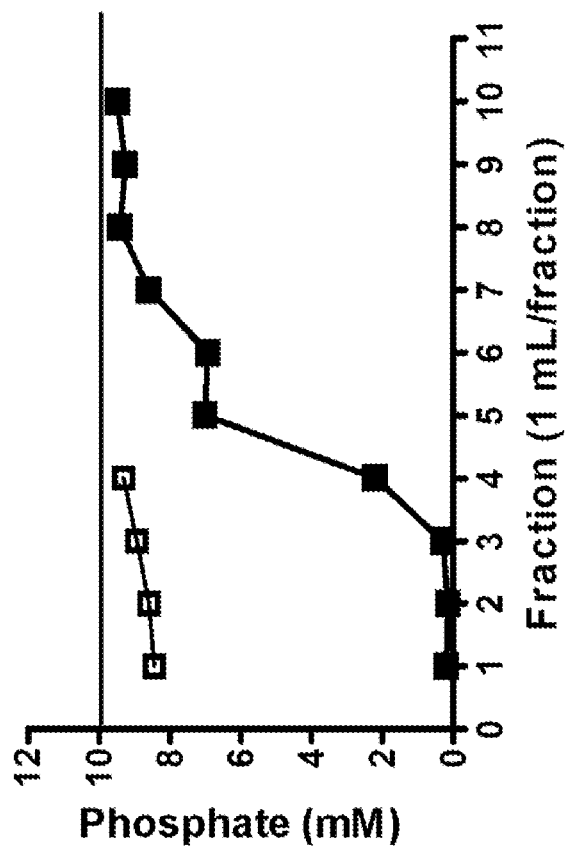
FIG. 12 is a graph illustrating a larger scale preparation of the fiber:$FeCl_3$ at 1:10 (■) composition on phosphate-binding (vs. fiber alone, □) using a column and fraction collection.

FIG. 12 shows the comparison between fiber without iron compounds and the iron-fiber preparation on their effects in adsorbing phosphate. The graph shows the unbound (rather than bound) phosphate. Phosphate adsorbed in the fractions was 47 μmol/g of wet material.

Example 9

Mixed 100 g dietary fiber with 100 g of $FeCl_3$ in 2.2 liter of water. Incubated the mixture for 24 hrs at room temperature with shaking. Added 46 g NaOH. Mixed and incubated at room temperature for at least 1 hr with shaking. Washed with water until the supernatant was clear.

Dried the materials for 24 hours using a food dehydrator.

With 1 gram of the dried composition, added 4 ml of a phosphate solution containing 20.4 mM $KH_2PO_4$ and 23.9 mM $K_2HPO_4$ and incubated at room temperature for at least 1 hr. Centrifuged and collected the supernatant.

As a control, mixed 1 g of dietary fiber Metamucil with 4 ml of a phosphate solution containing 20.4 mM $KH_2PO_4$ and 23.9 mM $K_2HPO_4$ and incubated at room temperature for at least 1 hr. The liquid portion was completely soaked up by Metamucil. Therefore, added 2 more ml of the phosphate solution containing 20.4 mM $KH_2PO_4$ and 23.9 mM $K_2HPO_4$. Centrifuged and collected the supernatant.

Figure 13:
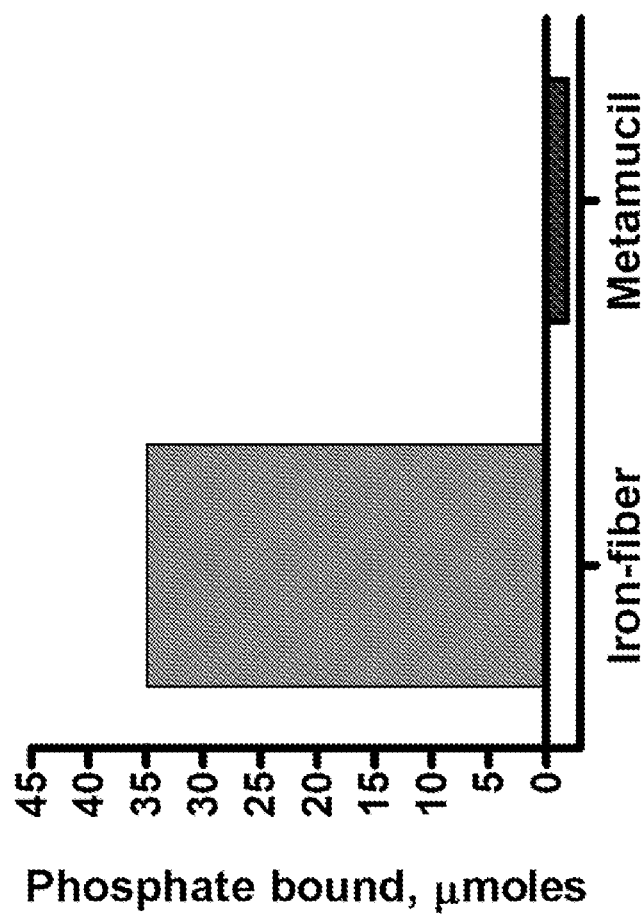
FIG. 13 is a graph illustrating a larger scale preparation of the fiber:$FeCl_3$ at 1:1 composition on phosphate-binding (vs. Metamucil as control).

Determined the phosphate level in the supernatants using the phosphate colorimetric assay (Catalog #K410-500 from Biovision). FIG. 13 shows the comparison between the iron-fiber composition and metamucil on adsorbing phosphate.

Example 10

Took 49 g of the dried fiber:$FeCl_3$=1:1 composition from Example 9. Mixed the composition with 490 g normal rat chow and 3.23 g $KH_2PO_4$+1.67 g $K_2HPO_4$. Ground the mixture until powdery.

As a control, took 49 g of the dried fiber alone composition (no iron during treatment). Mixed the composition with 490 g normal rat chow and 3.23 g $KH_2PO_4$+1.67 g $K_2HPO_4$. Ground the mixture until powdery.

Male, Sprague Dawley, rats were placed in metabolic cages with 1 rat per cage. Urine samples were collected for 24 hrs. Blood samples were collected from each rat for serum preparation. The rats were then placed in normal cages. Some rats were provided with the powder rat chow containing fiber alone and $KH_2PO_4$+$K_2HPO_4$. The other rats were provided with the powder rat chow containing the iron-fiber composition and $KH_2PO_4$+$K_2HPO_4$.

After four days, the rats were placed in metabolic cages with 1 rat per cage. Urine samples were collected for 24 hrs. Blood samples were collected from each rat to prepare serum. The phosphorus/phosphate level was determined in each urine and serum samples. Each group had at least 5 rats.

The serum phosphate was elevated in the rats treated with fiber alone, but not in the rats treated with iron-fiber (FIG. 14A). FIG. 14B shows the urinary phosphate concentration per 24-hr period in the rats fed the fiber alone composition vs. that in the rats fed the iron-fiber composition. FIG. 15 shows the physical appearance of the feces samples collected from rats treated with fiber alone vs. iron-fiber.

There was no significant difference in the amount of food consumed by the two groups of rats during the treatment.

Example 11

Mixed 5 g $Fe_4O_2P_6$ (Sigma p6526) in 30 ml water. Adjusted pH by adding HCl (concentrated) until pH at 1. Added 0.5 g fiber. Incubated the mixture for 2 hrs at room temperature with shaking. Added NaOH to neutralize. Mixed and incubated at room temperature for at least 1 hr with shaking. Washed with water until the supernatant was clear.

Took 0.94 g of the wet material. Added 0.5 ml of D-PBS and incubated briefly, mixed well, centrifuged and collected the supernatant.

Repeated the above process for 5 more times.

Determined the phosphate level in the supernatants using the phosphate colorimetric assay (Catalog #K410-500 from Biovision).

Figure 16:
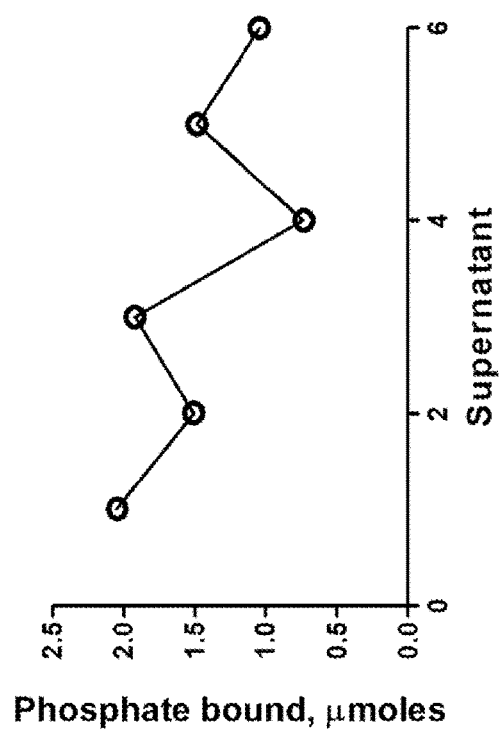
FIG. 16 is a graph illustrating a preparation of the iron-fiber (prepared from $Fe_4O_2P_6$) at 1:10 composition on phosphate binding.

FIG. 16 shows the effect of the iron:fiber composition on adsorbing phosphate; phosphate adsorbed in the 6 supernatants was 9 μmol/g of wet material.

Example 12

The Fiber:$FeCl_3$ composition from Example 9 was sputter coated with Platinum/Palladium and mounted on Aluminum stubs, and examined under Hitachi S3000N Variable Pressure SEM (Scanning Electron Microscope).

Figures 17A, 17B, 17C:
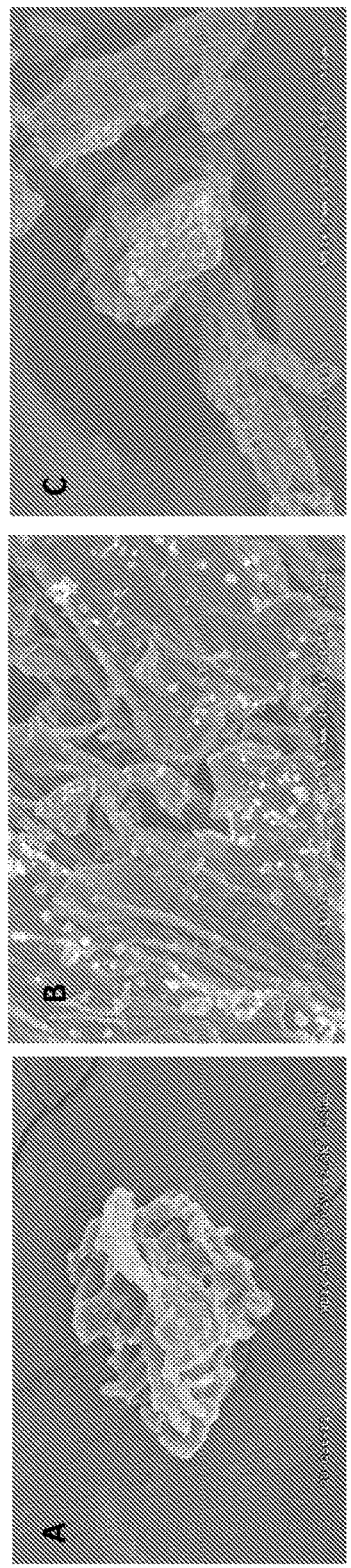
FIG. 17 is a graph illustrating the SEM pictures at different magnifications of the fiber:$FeCl_3$ at 1:1 composition. A: X2k, 20 µm. B: X1.5k, 20 µm. C: X700, 50 µm

FIG. 17 shows the SEM picture of the iron-fiber composition at different magnifications.

Example 13

Mixed 1 g fiber with 0, 0.2, 0.6, 2 and 5 g $FeCl_3$ in 20 ml water (pH ranging from 1 to 2.05 with $FeCl_3$ and pH=7.38 without $FeCl_3$). Incubated the mixture at room temperature for at least 1 hr. Washed with water until the supernatant was clear. Dried using a food dehydrator.

Removed 0.1 g of the dry composition from each sample, and mixed with 8 ml of water and 2 ml of a 20 mM phosphate solution (1.37 ml of 85% phosphoric acid, 3.18 g of sodium carbonate and 4.68 g of NaCl in 1 liter of water, adjusted pH to 7.0 with acetic acid). Incubated at room temperature for at least 24 hrs. Centrifuged and collected the supernatant for phosphate determination by the phosphate colorimetric assay (Catalog #K410-500 from Biovision).

FIG. 18 shows the final swell volume for each sample.

FIG. 19 shows the phosphate-binding property of the composition normalized by either per gram of dry composition, or per ml of the final volume after the incubation with the phosphate buffer (final swell volume).

Example 14

Mixed 0.1 g of the Fiber:$FeCl_3$ composition from Example 13 Tube#4 (fiber:iron at 1:2 ratio) with 2 ml, 4 ml, 6 ml, and 8 ml of the phosphate solution described in Example 13 (1.37 ml of 85% phosphoric acid, 3.18 g of sodium carbonate and 4.68 g of NaCl in 1 liter of water, pH=7.0). Each tube was added the diluting buffer (the same buffer without phosphoric acid) to a final volume of 8 ml/tube to result in 5 mM, 10 mM, 15 mM and 20 mM of final phosphate concentration. Incubated at room temperature for at least 24 hrs. Centrifuged and collected the supernatant for phosphate determination by the phosphate colorimetric assay (Catalog #K410-500 from Biovision).

Figure 20:
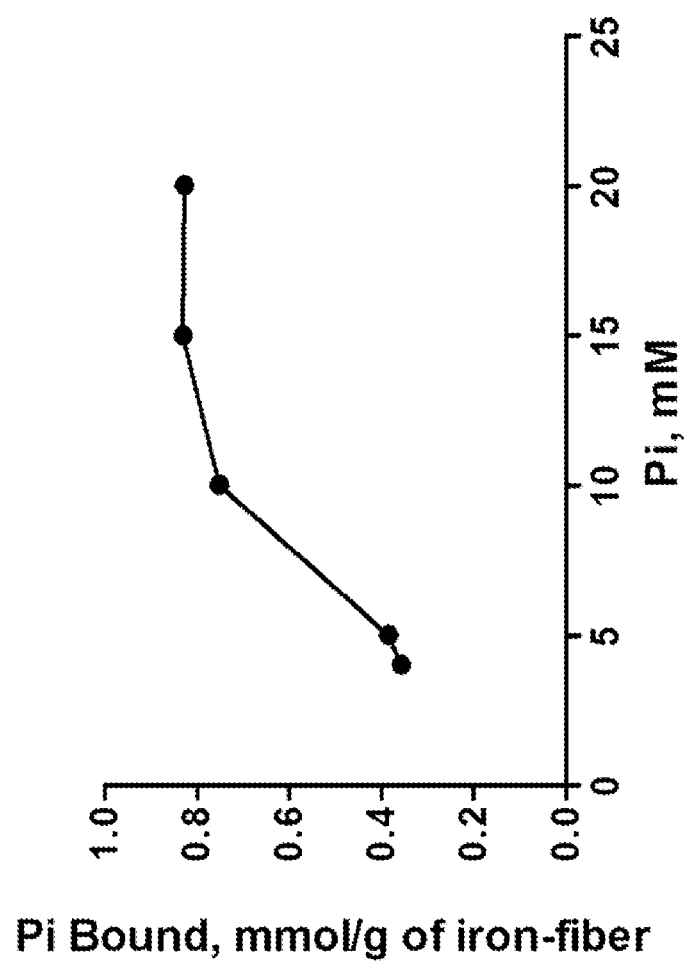
FIG. 20 is a graph illustrating the phosphate-binding property of the iron-fiber composition normalized by per gram of dry iron-fiber at different concentrations of phosphate. Pi: phosphate.

FIG. 20 shows the phosphate-binding property of the iron-fiber composition normalized by per gram of dry iron-fiber material at different concentrations of phosphate.

Example 15

Mixed 1 g fiber with 5 g $FeCl_3$ in 40 ml water (pH=1.44) per tube. Incubated the mixture at room temperature for at least 1 hr. Added different amounts of NaOH (12.5 N) so that the pH values changed to the following: Tube 1, pH=1.44; Tube 2, pH=1.72; Tube 3, pH=2.14; Tube 4, pH=3.1; Tube 5, pH=7; Tube 6, pH=9.43. Mixed and incubated at room temperature for at least 1 hr. Washed with water until the supernatant was clear. Dried using a food dehydrator.

Removed 0.1 g of the dry composition from each sample, and mixed with 8 ml of water and 2 ml of a 20 mM phosphate solution (1.37 ml of 85% phosphoric acid, 3.18 g of sodium carbonate and 4.68 g of NaCl in 1 liter of water, pH=7.0). Incubated at room temperature for at least 24 hrs. Centrifuged and collected the supernatant for phosphate determination using the phosphate colorimetric assay (Catalog #K410-500 from Biovision).

Figure 21:
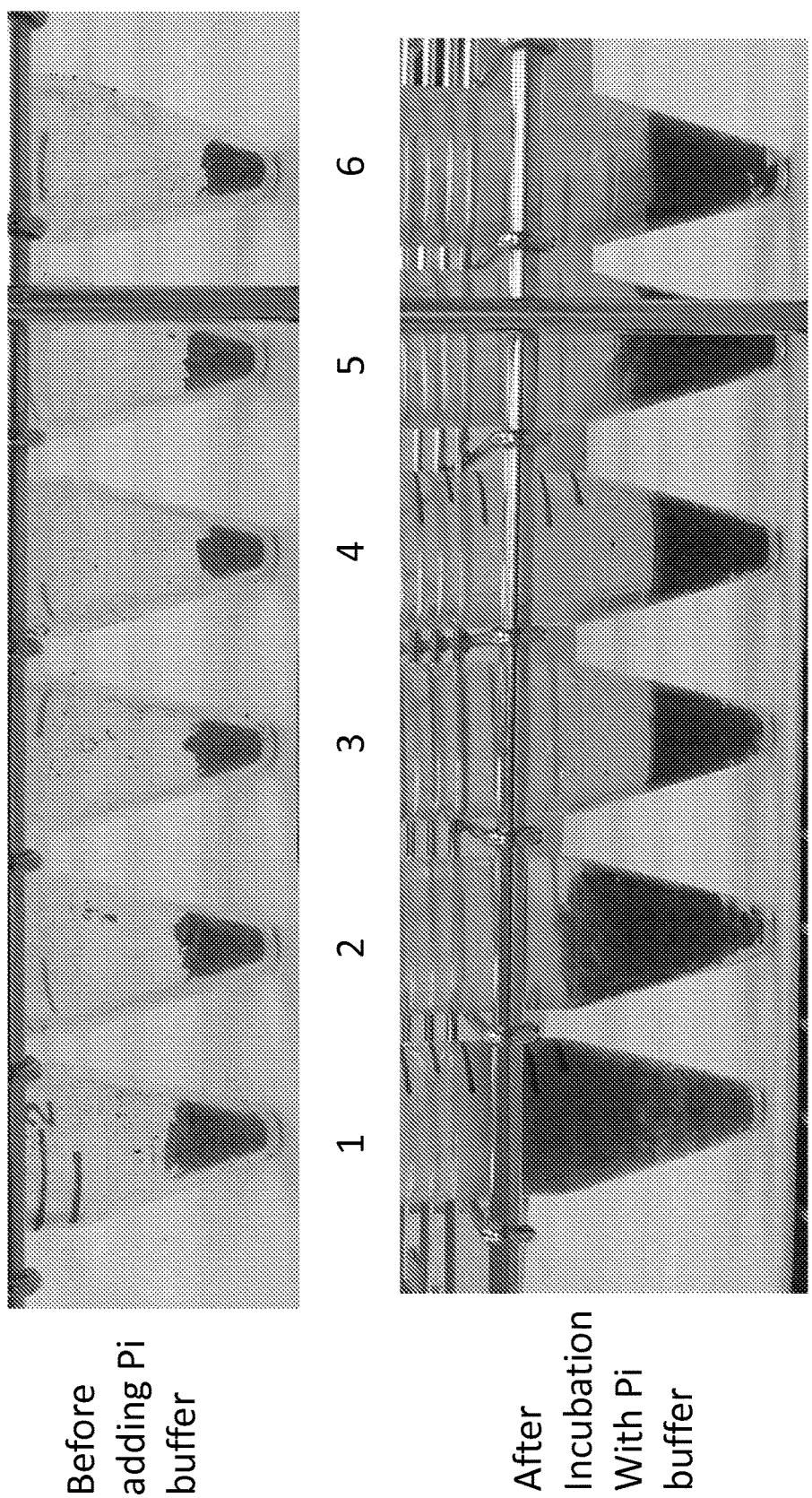
FIG. 21 illustrates the effect of different pH during the iron-fiber preparation on the physical appearance of the iron-fiber composition in the dry state and after the incubation with the phosphate buffer. Tube 1, pH=1.44; Tube 2, pH=1.72; Tube 3, pH=2.14; Tube 4, pH=3.1; Tube 5, pH=7; Tube 6, pH=9.43.

FIG. 21 shows the physical appearance of the iron-fiber composition at 0.1 gram in the dry state and after the incubation with the phosphate buffer.

Figure 22B:
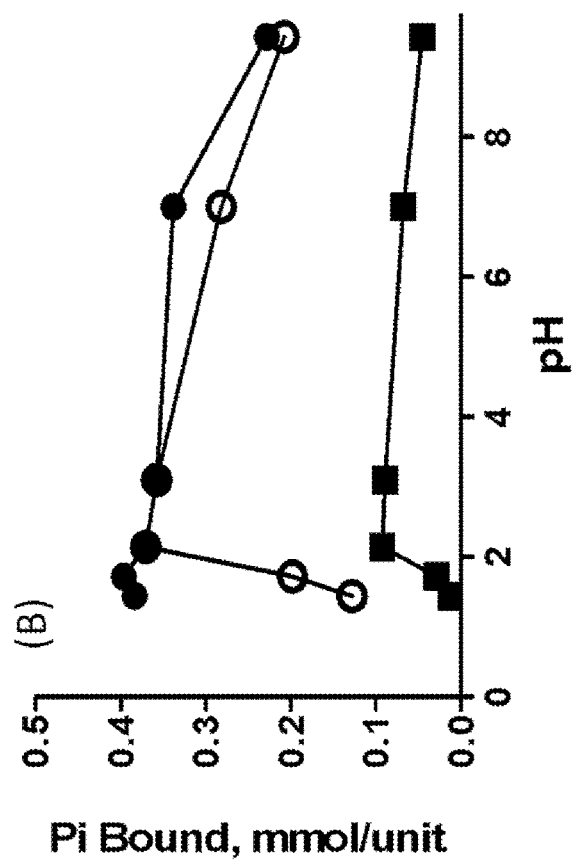
FIG. 22B illustrates the effect of adjusting pH during the preparation of the iron-fiber on phosphate binding. ●: normalized by per g of dry material. ○: normalized by per ml of the initial volume of the dry composition. ■, normalized by per ml of the final swell volume.
Figure 22A:
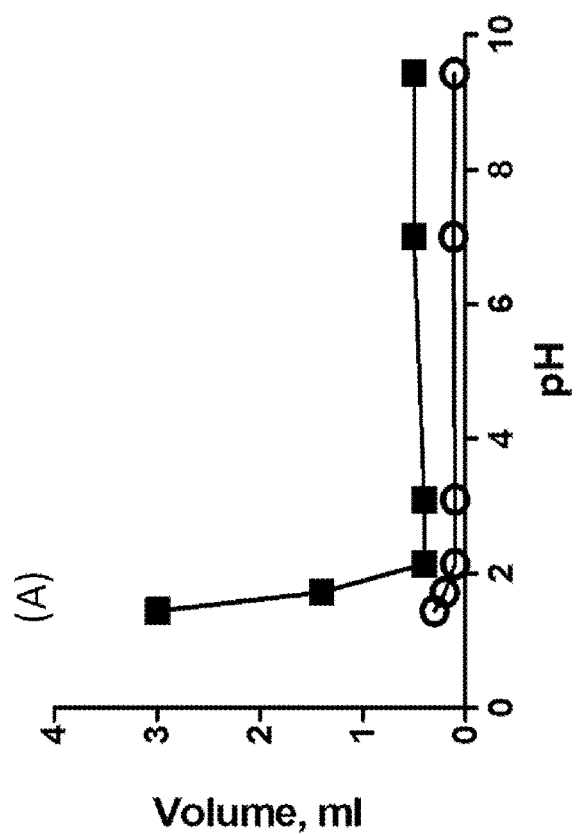
FIG. 22A illustrates the effect of adjusting pH during the preparation of the iron-fiber on the volume of the dry composition (initial volume, ○) and the final volume after the incubation with the phosphate buffer (final swell volume, ■).

FIG. 22A shows the volume of the dry composition (initial volume) in its loose form and the final volume after the incubation with the phosphate buffer (final swell volume).

FIG. 22B shows the phosphate-binding property of the iron-fiber composition normalized by either per gram of dry iron-fiber, or per ml of the dry iron-fiber (initial volume), or per ml of the final volume after the incubation with the phosphate buffer (final swell volume).

Adding 25 mM (final concentration) Tris buffer during the preparation of the iron-fiber composition made no significant differences in the results.

Example 16

Mixed 100 g dietary fiber with 100 g of $FeCl_3$ in 2.2 liter of water. Incubated the mixture at room temperature for at least 1 hr with shaking. Added 45.4 g NaOH (final pH=10). Mixed and incubated at room temperature for at least 1 hr with shaking. Washed with water until the supernatant was clear.

Dried the materials using a food dehydrator.

By inductively coupled plasma optical emission spectrometry (ICP-OES), the iron content in this dry iron-fiber composition was determined to be 15.3%.

Mixed 0.1 gram of the dried iron-fiber composition with the phosphate solution and the diluting buffer as described in Example 14 to a final volume of 20 ml/tube to result in 0 mM, 1 mM, 2.5 mM and 5 mM of final phosphate concentration. Incubated at room temperature for at least 24 hrs. Centrifuged and collected the supernatant for phosphate determination by the phosphate colorimetric assay (Catalog #K410-500 from Biovision).

As a control, samples containing 0.1 g of sevelamer in powder form in the place of the dried iron-fiber were prepared simultaneously.

Figure 23:
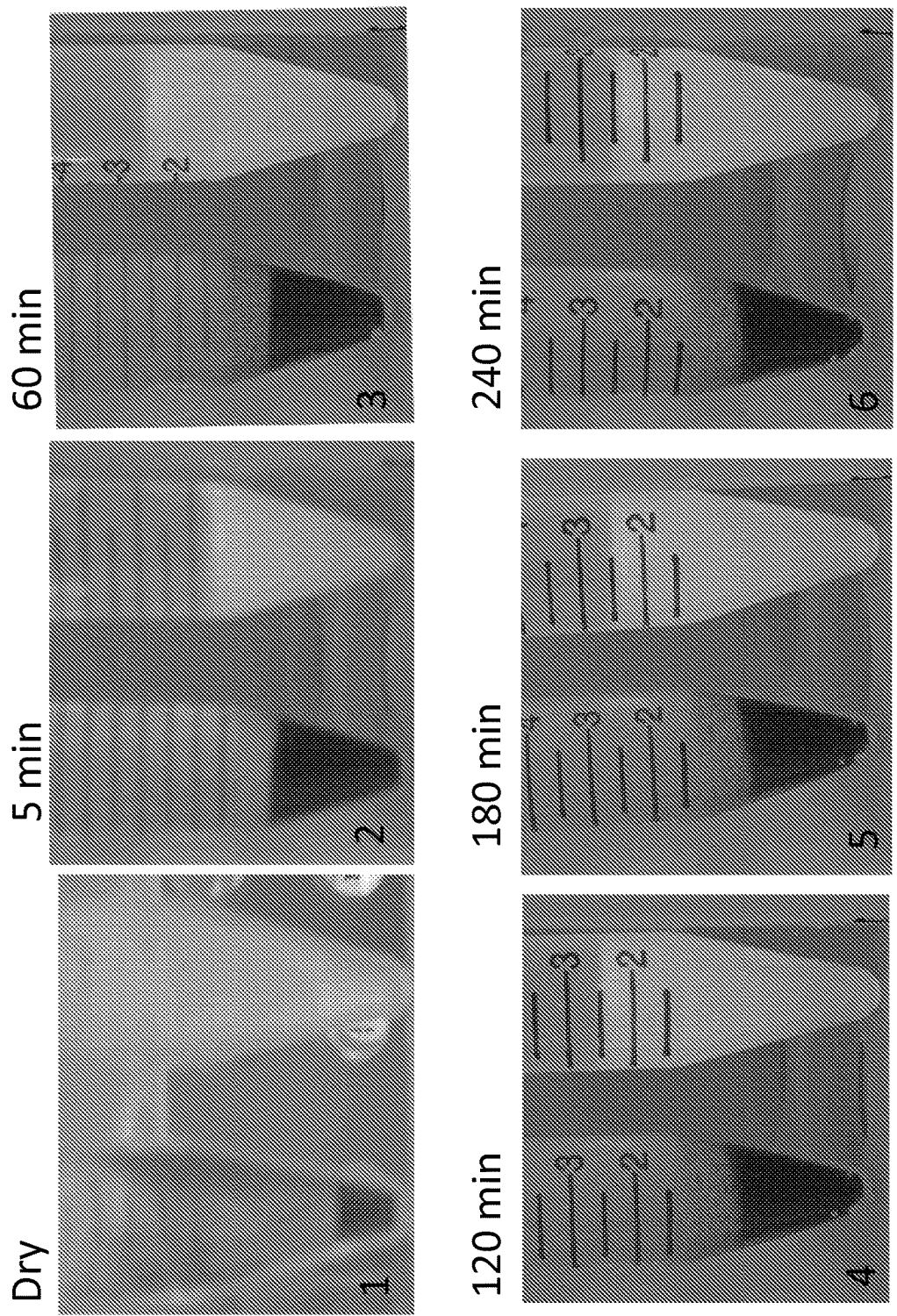
FIG. 23 shows the physical appearance of the iron-fiber composition (left) vs. sevelamer (sevelamer hydrochloride, right) at different time points after the addition of a phosphate (5 mM) buffer.

FIG. 23 shows the physical appearance of the iron-fiber composition vs. sevelamer at different time points after the addition of the phosphate buffer at 5 mM.

FIG. 24 shows the phosphate-binding property of the iron-fiber composition vs. that of sevelamer normalized by per gram of dry material or per ml of the final swell volume at different concentrations of phosphate.

Example 17

Prepared the phosphate solution and the diluting buffer as described in Example 14 to a final volume of 10 ml/tube at 10 mM of final phosphate concentration. Adjusted the pH to 1.59, 4.39, 7.1, 8.97, and 12.25.
Added 0.1 gram of the dried iron-fiber composition from Example 16. Incubated at room temperature for at least 24 hrs. Centrifuged and collected the supernatant for phosphate determination by the phosphate colorimetric assay (Catalog #K410-500 from Biovision).
FIG. 25 shows the phosphate-binding property at different pH of the iron-fiber composition normalized by per gram of dry iron-fiber.

Example 18

Figure 26:
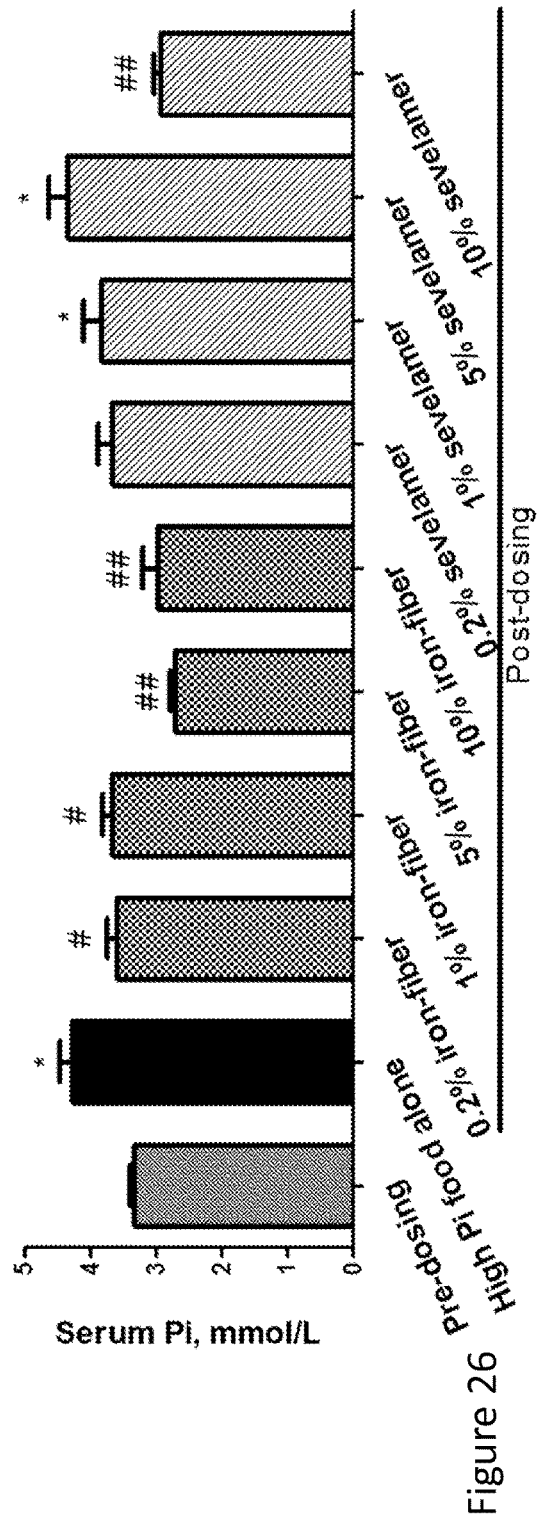
FIG. 26 illustrates the serum phosphate (Pi) levels in the rats fed the phosphate-enriched food containing iron-fiber or sevelamer. *$p<0.05$ vs. pre-dosing. #$p<0.05$, ##$p<0.01$ vs. High Pi food alone (no addition).
Figure 27:
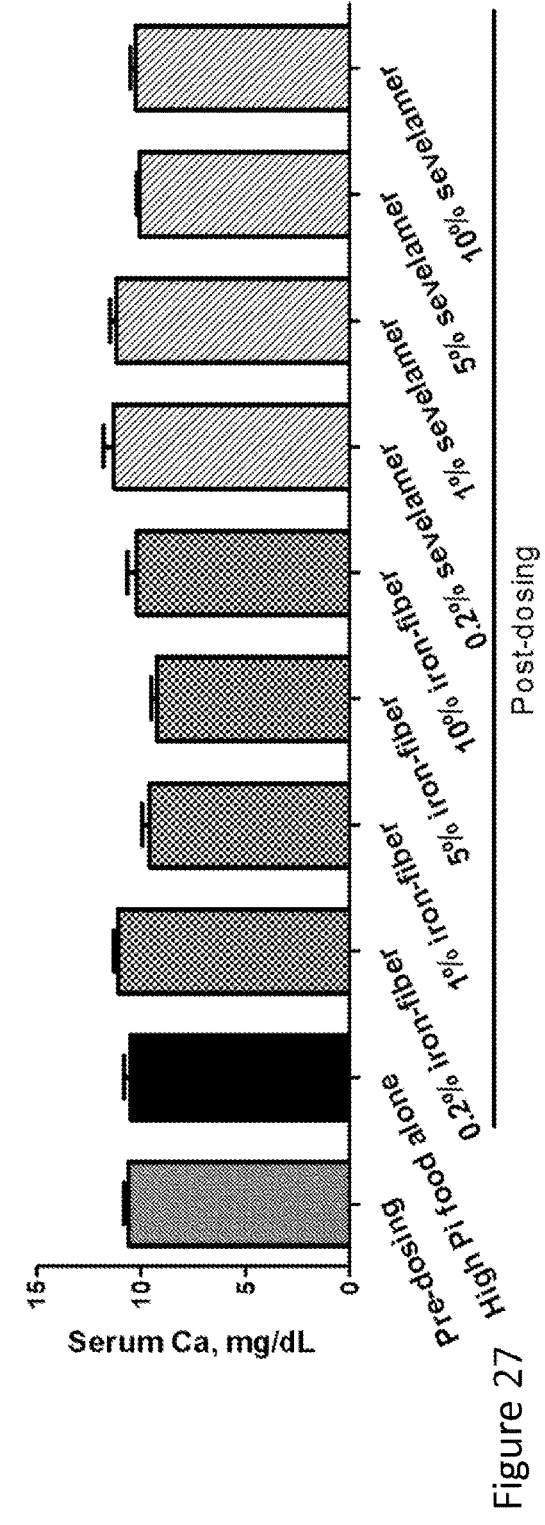
FIG. 27 illustrates the serum calcium levels in the rats fed the phosphate-enriched food containing iron-fiber or Sevelamer.
Figure 28:
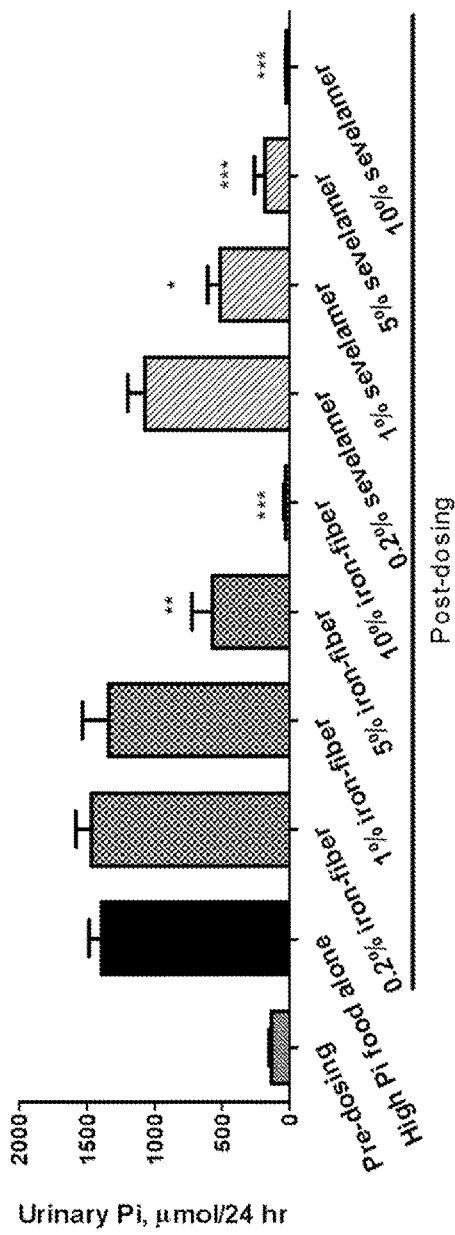
FIG. 28 illustrates the urinary phosphate levels (per 24-hr collecting period) in the rats fed the phosphate-enriched food containing iron-fiber or sevelamer. *$p<0.05$, $p<0.01$, *$p<0.001$ vs. High Pi food alone (no addition).
Figure 29:
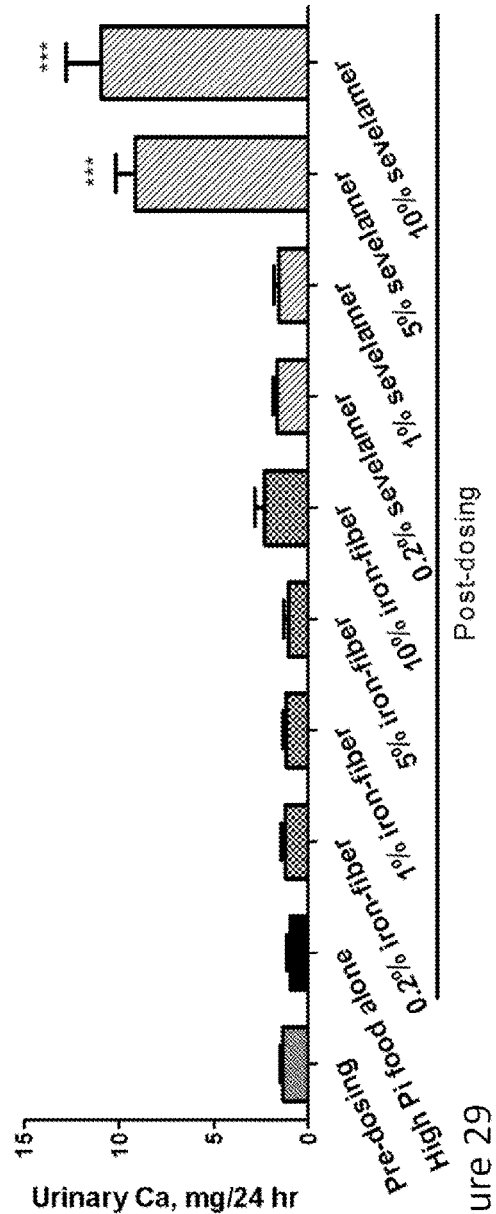
FIG. 29 illustrates the urinary calcium levels (per 24-hr collecting period) in the rats fed the phosphate-enriched food containing iron-fiber or Sevelamer. ***$p<0.001$ vs. High Pi food alone (no addition).
Figure 30:
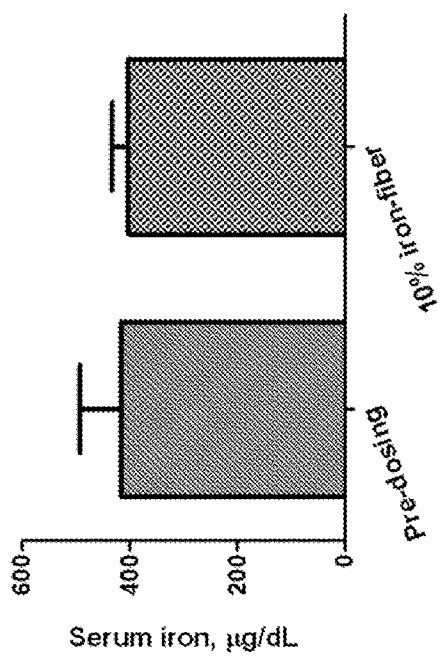
FIG. 30 shows the serum iron levels in the rats before treatment and after the iron-fiber treatment.

Took dried iron-fiber from Example 16. Mixed the composition with normal rat chow and $KH_2PO_4+K_2HPO_4$ as in Example 10 except that the amount of the iron-fiber was at 0.2-10% by weight of the total mixture. Ground the mixture until powdery.
As a control, prepared a mixture with sevelamer powder and normal rat chow and $KH_2PO_4+K_2HPO_4$ with the amount of sevelamer at 0.2-10% by weight of the total mixture. Ground the mixture until powdery.
Male, Sprague Dawley, rats were placed in metabolic cages with 1 rat per cage. Urine samples were collected for 24 hrs. Blood samples were collected from each rat for serum preparation.
Rats were fed with the diet containing high phosphates and different preparations as mentioned above.
After four days, the rats were placed in metabolic cages with 1 rat per cage. Urine samples were collected for 24 hrs. Blood samples were collected from each rat to prepare serum. The phosphorus/phosphate and calcium levels were determined in each urine and serum samples. The serum iron levels were also determined in some serum samples (QuantiChrom™ Iron Assay Kit by BioAssay System; catalog #DIFE-250).
FIG. 26 shows that the serum phosphate was significantly higher in the rats without treatment. Iron-fiber at 0.2-10% reduced serum phosphate in a dose dependent manner. Sevelamer at 10% also reduced serum phosphate.
No significant difference was observed in the serum calcium concentrations in the rats (FIG. 27).
FIG. 28 shows the urinary phosphate concentration per 24-hr collection period in the rats fed the food containing iron-fiber and sevelamer.
FIG. 29 shows the urinary calcium concentration per 24-hr collection period in the rats fed the food containing iron-fiber and sevelamer.
FIG. 30 shows the serum iron levels in the rats before treatment and after the iron-fiber (10%) treatment. There was no significant difference in the serum iron levels.

Example 19

Figure 31A:
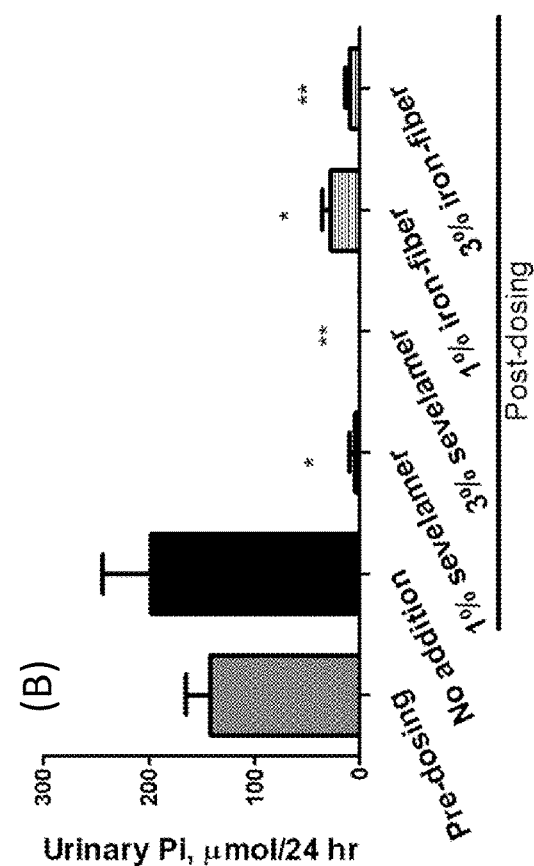
FIGS. 31A&B illustrate the serum and urine (per 24-hr collecting period) phosphate levels in the rats fed normal food, or food containing iron-fiber or sevelamer. *$p<0.05$, **$p<0.01$ (vs. pre-dosing).
Figure 31B:
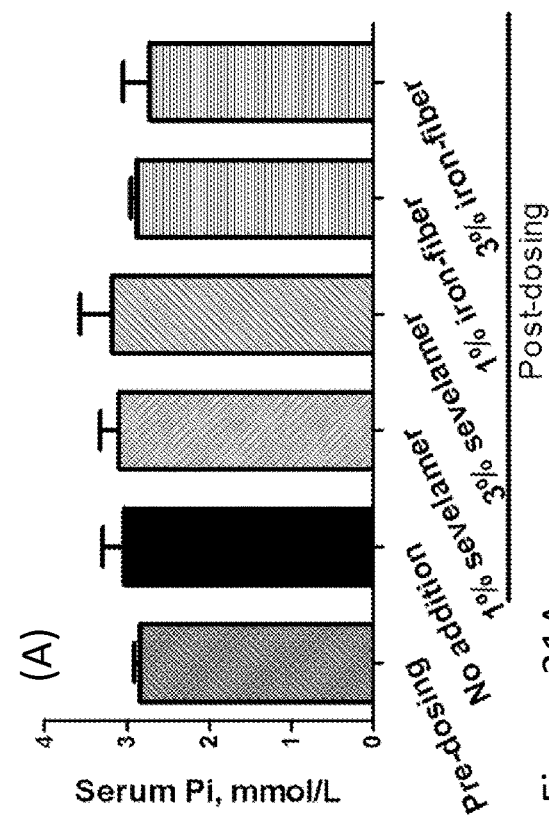
Figure 32A:
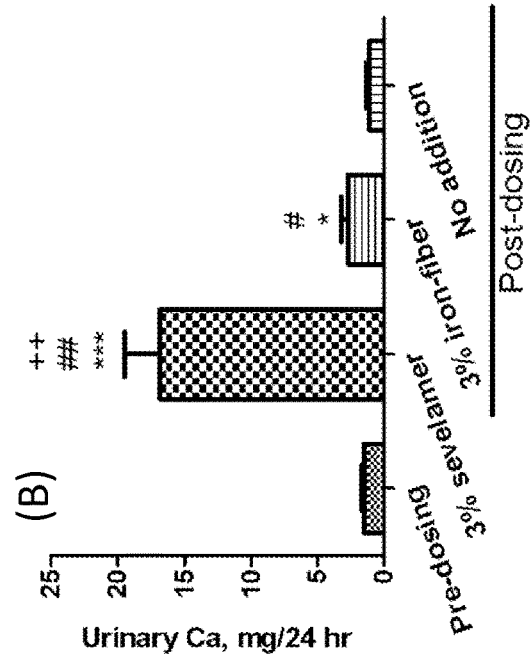
FIG. 32 illustrate the serum calcium, urinary calcium and PTH levels in the rats fed normal food, or food containing iron-fiber or sevelamer. *$p<0.05$, ***$p<0.001$ vs. pre-dosing. #$p<0.05$, ##$p<0.01$, ###$p<0.001$ vs. no addition. +$p<0.05$, ++$p<0.01$ vs. iron-fiber.
Figure 32B:
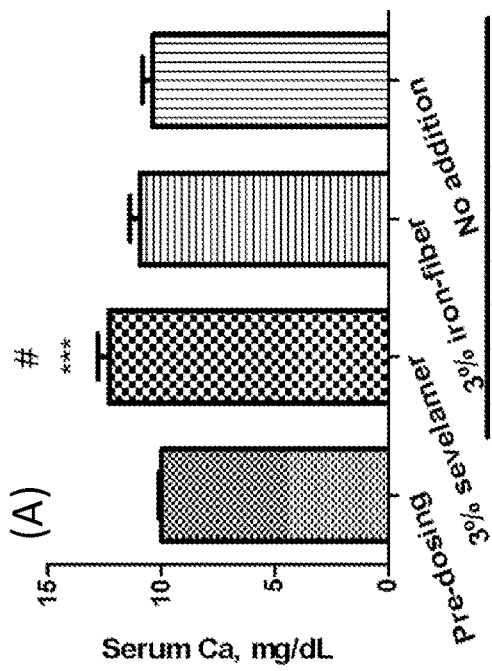
Figure 32C:
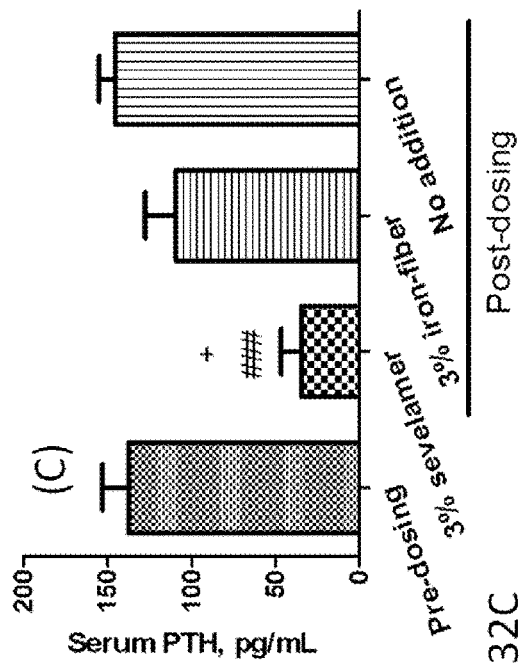
Figure 33B:
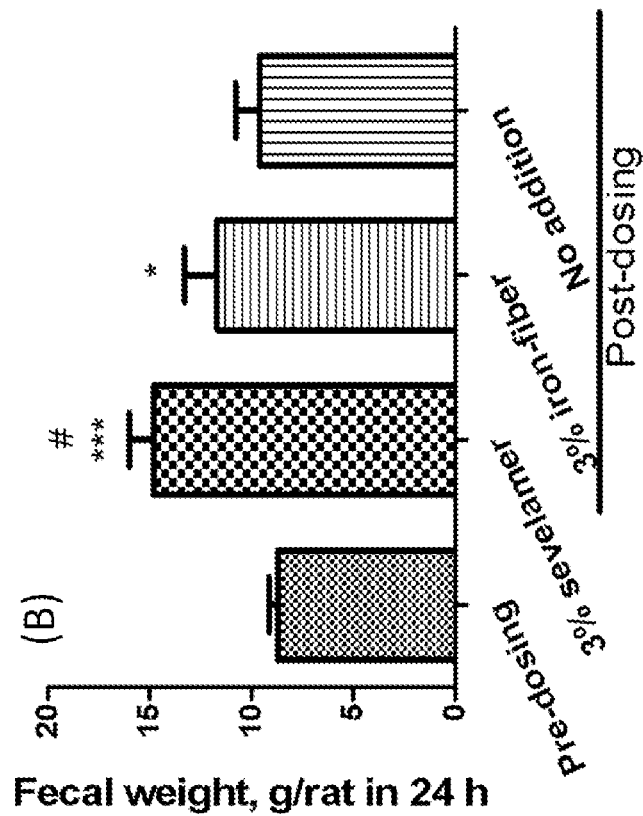
FIGS. 33A&B illustrate the feces weight and urine volume (per 24-hr period) in the rats fed normal food, food containing iron-fiber or sevelamer. *$p<0.05$, *$p<0.001$ vs. pre-dosing. #$p<0.05$ vs. no addition FIGS. 34A&B illustrate the water and food consumption in the rats fed normal food, food containing iron-fiber or sevelamer. $p<0.01$ vs. "No Addition". The water and food consumption was measured daily for 6 days and normalized by the rat body weight.
Figure 33A:
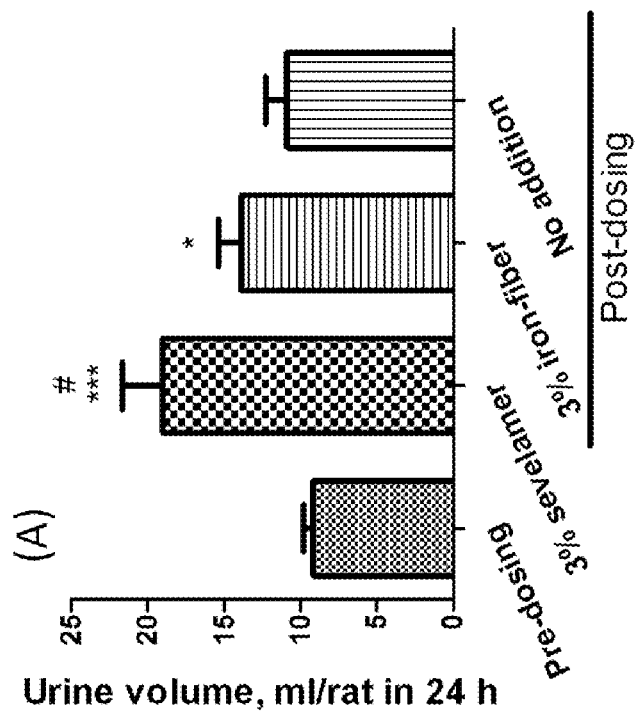
Figure 34B:
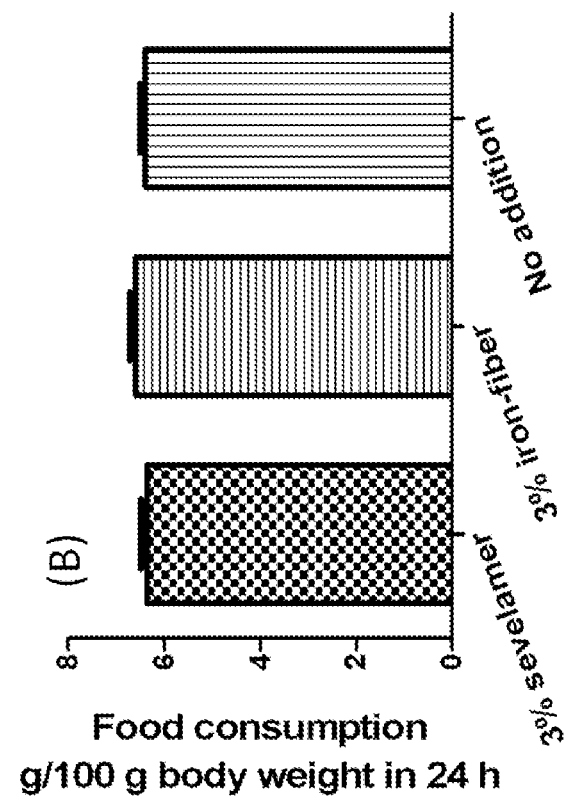
Figure 34A:
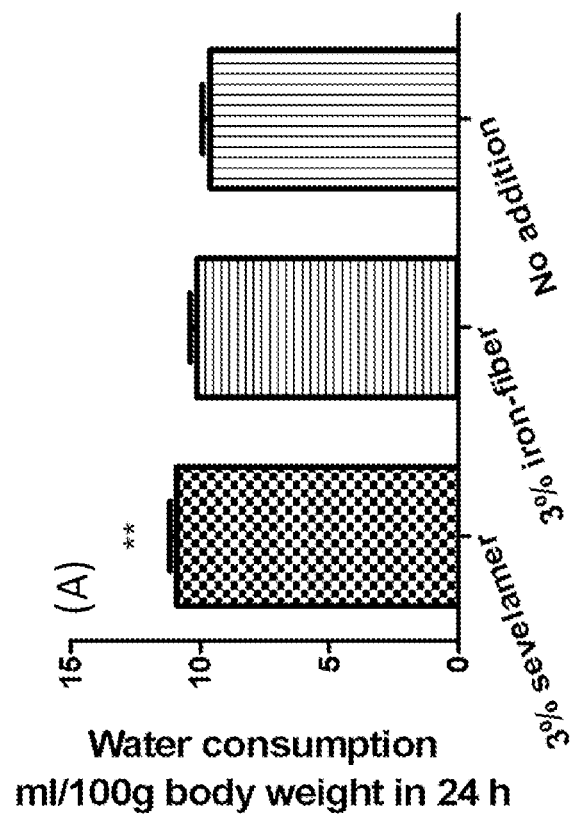
Figures 35, 36:
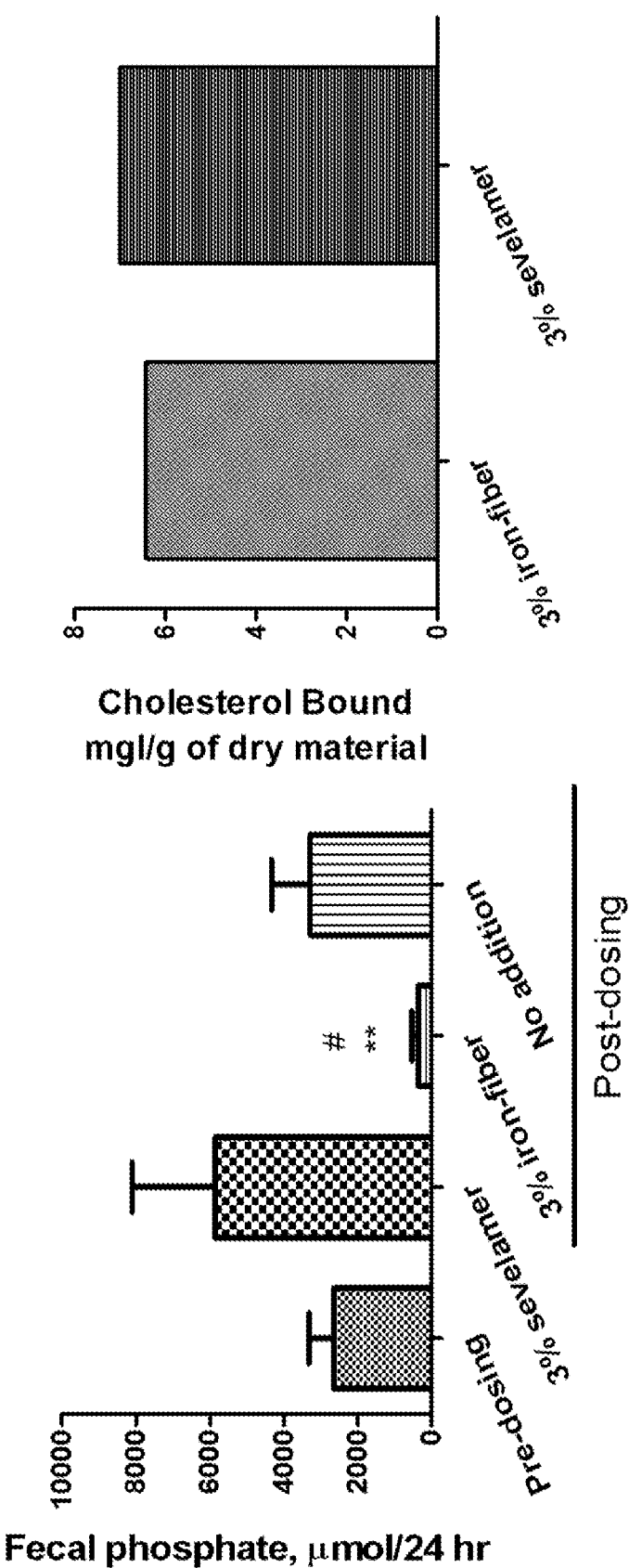
FIG. 35 illustrates the phosphate level in the fecal ash. **$p<0.01$ vs. pre-dosing. #$p<0.05$ vs. No addition (plain food)
FIG. 36 is a graph illustrating the cholesterol-binding property of the iron-fiber composition vs. sevelamer normalized by per gram of dry material.

Took dried iron-fiber from Example 16. Mixed the composition with normal rat chow (containing 1% calcium and 0.7% phosphate) so that the iron-fiber was at 1 and 3% by weight of the total mixture. Ground the mixture until powdery.
As a control, prepared a mixture with sevelamer powder and normal rat chow with the amount of sevelamer at 1 and 3% by weight of the total mixture. Ground the mixture until powdery.
Male, Sprague Dawley, rats were placed in metabolic cages with 1 rat per cage. Urine samples were collected for 24 hrs. Blood samples were collected from each rat for serum preparation. Rats were fed with normal diet (containing 1% calcium and 0.7% phosphorus in powder form) and the iron-fiber material or sevelamer. After five days, the rats were placed in metabolic cages with 1 rat per cage. Urine samples were collected for 24 hrs. Blood samples were collected from each rat to prepare serum. The phosphorus/phosphate and calcium levels were determined in each urine and serum samples. Each group had at least 6 rats.
FIG. 31A shows that the serum phosphate (Pi) was similar across the different groups. FIG. 31B shows the urinary phosphate level per 24-hr collection period in the rats. Iron-fiber and sevelamer at 1 and 3% significantly decreased the urine phosphate level.
FIGS. 32A, B and C shows the serum calcium, the urinary calcium and PTH levels in the rats fed the food containing iron-fiber and sevelamer. Iron-fiber had no significant effect on serum calcium and PTH, but sevelamer significantly increased serum and urinary calcium and decreased serum PTH.
FIGS. 33A&B shows the feces weight and urine volume per 24-hr period in the different treatment groups. FIGS. 34A&B shows the water and food consumption in the different treatment groups.
Feces samples collected per 24-hr period were ashed at 800° C. for 45 minutes. Weighed 0.1 g of ash from each sample, extracted with 1 ml water by vortexing and shaking at room temperature for at least 60 min Centrifuged and collected supernatant for phosphate determination. FIG. 35 shows the total phosphate level in the feces collected during the 24-hr period. More phosphate was present in the feces from the sevelamer group (vs. no addition). However, the phosphate detected in the iron-fiber treated group was significantly lower than that in the control group (pre-dosing or no addition), indicating that the phosphate remained bound tightly to iron-fiber in the fecal ash and could not be extracted by water.

Example 20

Took 0.1 gram of sevelamer or 0.1 gram of the dried iron-fiber composition from Example 16 and mixed with 10 ml of a 20 mM phosphate solution (1.37 ml of 85% phosphoric acid, 3.18 g of sodium carbonate and 4.68 g of NaCl in 1 liter of water, pH=7.0). Incubated at room temperature for at least 24 hrs. Centrifuged and removed 8.6 ml of the supernatant.
Prepared a stock solution of 6 mg cholesterol (water-soluble cholesterol, Sigma C4951) in 1 ml water. Added 0.5 ml (3 mg) to the tubes containing sevelamer or the iron-fiber composition. Incubated at room temperature for at least 30 min with gentle shaking. Removed the supernatant for determining cholesterol using the Stanbio Liquicolor cholesterol assay kit (Catalog #1010-430)
FIG. 36 shows the cholesterol-binding property normalized by per gram of dry material. The iron-fiber composition and sevelamer exhibited similar cholesterol binding property.

Example 21

Mixed 1 g fiber with 5 g $FeCl_3$ in 40 ml water (pH=1.44) per tube. Incubated the mixture at room temperature, or 37° C., or 55° C. for at least 1 hr. Added NaOH (12.5 N) to neutralize. Washed with water until the supernatant was clear and pH was 7. Dried using a food dehydrator.

Removed 0.1 g of the dry composition from each sample, and mixed with 5 ml of a 20 mM phosphate solution (1.37 ml of 85% phosphoric acid, 3.18 g of sodium carbonate and 4.68 g of NaCl in 1 liter of water, pH=7.0). Incubated at room temperature for at least 24 hrs. Centrifuged and collected the supernatant for phosphate determination using the phosphate colorimetric assay (Catalog #K410-500 from Biovision).

FIG. 37A shows the final volume of the composition after the incubation with the phosphate buffer (final swell volume). FIG. 37B shows the phosphate-binding property of the iron-fiber composition normalized by per gram of dry iron-fiber. FIG. 37C shows the phosphate-binding property of the iron-fiber composition normalized by per ml of the final volume after the incubation with the phosphate buffer (final swell volume). The data show that higher temperature during the preparation of the composition results in a smaller swell volume of the composition.

Example 22

Mixed 1 g fiber with 0, 0.2, 0.6, 2 and 5 g $FeCl_3$ in 40 ml water. Incubated the mixture at room temperature, or 37° C., or 55° C. for at least 1 hr. Added NaOH (12.5 N) to neutralize. Washed with water until the supernatant was clear and pH was 7. Dried using a food dehydrator.

By inductively coupled plasma optical emission spectrometry (ICP-OES), the iron content in the dry iron-fiber composition prepared from incubating 1 g fiber with 5 g $FeCl_3$ at 55° C. was determined to be 29.3%.

Removed 0.1 g of the dry composition from each sample, and mixed with 5 ml of a 20 mM phosphate solution (1.37 ml of 85% phosphoric acid, 3.18 g of sodium carbonate and 4.68 g of NaCl in 1 liter of water, pH=7.0). Incubated at room temperature for at least 24 hrs. Centrifuged and collected the supernatant for phosphate determination using the phosphate colorimetric assay (Catalog #K410-500 from Biovision).

Figure 38B:
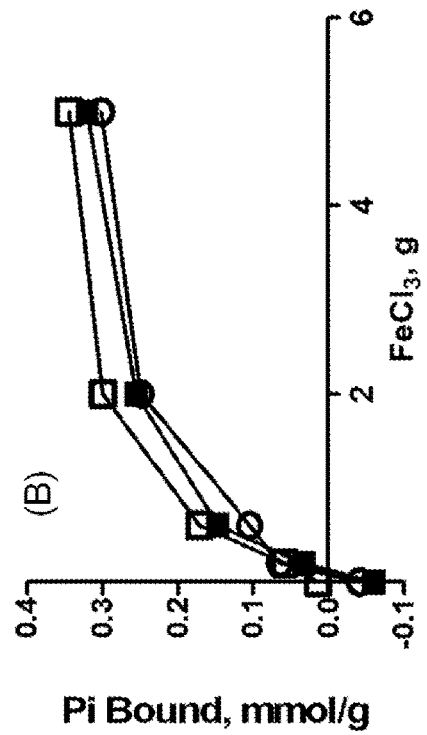
FIG. 38 illustrates the effect of incubation temperature and different amounts of $FeCl_3$ during the preparation of the composition on (A) the final swell volume (after the incubation with the phosphate buffer), (B) phosphate-binding normalized by per gram of dry iron-fiber, and (C) phosphate-binding normalized by per ml of the final swell volume. ■: room temperature. ○: 37° C. □: 55° C.
Figure 38C:
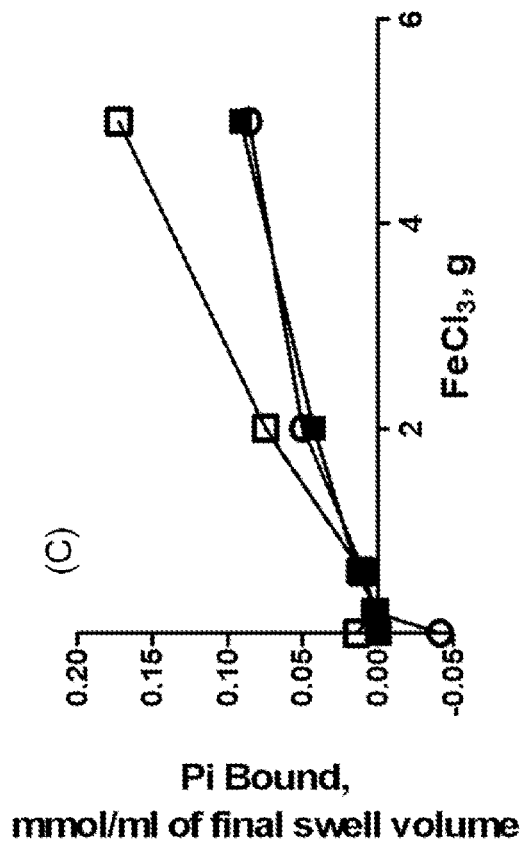
Figure 38A:
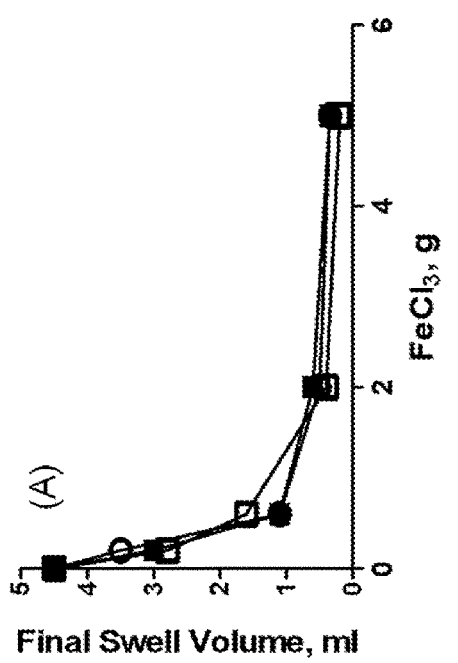

FIG. 38A shows the final volume of the composition after the incubation with the phosphate buffer (final swell volume). FIG. 38B shows the phosphate-binding property of the iron-fiber composition normalized by per gram of dry iron-fiber. FIG. 38C shows the phosphate-binding property of the iron-fiber composition normalized by per ml of the final volume after the incubation with the phosphate buffer (final swell volume). The data show that the phosphate binding capacity was depending on the iron-fiber ratio.

Example 23

Took 0.1 gram the dry iron-fiber composition from Example 22 where the composition was prepared from incubating 1 g fiber with 5 g $FeCl_3$ at 55° C. Added 5 ml of water. Incubated at 37° C.

As a control, 0.1 g of sevelamer in powder form in the place of the dried iron-fiber was prepared simultaneously.

Figure 39:
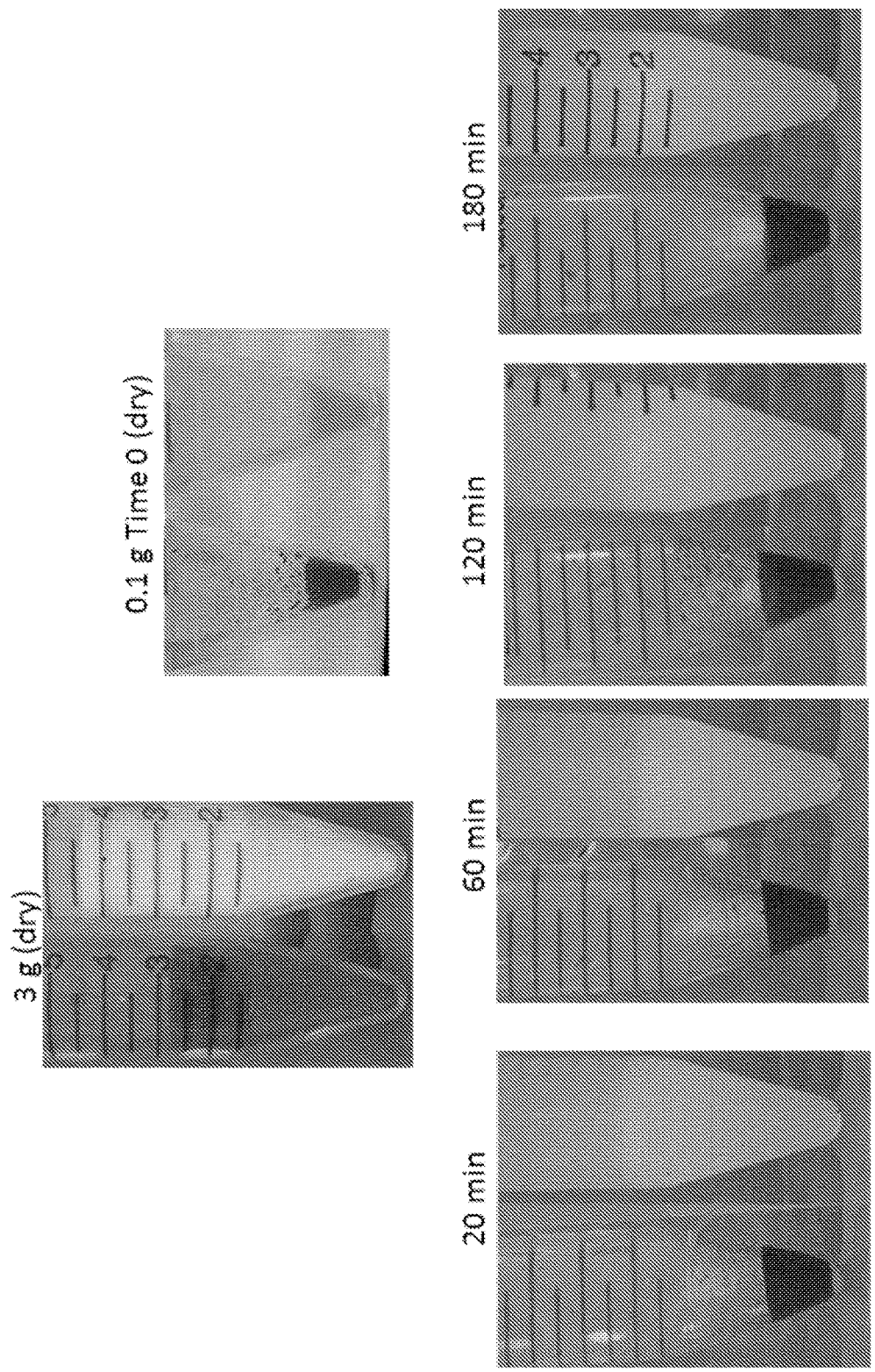
FIG. 39 shows the physical appearance of the iron-fiber composition (left) vs. sevelamer (right) at different time points after incubating with water or simulated gastric fluid at 37° C.

FIG. 39 shows the physical appearance of the iron-fiber composition vs. sevelamer at different time points during the incubation at 37° C.

Similar results were observed when simulated gastric fluid (0.2% (w/v) NaCl, 0.7% (v/v) HCl, without pepsin) instead of water was used.

The volume ($cm^3$) of the iron-fiber composition vs. sevelamer at different time points (20 min-180 min): 0.2 vs. 2.0 $cm^3$. Large swelling volume is associated with GI discomfort. To show the volume at Time 0 more clearly, the volume of iron-fiber or sevelamer at 3 g/sample was also determined (2.7 vs. 4.4 $cm^3$).

Took 0.1 gram sevelamer or the dry iron-fiber composition from Example 22 where the composition was prepared from incubating 1 g fiber with 5 g $FeCl_3$ at 55° C. Added 5 ml of a 20 mM phosphate solution (1.37 ml of 85% phosphoric acid, 3.18 g of sodium carbonate and 4.68 g of NaCl in 1 liter of water, pH=7.0). Incubated at room temperature for at least 24 hrs. Centrifuged and collected the supernatant for phosphate determination using the phosphate colorimetric assay (Catalog #K410-500 from Biovision).

The phosphate-binding property of each sample normalized by per gram of dry iron-fiber was: 0.39 mmol/g of sevelamer vs. 0.35 mmol/g of iron-fiber. The phosphate-binding property of each sample normalized by per ml of final swell volume was: 0.016 mmol/ml of sevelamer vs. 0.172 mmol/ml of iron-fiber.

Example 24

Mixed 5 g fiber with 10 g $FeCl_3$ in 40 ml water. Incubated the mixture at 55° C. for at least 1 hr. Added NaOH (12.5 N) to neutralize (pH=7). Washed with water until the supernatant was clear and pH was 7. Dried using a food dehydrator.

Removed 0.1 g of the dry composition, and mixed with 5 ml of a 20 mM phosphate solution (1.37 ml of 85% phosphoric acid, 3.18 g of sodium carbonate and 4.68 g of NaCl in 1 liter of water, pH=7.0). Incubated at room temperature for at least 24 hrs. Centrifuged and collected the supernatant for phosphate determination using the phosphate colorimetric assay (Catalog #K410-500 from Biovision). The phosphate-binding property of normalized by per gram of dry iron-fiber was 0.59 mmol/g.

By inductively coupled plasma optical emission spectrometry (ICP-OES), the iron content in the dry iron-fiber composition was determined to be 24.5%.

Took 0.1 gram the dry iron-fiber composition. Added 5 ml of simulated gastric fluid (0.2% (w/v) NaCl, 0.7% (v/v) HCl, without pepsin). Incubated at 37° C.

As a control, 0.1 g of unprocessed fiber was treated simultaneously.

Figure 40:
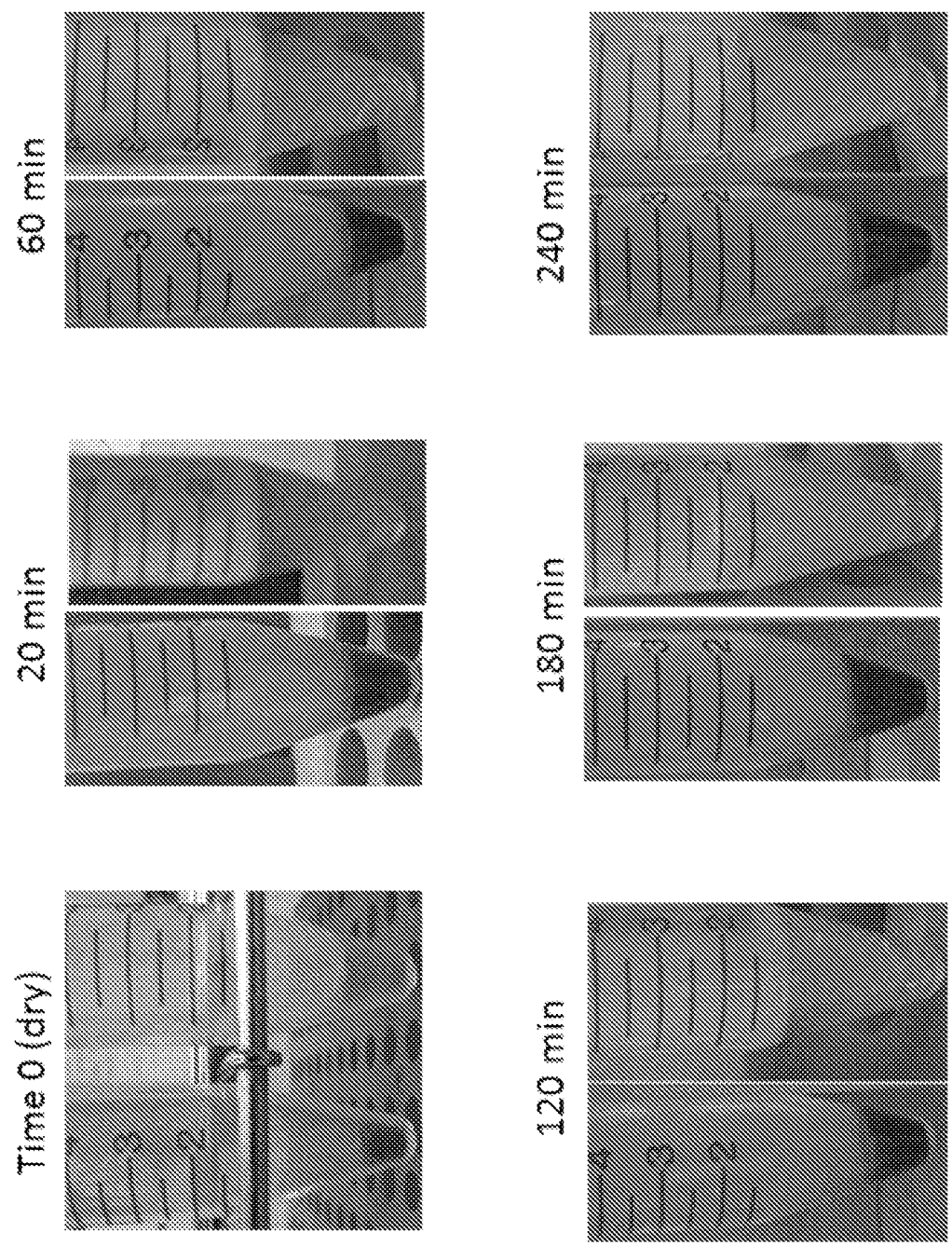
FIG. 40 shows the physical appearance of the iron-fiber composition (left) vs. unprocessed fiber (right) at different time points after incubating with simulated gastric fluid at 37° C.

FIG. 40 shows the physical appearance of the iron-fiber composition vs. unprocessed fiber at different time points during the incubation at 37° C.

The volume ($cm^3$) of the iron-fiber composition vs. unprocessed fiber at different time points were: 20 min, 0.2 vs. 1.0 $cm^3$; 60 min, 0.2 vs. 1.1 $cm^3$; 120 min, 0.2 vs. 1.2 $cm^3$; 180 min, 0.2 vs. 1.9 $cm^3$, 240 min, 0.2 vs. 1.9 $cm^3$.

Example 25

The iron-fiber sample from Example 24 was analyzed further by the XPS (X-ray Photoelectron Spectroscopy). XPS experiments were performed using the Kratos Axis-165 instrument. Samples were irradiated by a monochromatic Al—$K_\alpha$ X-ray source (15 kV, 10 mA) at an angle of 30 degrees from the sample surface. Photoelectrons were detected by 8 channeltrons of the concentric hemispherical analyzer over an area of 700×300 microns, with a spectrometer take-off angle of zero. The detection was achieved using the constant analyzer energy (CAE) mode.

Survey scans were acquired with a pass-energy of 160 eV, 1.0 eV step-size and 100 msec dwell time; while narrow scans were acquired with a pass-energy of 20 eV, 0.1 eV step-size and 200 msec. All scans were performed with the charge-neutralization system running Charge-referencing were done with the adventitious carbon peak position of 284.8 eV. The XPS analysis chamber base-Pressure was better than 2E-10 Torr, while working-Pressure was better than 3E-9 Torr.

Figure 41A:
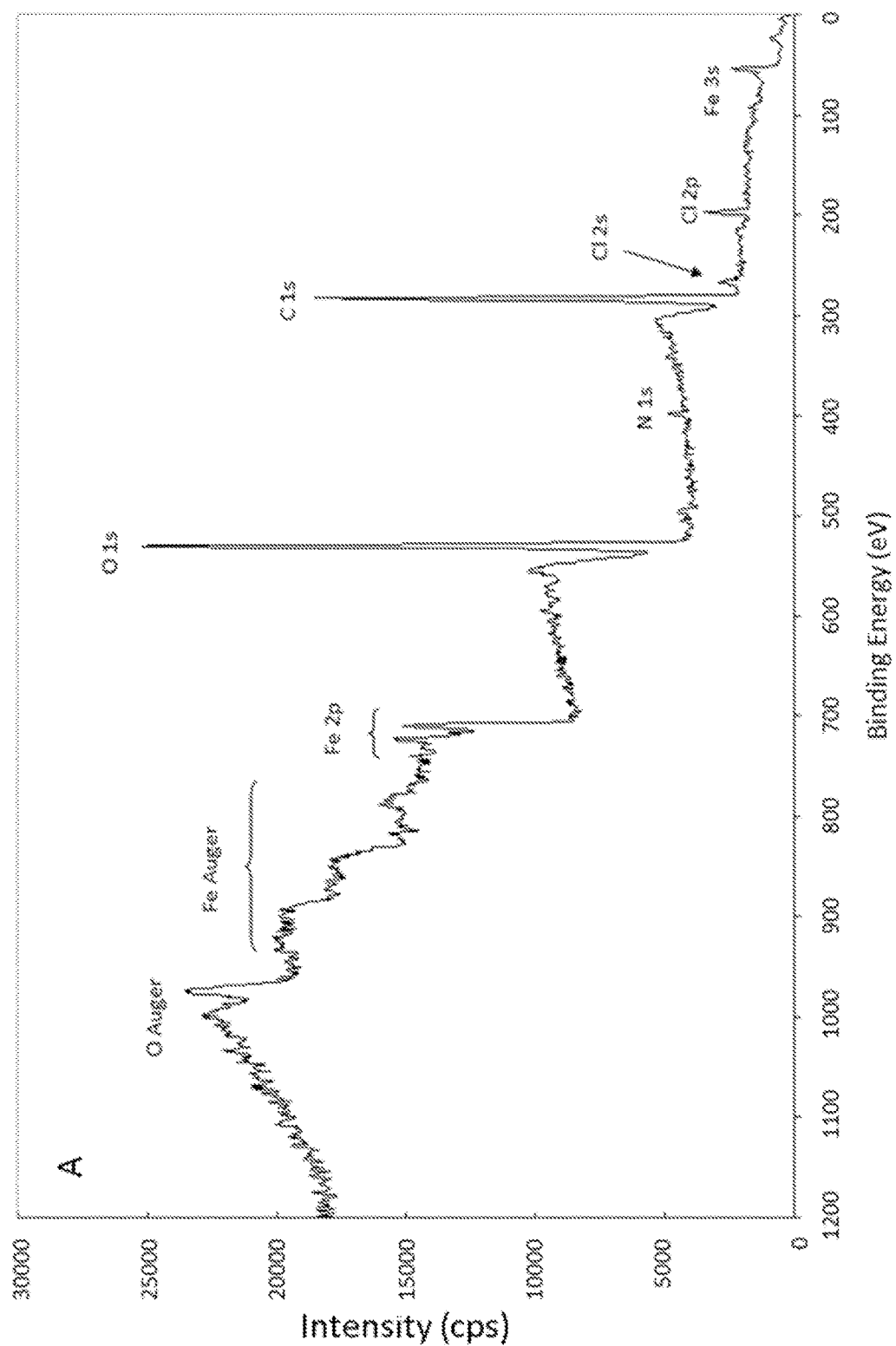
FIG. 41 shows (A) the survey, (B) C 1s and (C) Fe 2p spectrum from XPS analysis of an iron-fiber composition prepared from dietary fiber and $FeCl_3$.

FIG. 41A shows the survey spectrum from the XPS analysis. The semi-quantitation data are listed in the table.

| Peak | Position BE (eV) | FWHM (eV) | Raw Area (CPS) | RSF | Atomic Mass | Atomic Conc, % | Mass Conc, % |
|---|---|---|---|---|---|---|---|
| Fe 2p | 710.000 | 6.100 | 77697.5 | 2.957 | 55.846 | 6.70 | 22.67 |
| Cl 2p | 197.000 | 3.481 | 5920.0 | 0.891 | 35.460 | 1.64 | 3.52 |
| N 1s | 398.000 | 2.969 | 2530.0 | 0.477 | 14.007 | 1.31 | 1.12 |
| C 1s | 283.000 | 4.089 | 69275.0 | 0.278 | 12.011 | 61.67 | 44.89 |
| O 1s | 530.000 | 4.179 | 89832.5 | 0.780 | 15.999 | 28.68 | 27.80 |

There is a significantly reduced presence of Cl in proportion to Fe in the material, suggesting that Cl was released and washed away during the process.

Figure 41B:
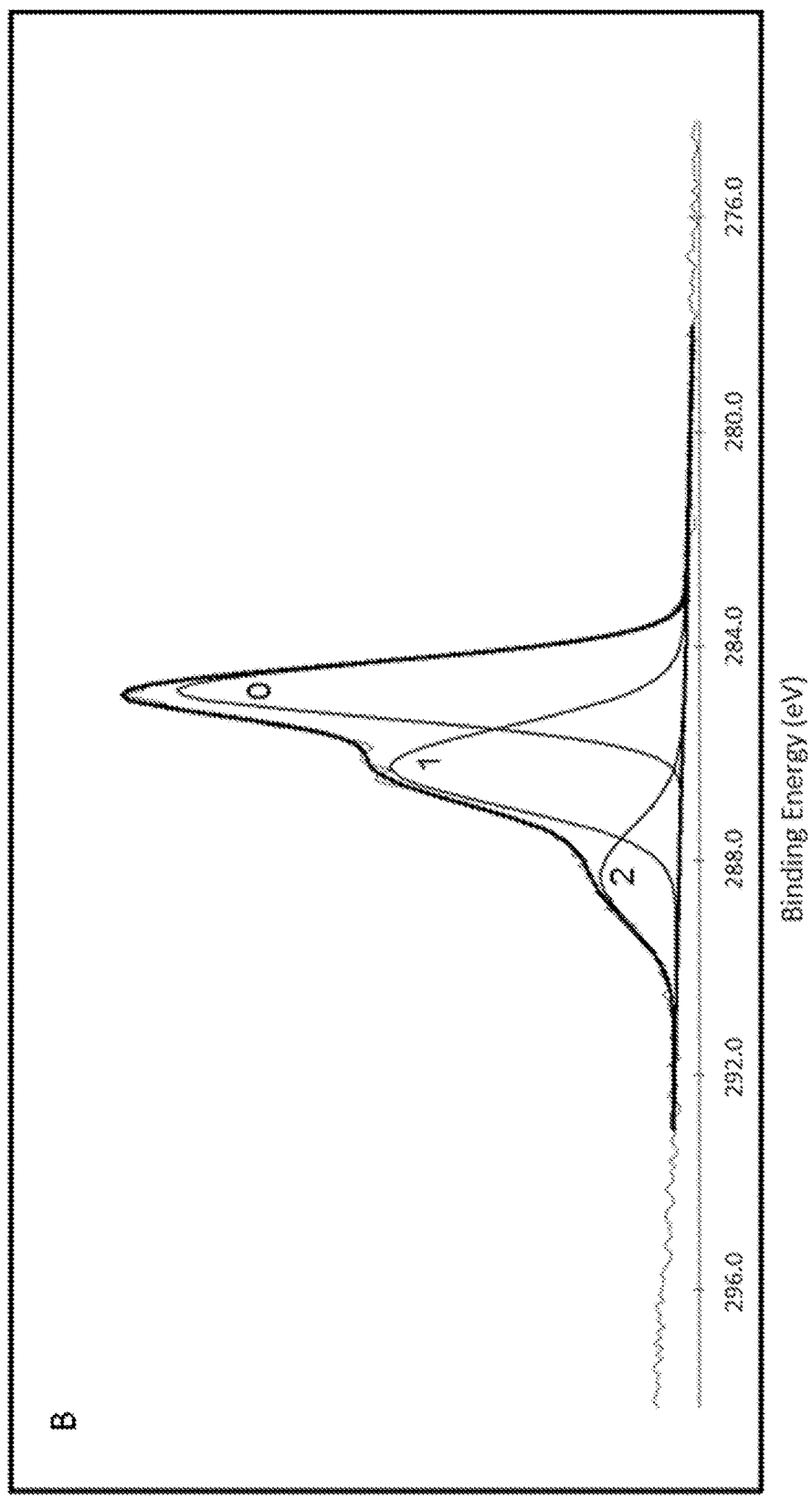

FIG. 41B shows the C 1s spectrum. The peak positions and their corresponding areas are listed in the following table.

| Peak | Position (eV) | FWHM (eV) | Area |
|---|---|---|---|
| 0 | 284.820 | 1.218 | 1751.420 |
| 1 | 286.242 | 1.757 | 1512.195 |
| 2 | 288.276 | 2.162 | 498.409 |

Peak 0 is likely associated with Adventitious Carbon or C—C bond. Peak 1 likely contains C—N, or C—O—H, or C—O—C bonds, which are present in cellulose, arabinoxylan, inulin, beta-glucans and other fiber components. Peak 2 likely contains N—C=O or C=O bonds, which are present in chitin, pectins and other components in natural fiber.

Figure 41C:
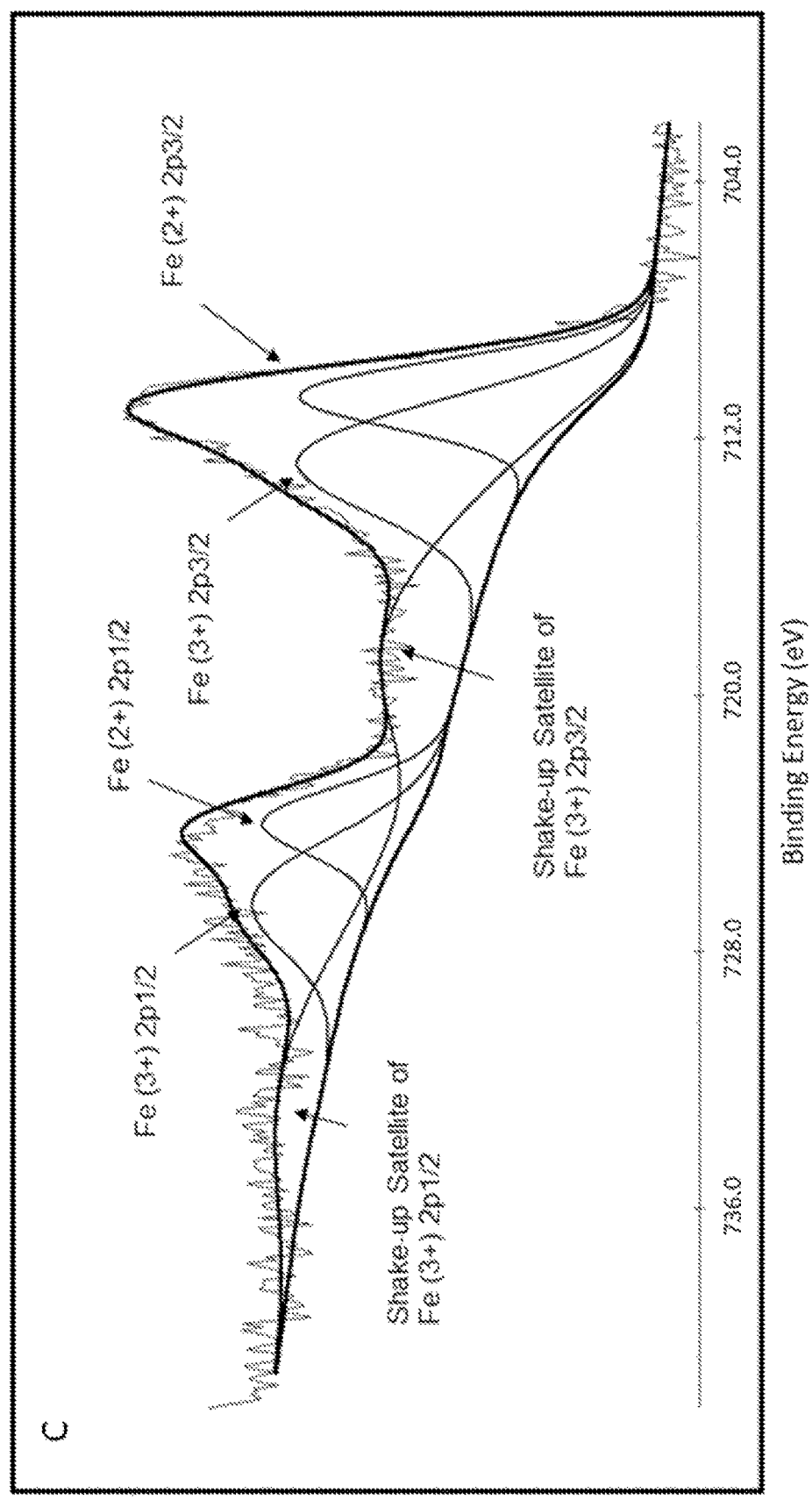

FIG. 41C shows the Fe 2p spectrum. The peak positions and their corresponding areas are listed in the following table.

| Peak | Position (eV) | FWHM (eV) | Area |
|---|---|---|---|
| 0 | 710.585 | 2.483 | 992.150 |
| 1 | 712.493 | 4.138 | 1346.580 |
| 2 | 717.910 | 7.824 | 907.881 |

Note:
The area was calculated from combining 2p1/2 and 2p3/2 for both Fe(3+) and Fe (2+).

The presence of Fe(2+) was calculated to be 42.4% of total Fe (based on the area). The preparation of this material only used $FeCl_3$.

A search in the patent and literature was conducted on XPS and processed fiber. Examples from the search are shown below.

| References | Process | XPS results |
|---|---|---|
| Gustafsson et al., 2003, Polymer 44: 661 | Spruce kraft pulps cooked for different times and further $OD_0E_1D_1E_2D_2$-bleached | O 1s, C 1s |
| Bilba and Arsene, 2008, Composites Part A 39: 1488 | Silane coating of fiber | O 1s, C 1s, Si 2s, Si 2p |
| Wang et al., 2010, BioResources 5: 1799 | Pine chemithermo-mechanical pulp treated with peracetic acid | C 1s (C1, C2, C3), O1s |

Example 26

Figure 42A:
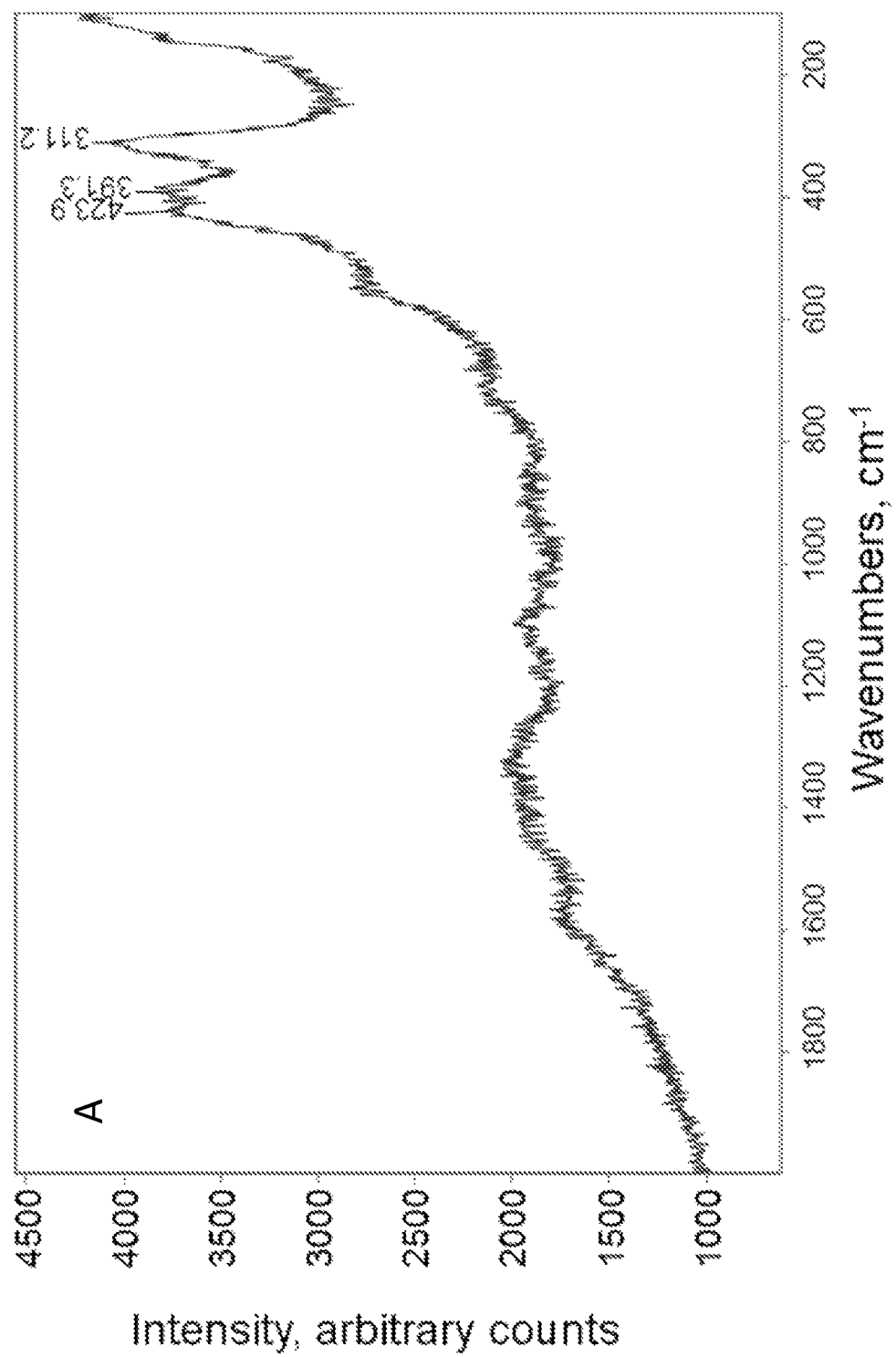
FIG. 42 shows the results from Raman Spectroscopy with 785 nm laser for an iron-fiber composition prepared from dietary fiber and $FeCl_3$ under (A) normal condition and (B) high laser intensity.
Figure 42B:
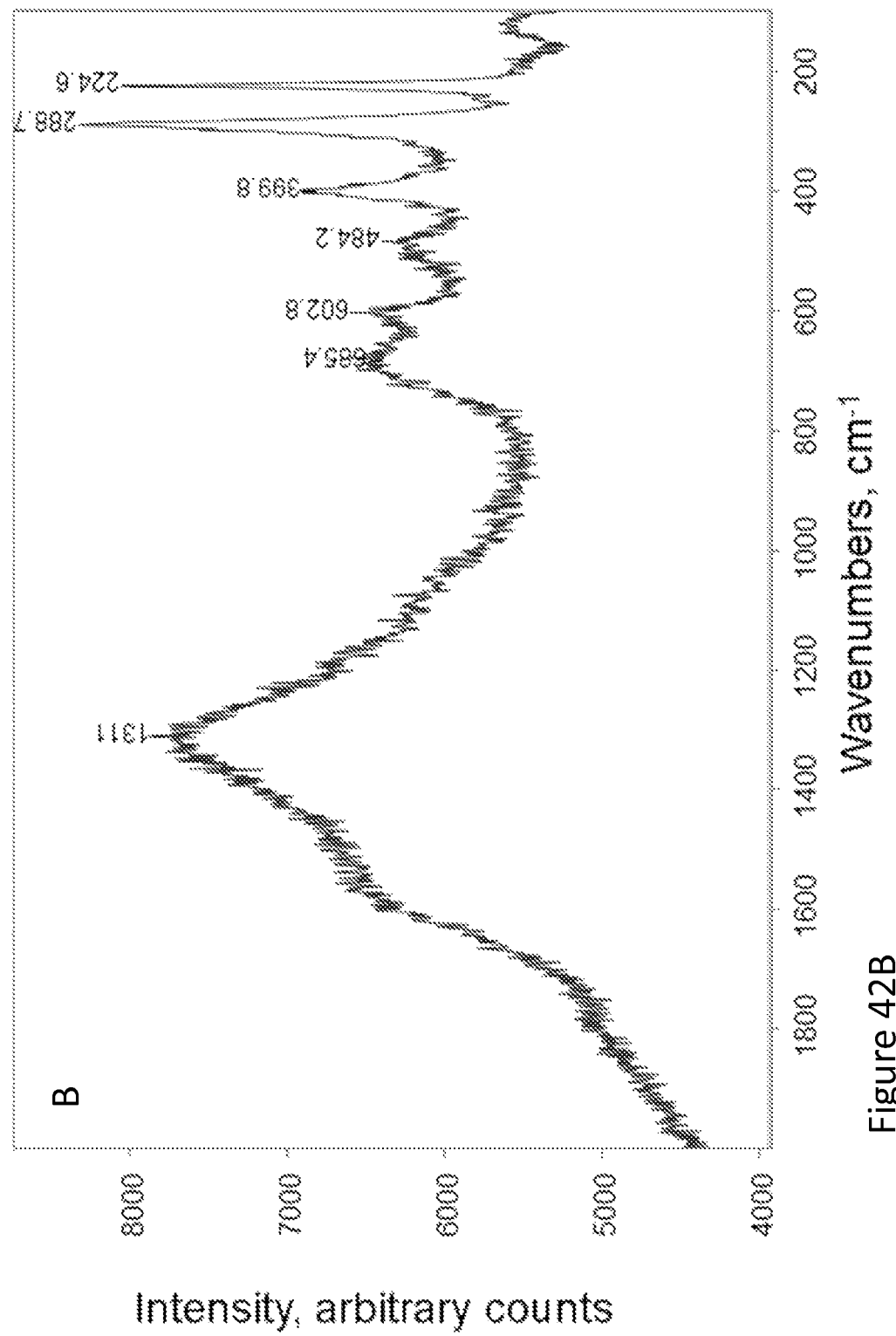

The iron-fiber sample from Example 24 with the iron-fiber prepared from fiber and $FeCl_3$ was analyzed further by the Raman Spectroscopy. Samples were dispersed directly onto Silicon substrates for analysis. The Raman spectra were collected using Renishaw in Via Raman instrument equipped with 785 nm laser. The samples were located using a Leica microscope with a 50× objective. The spectrum for the iron-fiber complex under normal condition is shown in FIG. 42A; the bands indicate the presence of a six-coordinated complex with iron complexed with C, N, O and/or H. FIG. 42B shows the spectrum of the same sample under oxidized condition after the sample was treated with increased temperature and intensity of the laser. The peaks at 224.6, 288.7 and 399.8 correspond with the profile of hematite (iron(III) oxide, $Fe_2O_3$). The broad peak at 1131 corresponds with the C—C and C—O stretches in fiber.

Example 27

Took 0.5 g $FeCl_3$ (Sigma F2877), $FeCl_2$ (Sigma 372870), or iron acetate (Sigma 339199), or $FeSO_4$ (Sigma 215422), or iron(II) ascorbate (Sigma A0207), or iron (III) citrate (Sigma F6129) and mixed with 10 ml water. Adjusted pH if necessary by adding HCl (concentrated) until pH at <3. Added 0.5 g dietary fiber per sample. Incubated the mixture for at least 1 hr at room temperature with shaking. Added NaOH (pH=10). Mixed and incubated at room temperature for at least 1 hr with shaking. Washed with water until the supernatant was clear and the pH was at ~7. Dried for 24 hours using a food dehydrator.

Removed 0.1 g of the dry composition from each sample, and mixed with 5 ml of a 20 mM phosphate solution (1.37 ml of 85% phosphoric acid, 3.18 g of sodium carbonate and 4.68 g of NaCl in 1 liter of water, pH=7.0). Incubated at room temperature for ~3 hrs. Centrifuged and collected the supernatant for phosphate determination using the phosphate colorimetric assay (Catalog #K410-500 from Biovision).

The phosphate-binding property of each sample normalized by per gram of dry iron-fiber was: fiber containing $FeCl_3$ (0.38 mmol/g), fiber containing $FeCl_2$ (0.57 mmol/g), fiber containing iron acetate (0.48 mmol/g), fiber containing $FeSO_4$ (0.20 mmol/g), fiber containing iron(II) ascorbate (0.42 mmol/g), fiber containing iron (III) citrate (0.43 mmol/g).

Example 28

Took 0.5 g $FeCl_3$, or 0.5 g iron acetate, or the mixture of 0.25 g $FeCl_3$ plus 0.25 g iron acetate and mixed with 10 ml water. Checked pH and adjusted pH if necessary by adding HCl (concentrated) until pH at <3. Added 0.5 g dietary fiber per sample. Incubated the mixture for at least 1 hr at room temperature with shaking. Added NaOH to neutralize. Mixed and incubated at room temperature for at least 1 hr with shaking. Washed with water until the supernatant was clear and the pH was at ~7. Dried for 24 hours using a food dehydrator.

Removed 0.1 g of the dry composition from each sample, and mixed with 5 ml of a 20 mM phosphate solution (1.37 ml of 85% phosphoric acid, 3.18 g of sodium carbonate and 4.68 g of NaCl in 1 liter of water, pH=7.0). Incubated at room temperature for ~24 hrs. Centrifuged and collected the supernatant for phosphate determination using the phosphate colorimetric assay (Catalog #K410-500 from Biovision).

The phosphate-binding property of each sample normalized by per gram of dry iron-fiber was: fiber containing $FeCl_3$ alone (0.50 mmol/g), fiber containing iron acetate alone 0 (0.54 mmol/g), fiber containing the mixture of $FeCl_3$ and iron acetate (0.52 mmol/g).

Example 29

Took 0.5 g $FeCl_2$, or 0.5 g $FeSO_4$, or the mixture of 0.25 g $FeCl_2$ and 0.25 g $FeSO_4$, or the mixture of 0.25 g $FeCl_2$ and 0.25 g iron acetate and mixed with 10 ml water. Checked pH and adjusted pH if necessary by adding HCl (concentrated) until pH at <3. Added 0.5 g dietary fiber per sample. Incubated the mixture for at least 1 hr at room temperature with shaking. Added NaOH to neutralize. Mixed and incubated at room temperature for at least 1 hr with shaking. Washed with water until the supernatant was clear and the pH was at ~7. Dried for 24 hours using a food dehydrator.

Removed 0.1 g of the dry composition from each sample, and mixed with 5 ml of a 20 mM phosphate solution (1.37 ml of 85% phosphoric acid, 3.18 g of sodium carbonate and 4.68 g of NaCl in 1 liter of water, pH=7.0). Incubated at room temperature for ~3 hrs. Centrifuged and collected the supernatant for phosphate determination using the phosphate colorimetric assay (Catalog #K410-500 from Biovision).

The phosphate-binding property of each sample normalized by per gram of dry iron-fiber was: fiber containing $FeCl_2$ alone (0.54 mmol/g), fiber containing $FeSO_4$ alone (0.20 mmol/g), fiber containing the mixture of $FeCl_2$ and $FeSO_4$ (0.54 mmol/g), fiber containing the mixture of $FeCl_2$ and iron acetate (0.44 mmol/g).

Example 30

Took 0.5 g $FeCl_3$, or the mixture of 0.45 g $FeCl_3$ plus 0.05 g $FeCl_2$, or the mixture of 0.40 g $FeCl_3$ plus 0.10 g $FeCl_2$, or the mixture of 0.25 g $FeCl_3$ plus 0.25 g $FeCl_2$, or the mixture of 0.10 g $FeCl_3$ plus 0.40 g $FeCl_2$, or 0.5 g $FeCl_2$ and mixed with 10 ml water. Checked pH (<3). Added 0.5 g dietary fiber per sample. Incubated the mixture for at least 1 hr at room temperature with shaking. Added NaOH to neutralize. Mixed and incubated at room temperature for at least 1 hr with shaking. Washed with water until the supernatant was clear and the pH was at ~7. Dried for 24 hours using a food dehydrator.

Removed 0.1 g of the dry composition from each sample, and mixed with 5 ml of a 20 mM phosphate solution (1.37 ml of 85% phosphoric acid, 3.18 g of sodium carbonate and 4.68 g of NaCl in 1 liter of water, pH=7.0). Incubated at room temperature for ~3 hrs. Centrifuged and collected the supernatant for phosphate determination using the phosphate colorimetric assay (Catalog #K410-500 from Biovision).

The phosphate-binding property of each sample normalized by per gram of dry iron-fiber was: fiber containing $FeCl_3$ alone (0.33 mmol/g), fiber containing $FeCl_3$:$FeCl_2$ at 9:1 (0.39 mmol/g), fiber containing $FeCl_3$:$FeCl_2$ at 4:1 (0.49 mmol/g), fiber containing the mixture of $FeCl_3$:$FeCl_2$ at 1:1 (0.51 mmol/g), fiber containing the mixture of $FeCl_3$:$FeCl_2$ at 1:4 (0.45 mmol/g), fiber containing $FeCl_2$ alone (0.51 mmol/g).

Example 31

The iron-fiber sample from Example 29 with the iron-fiber prepared from 0.5 g $FeCl_2$+0.5 g fiber was analyzed further by the XPS (X-ray Photoelectron Spectroscopy). XPS experiments were performed using the Kratos Axis-165 instrument. Samples were irradiated by a monochromatic Al—$K_\alpha$ X-ray source (15 kV, 10 mA) at an angle of 30 degrees from the sample surface. Photoelectrons were detected by 8 channeltrons of the concentric hemispherical analyzer over an area of 700×300 microns, with a spectrometer take-off angle of zero. The detection was achieved using the constant analyzer energy (CAE) mode.

Survey scans were acquired with a pass-energy of 160 eV, 1.0 eV step-size and 100 msec dwell time; while narrow scans were acquired with a pass-energy of 20 eV, 0.1 eV step-size and 200 msec. All scans were performed with the charge-neutralization system running Charge-referencing were done with the adventitious carbon peak position of 284.8 eV. The XPS analysis chamber base-Pressure was better than 2E-10 Torr, while working-Pressure was better than 3E-9 Torr.

Figure 43A:
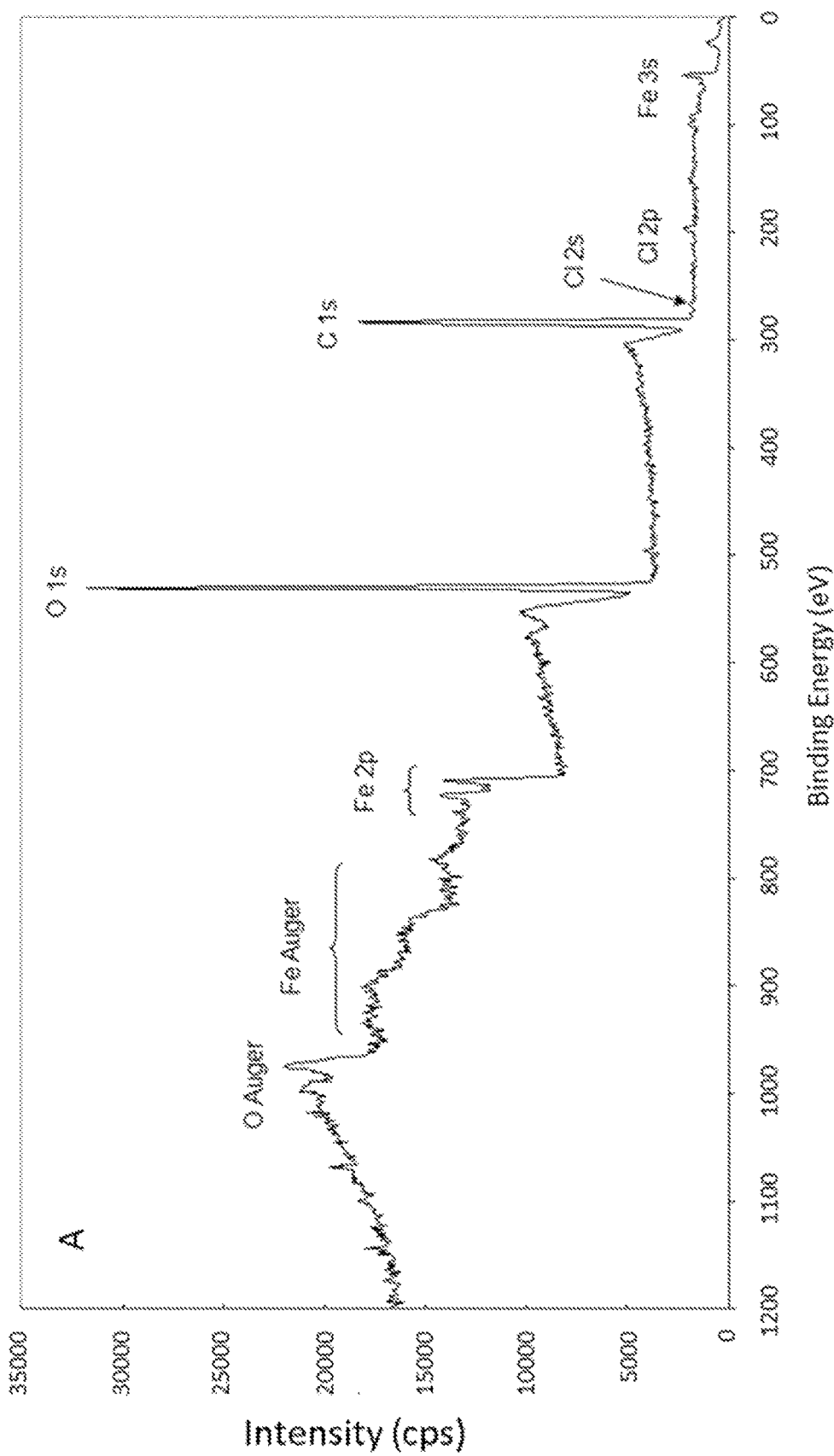
FIG. 43 shows (A) the survey, (B) C 1s and (C) Fe 2p spectrum from XPS analysis of an iron-fiber composition prepared from dietary fiber and $FeCl_2$.

FIG. 43A shows the survey spectrum from the XPS analysis. The semi-quantitation data are listed in the table.

| Peak | Position BE (eV) | FWHM (eV) | Raw Area (CPS) | RSF | Atomic Mass | Atomic Conc, % | Mass Conc, % |
|---|---|---|---|---|---|---|---|
| Fe 2p | 709.000 | 5.043 | 60320.0 | 2.957 | 55.846 | 5.04 | 17.89 |
| Cl 2p | 196.000 | 4.205 | 2660.0 | 0.891 | 35.460 | 0.71 | 1.61 |
| C 1s | 283.000 | 4.129 | 70540.0 | 0.278 | 12.011 | 60.82 | 46.47 |
| O 1s | 530.000 | 3.724 | 108132.5 | 0.780 | 15.999 | 33.43 | 34.03 |

Figure 43B:
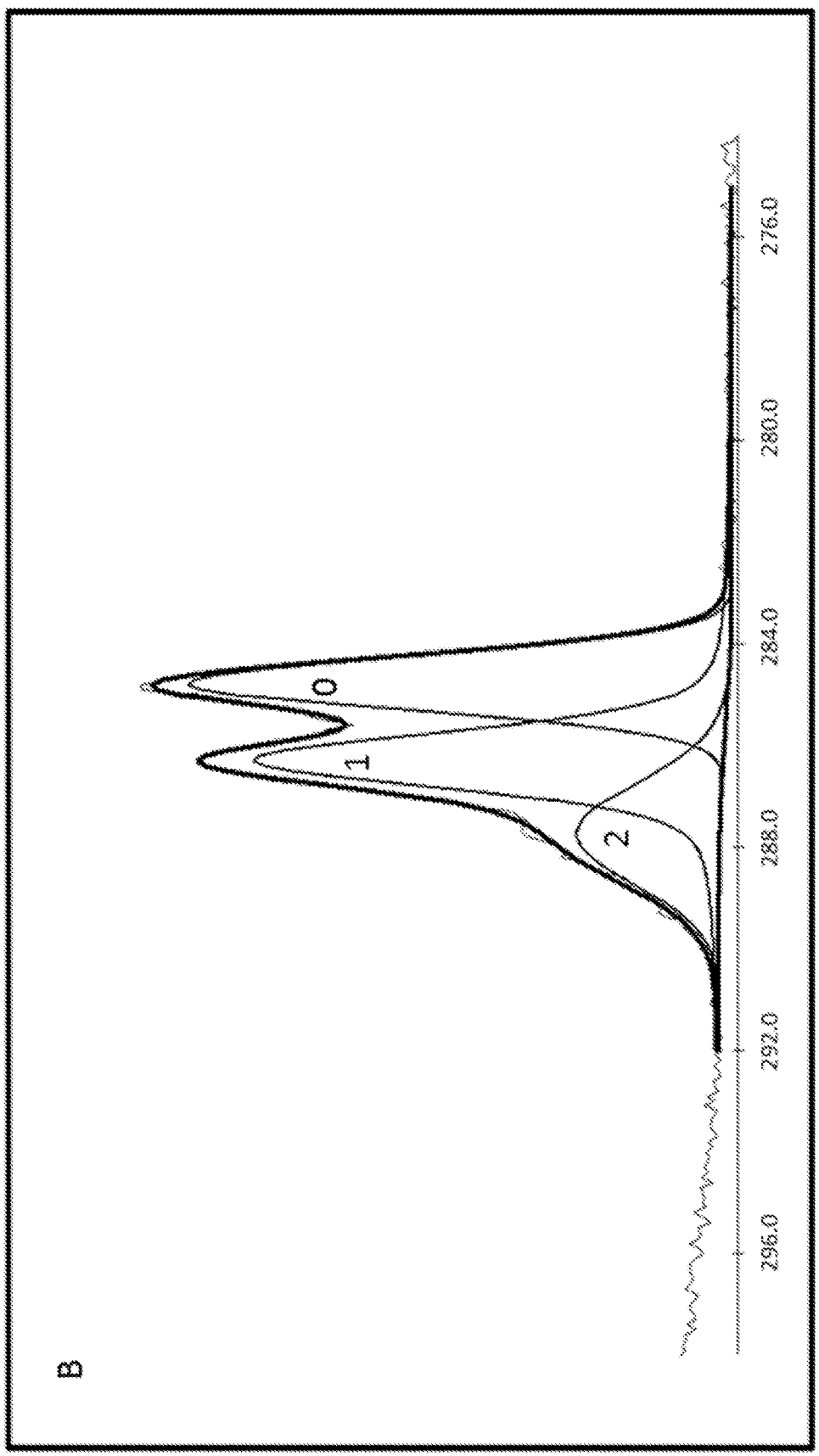

FIG. 43B shows the C 1s spectrum. The peak positions and their corresponding areas are listed in the following table.

| Peak | Position (eV) | FWHM (eV) | Area |
|---|---|---|---|
| 0 | 284.777 | 1.215 | 1210.937 |
| 1 | 286.284 | 1.274 | 1304.316 |
| 2 | 287.734 | 2.306 | 606/741 |

Figure 43C:
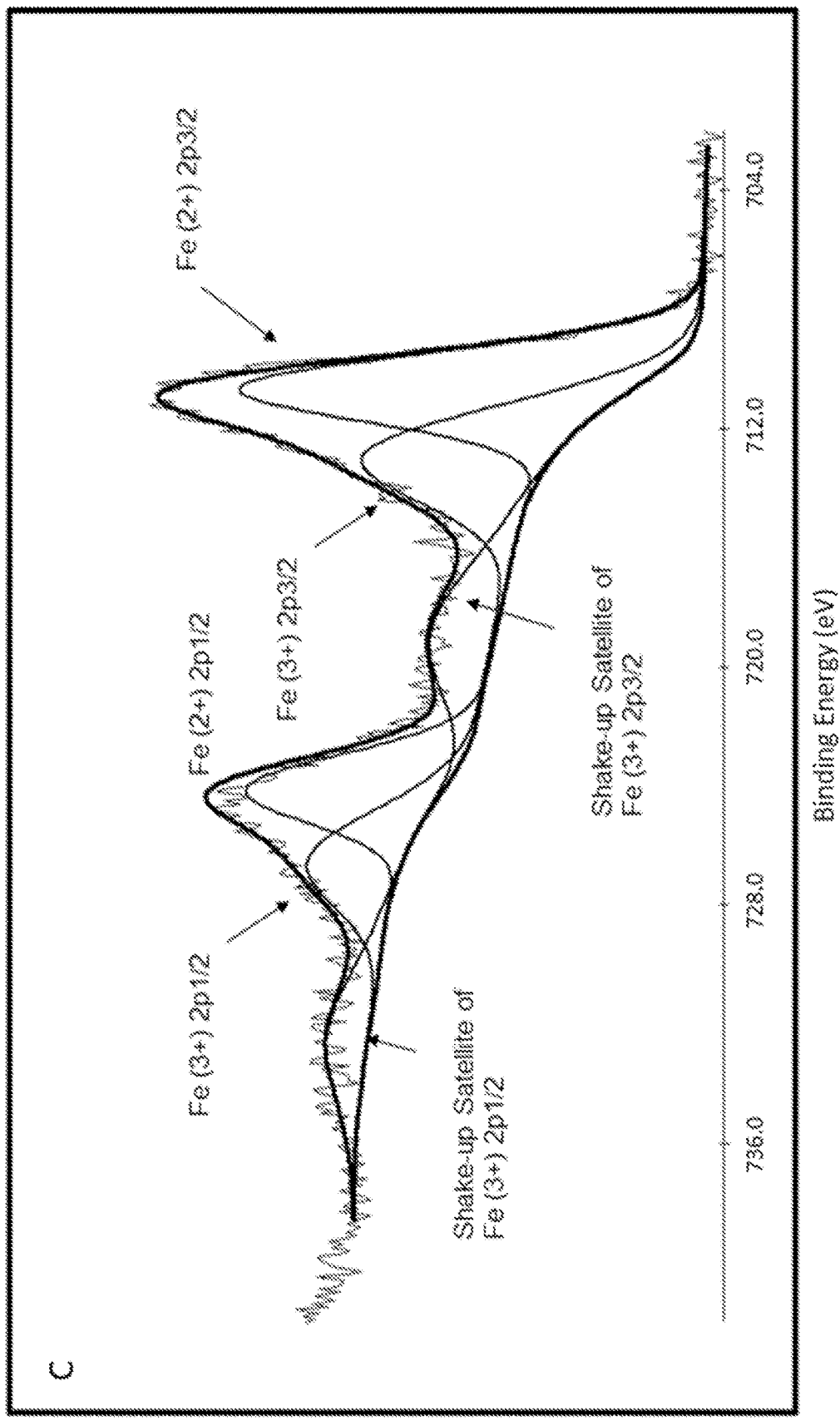

FIG. 43C shows the Fe 2p spectrum. The peak positions and their corresponding areas are listed in the following table.

| Peak | Position (eV) | FWHM (eV) | Area |
|---|---|---|---|
| 0 | 710.532 | 2.686 | 1021.598 |
| 1 | 712.819 | 3.633 | 707.039 |
| 2 | 718.741 | 5.311 | 219.676 |
| 3 | 732.217 | 5.095 | 135.074 |

Note:
The area was calculated from combining 2p1/2 and 2p3/2 for both Fe(3+) and Fe (2+).

The presence of Fe(2+) and Fe(3+) were calculated to be 59% and 41% of total Fe (based on the area), respectively. The preparation of this material only used $FeCl_2$. The presence of Fe (3+) suggests oxidation during the process.

Various embodiments of this invention are described herein. Variations may become apparent to those of ordinary skill in the art upon reading the foregoing description. The inventors expect skilled artisans to employ such variations as appropriate, and the inventors intend for the invention to be practiced otherwise than as specifically described herein. Accordingly, the inventors contemplate all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A composition suitable for oral administration characterized by: (1) being water-insoluble; (2) having Iron (II) and/or Iron (III) tightly bound to dietary fiber containing a mixture of polysaccharides and/or oligosaccharides and lignin with minimal iron release/availability; (3) with a phosphate binding property.

2. The composition of claim 1, wherein the dietary fiber is a natural composition encompassing lignin and saccharides, or a synthetic composition that contains lignin and saccharides.

3. The composition of claim 1, wherein the iron salt is selected from the group consisting of iron(II) acetate, iron (II) citrate, iron(II) ascorbate, iron(II) oxalate, iron(II) oxide, iron(II) carbonate, iron(II) carbonate saccharate, iron(II) formate, iron(II) sulfate, iron(II) chloride, iron(III) chloride, iron (II) bromide, iron (II) iodide, iron (III) fluoride, iron(II) acetylacetonate, iron (III) phosphate, iron (III) pyrophosphate, and combinations thereof.

4. The composition of claim 1, wherein the iron-fiber complex contains iron at 2 wt % to 50 wt % of the composition.

5. The composition of claim 1, optionally wherein the iron is bonded to the dietary fiber containing saccharides and lignin as a complex via carbon, oxygen, nitrogen or hydrogen bridge bonds.

6. The composition of claim 1, wherein the complex is crystalline, amorphous or comprises microdomains of both amorphous and crystalline regions ranging from 10% to 90% amorphous and 10% to 90% crystalline.

7. The composition of claim 1, wherein the composition has a density of >1 g/ml in its compressed dry form, and has a density of 0.2-0.5 g/ml after being exposed to liquids.

8. The composition of claim 1, wherein the composition is capable of binding to minerals, ions, toxins, metabolites at a wide pH range and optionally wherein the composition is stable at pH 1-12, and remains efficacious at a pH range between 1 to 12.

9. A process for producing an orally administrable composition according to claim 1 comprising the steps of: (a) mixing dietary fiber containing a mixture of polysaccharides and/or oligosaccharides and lignin with an Iron(II) or Iron (III) compound, at a pH <3; (b) maintaining a temperature of reaction mixture of step (a) between ambient and 100° C.; (c) cooling the reaction mixture of step (b) to ambient temperature; (d) adjusting the pH using base until pH>3 with clusters of precipitates formed; and (e) washing the precipitates until pH is neutral; and (f) isolating the composition thereof, wherein the reaction mixture is optionally exposed to pressure during step (b).

10. The process of claim 9, wherein the pH<3 in step (a) of the process can be reached by addition of an acid selected from the group consisting of: hydrogen halides especially hydrochloric acid (HCl), hydrobromic acid (HBr), hydroiodic acid (HI), halogen oxoacids especially hypochlorous acid (HClO), chlorous acid ($HClO_2$), chloric acid ($HClO_3$), perchloric acid ($HClO_4$), and corresponding acids for bromine and iodine, sulfuric acid ($H_2SO_4$), fluorosulfuric acid ($HSO_3F$), nitric acid ($HNO_3$), phosphoric acid ($H_3PO4$), fluoroantimonic acid ($HSbF_6$), fluoroboric acid ($HBF_4$), hexafluorophosphoric acid ($HPF_6$), chromic acid ($H_2CrO_4$), and boric acid ($H_3BO_3$).

11. The process of claim 9, wherein the base used in step (d) of the process is selected from LiOH, KOH, NaOH, $NaHCO_3$, $Na_2CO_3$, $Ca(OH)_2$, $Mg(OH)_2$, $Li_2CO_3$, $K_2CO_3$, $CaCO_3$, and $MgCO_3$.

12. The composition of claim 1, wherein the composition is formulated as a nutritional supplement, a beverage, a snack bar, or a cereal.

13. The composition of claim 1, wherein the composition is formulated as a medicament.

14. The medicament of claim 13, wherein the composition is selected from the group consisting of capsules, sachets, tablets, lozenges, wafers, powders, suspensions in an appropriate liquid.

15. The medicament of claim 13, wherein the medicament is used to adsorb excess phosphate, cholesterol, and toxins from infectious agents.

16. The composition of claim 1, formulated for use according to extracorporeal, ex vivo, or in vitro administration to a subject in need thereof.

17. The composition of claim 1, wherein the composition is formulated as an elemental medical food comprising at least 10 mg of the composition according to claim 1 in a physiological carrier.

18. The elemental medical food of claim 17, formulated as a pill, a tablet, a powder, a bar, a wafer, a suspensions in an appropriate liquid.

19. The elemental medical food of claim 17, further comprising one or more ingredients selected from the group consisting of natural flavors, artificial flavors, major trace and ultra-trace minerals, minerals, vitamins, oats, nuts, spice, milk, egg, salt, flour, lecithin, xanthan gum, and sweetening agents.

20. The composition of claim 1, wherein said complex is formulated as a food supplement suitable for mammals comprising at least 10 mg of the composition according to claim 1.

21. The food supplement of claim 20 formulated as a powder, a bar, a wafer, a suspension in an appropriate liquid.

22. The food supplement of claim 20 comprising one or more additional ingredients selected from the group consisting of natural flavor, artificial flavors, major trace and ultra-trace minerals, minerals, vitamins, oats, nuts, spice, milk, egg, salt, flour, lecithin, xanthan gum, or sweetening agents.

* * * * *

UNITED STATES PATENT AND TRADEMARK OFFICE
CERTIFICATE OF CORRECTION

PATENT NO. : 9,566,303 B2  
APPLICATION NO. : 14/349134  
DATED : February 14, 2017  
INVENTOR(S) : Jinshyun Ruth Wu-Wong Page 1 of 1

It is certified that error appears in the above-identified patent and that said Letters Patent is hereby corrected as shown below:

In the Specification

In Column 1, immediately prior to the FIELD OF THE INVENTION, add the following:

--STATEMENT OF GOVERNMENT INTEREST  
This invention was made with support under Grant Number DK096698 awarded by the National Institutes of Health. The Government has certain rights in the invention.--

Signed and Sealed this  
Twenty-sixth Day of June, 2018

Andrei Iancu  
*Director of the United States Patent and Trademark Office*